US011697693B2

(12) United States Patent
Schoenfisch et al.

(10) Patent No.: US 11,697,693 B2
(45) Date of Patent: Jul. 11, 2023

(54) NITRIC OXIDE-RELEASING ALGINATES AS BIODEGRADABLE ANTIBACTERIAL SCAFFOLDS AND METHODS PERTAINING THERETO

(71) Applicant: The University of North Carolina at Chapel Hill, Chapel Hill, NC (US)

(72) Inventors: Mark H. Schoenfisch, Chapel Hill, NC (US); Mona Jasmine R. Ahonen, Chapel Hill, NC (US); Dakota J. Suchyta, Chapel Hill, NC (US); Kaitlyn Rose Rouillard, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 11 days.

(21) Appl. No.: 17/385,497

(22) Filed: Jul. 26, 2021

(65) Prior Publication Data
US 2021/0347918 A1 Nov. 11, 2021

Related U.S. Application Data

(62) Division of application No. 16/475,615, filed as application No. PCT/IB2018/050051 on Jan. 3, 2018, now Pat. No. 11,072,668.

(60) Provisional application No. 62/441,742, filed on Jan. 3, 2017, provisional application No. 62/483,505, filed on Apr. 10, 2017.

(51) Int. Cl.
| | |
|---|---|
| *C08B 37/00* | (2006.01) |
| *A61P 11/12* | (2006.01) |
| *A61P 31/04* | (2006.01) |
| *A01N 65/03* | (2009.01) |
| *A61K 31/734* | (2006.01) |

(52) U.S. Cl.
CPC .......... *C08B 37/0084* (2013.01); *A01N 65/03* (2013.01); *A61K 31/734* (2013.01); *A61P 11/12* (2018.01); *A61P 31/04* (2018.01)

(58) Field of Classification Search
CPC .............. C08B 37/003; C08B 37/0072; C08B 37/0084; C08L 1/286; C08L 5/04; C08L 5/08
See application file for complete search history.

(56) References Cited

U.S. PATENT DOCUMENTS

| | | |
|---|---|---|
| 4,169,079 A | 9/1979 | Tabushi et al. |
| 5,234,933 A | 8/1993 | Marnett et al. |
| 5,326,902 A | 7/1994 | Seipp et al. |
| 5,525,357 A | 6/1996 | Keefer et al. |
| 5,574,027 A | 11/1996 | Bernstein |
| 5,632,981 A | 5/1997 | Saavedra et al. |
| 5,650,442 A | 7/1997 | Mitchell et al. |
| 5,650,447 A | 7/1997 | Keefer et al. |
| 5,714,511 A | 2/1998 | Saavedra et al. |
| 5,814,666 A | 9/1998 | Green et al. |
| 5,840,759 A | 11/1998 | Mitchell et al. |
| 5,910,316 A | 6/1999 | Keefer et al. |
| 6,110,453 A | 8/2000 | Keefer et al. |
| 6,121,441 A | 9/2000 | Simensen et al. |
| 6,180,082 B1 | 1/2001 | Weltering et al. |
| 6,200,558 B1 | 3/2001 | Saavedra et al. |
| 6,261,594 B1 | 7/2001 | Smith et al. |
| 6,451,337 B1 | 9/2002 | Smith et al. |
| 6,911,433 B2 | 6/2005 | Saavedra et al. |
| 7,553,656 B2 | 6/2009 | Gimmestad et al. |
| 7,928,079 B2 | 4/2011 | Hrabie et al. |
| 8,158,580 B2 | 4/2012 | Judice et al. |
| 8,603,454 B2 | 12/2013 | Cheng et al. |
| 8,815,831 B2 | 8/2014 | Onsoyen et al. |
| 8,841,279 B2 | 9/2014 | Taylor et al. |
| 8,987,215 B2 | 3/2015 | Taylor et al. |
| 9,238,038 B2 | 1/2016 | Schoenfisch et al. |
| 9,539,233 B2 | 1/2017 | Ohtake et al. |
| 9,850,322 B2 | 12/2017 | Schoenfisch et al. |
| 10,759,877 B2 | 9/2020 | Schoenfisch et al. |
| 11,026,965 B2 | 6/2021 | Schoenfisch et al. |
| 11,072,668 B2 | 7/2021 | Schoenfisch et al. |
| 2001/0000039 A1 | 3/2001 | Toone et al. |
| 2002/0122857 A1 | 9/2002 | Asai et al. |
| 2003/0078365 A1 | 4/2003 | Stamler et al. |
| 2003/0093143 A1 | 5/2003 | Zhao et al. |
| 2004/0038947 A1 | 2/2004 | Wink et al. |
| 2005/0009789 A1 | 1/2005 | Wink et al. |
| 2005/0085413 A1 | 4/2005 | Jin et al. |
| 2005/0228184 A1 | 10/2005 | Haj-Yehia |

(Continued)

FOREIGN PATENT DOCUMENTS

| | | |
|---|---|---|
| CA | 2205564 C | 7/2006 |
| CN | 101049513 A | 10/2007 |

(Continued)

OTHER PUBLICATIONS

Ahonen et al., "Nitric oxide-releasing alginates as mucolytic agents," ACS Biomater. Sci. Eng., 5:3409-3418, (2019).

Ahonen et al.."Nitric oxide-releasing alginate as a biodegradable antibacterial scaffold," 253rd National Metting of the American Chemical Society (ACS) on Advanced Materials, Technologies, Systems, and Processes; San Francisco, CA, Apr. 2-6, 2017—Abstracts of Papers, p. 600, (2017).

Allaker, R.P., "The use of Nanoparticies to Control Oral Biofiim formation," J Dent Res, 89(11):1175-1186, (2010).

Alnaief et al., "Preparation of biodegradable nanoporous microspherical aerogel based on alginate," Carbohydrate Polymers, 84(3):1011-1018, (2011).

(Continued)

*Primary Examiner* — Pancham Bakshi
(74) *Attorney, Agent, or Firm* — Alston & Bird LLP

(57) ABSTRACT

Large molecular weight alginates which are covalently modified to store and release nitric oxide, as well as methods of making and use thereof, are disclosed herein. The covalently modified alginates may be tailored to release nitric oxide in a controlled manner and are useful for eradication of both planktonic and biofilm-based bacteria.

21 Claims, 22 Drawing Sheets

(56) References Cited

U.S. PATENT DOCUMENTS

| | | |
|---|---|---|
| 2005/0265956 A1 | 12/2005 | Liu et al. |
| 2006/0199785 A1 | 9/2006 | Fahmi et al. |
| 2007/0243131 A1 | 10/2007 | Chen et al. |
| 2008/0305004 A1 | 12/2008 | Anderson et al. |
| 2009/0214618 A1 | 8/2009 | Schoenfisch et al. |
| 2009/0222088 A1 | 9/2009 | Chen et al. |
| 2009/0232863 A1 | 9/2009 | Cheng et al. |
| 2010/0197631 A1 | 8/2010 | Reiner et al. |
| 2010/0305062 A1 | 12/2010 | Onsoyen et al. |
| 2010/0305489 A1 | 12/2010 | Liu et al. |
| 2011/0002999 A1 | 1/2011 | Chen et al. |
| 2011/0150999 A1 | 6/2011 | Chu et al. |
| 2011/0218139 A1 | 9/2011 | Robinson et al. |
| 2012/0034169 A1 | 2/2012 | Schoenfisch et al. |
| 2012/0107229 A1 | 5/2012 | Huang et al. |
| 2013/0096078 A1 | 4/2013 | Yoon et al. |
| 2013/0196951 A1 | 8/2013 | Schoenfisch et al. |
| 2013/0337033 A1 | 12/2013 | Balkus, Jr. et al. |
| 2014/0256658 A1 | 9/2014 | Sinha et al. |
| 2015/0126467 A1 | 5/2015 | Onsøyen et al. |
| 2015/0225488 A1 | 8/2015 | Schoenfisch et al. |
| 2016/0185891 A1* | 6/2016 | Chambers ............ C08B 37/003 527/312 |
| 2016/0331777 A1 | 11/2016 | Dessen et al. |
| 2016/0346313 A1 | 12/2016 | Taylor Nordgard et al. |
| 2016/0361342 A1 | 12/2016 | Hansson et al. |
| 2017/0333456 A1 | 11/2017 | Miranda et al. |
| 2018/0055873 A1 | 3/2018 | Dessen et al. |
| 2019/0197631 A1 | 6/2019 | Schneider |
| 2019/0225747 A1 | 7/2019 | Schoenfisch et al. |
| 2019/0322770 A1 | 10/2019 | Schoenfisch et al. |
| 2019/0343869 A1 | 11/2019 | Schoenfisch et al. |
| 2020/0021657 A1 | 1/2020 | Brinkmann et al. |
| 2020/0030362 A1 | 1/2020 | Schoenfisch et al. |
| 2020/0216571 A1 | 7/2020 | Schoenfisch et al. |
| 2020/0332061 A1 | 10/2020 | Schoenfisch et al. |
| 2021/0346424 A1 | 11/2021 | Schoenfisch et al. |

FOREIGN PATENT DOCUMENTS

| | | |
|---|---|---|
| CN | 102083862 A | 6/2011 |
| CN | 106046382 A | 10/2016 |
| EP | 0726768 B1 | 5/2000 |
| EP | 2547660 B1 | 1/2015 |
| EP | 3185853 A1 | 7/2017 |
| IN | 2010DN04583 A | 11/2010 |
| IN | 2012DN00042 A | 4/2015 |
| JP | 2001-524991 A | 12/2001 |
| JP | 2002-518557 A | 6/2002 |
| JP | 2005047979 A | 2/2005 |
| JP | 4285775 B2 | 6/2009 |
| NO | 20050480 L | 4/2005 |
| WO | WO 93/25521 A1 | 12/1993 |
| WO | WO 1996/015797 A1 | 5/1996 |
| WO | WO 1996/032136 | 10/1996 |
| WO | WO 1998/005689 A1 | 2/1998 |
| WO | WO 1998/013358 A1 | 4/1998 |
| WO | WO 00/30658 A1 | 6/2000 |
| WO | WO 2007/085254 A1 | 8/2007 |
| WO | WO 2009/049208 A1 | 4/2009 |
| WO | WO 2010/037179 A1 | 4/2010 |
| WO | WO 2010/096320 A2 | 8/2010 |
| WO | WO 2010/139957 A1 | 12/2010 |
| WO | WO 2010/139958 A1 | 12/2010 |
| WO | WO 2010/139959 A2 | 12/2010 |
| WO | WO 2011/003172 A1 | 1/2011 |
| WO | WO 2012/046994 A2 | 4/2012 |
| WO | WO 2012/116177 A2 | 8/2012 |
| WO | WO 2013/029009 A1 | 2/2013 |
| WO | WO 2014/028847 A1 | 2/2014 |
| WO | WO 2017/060388 A1 | 4/2017 |
| WO | WO 2018/067838 A1 | 4/2018 |
| WO | WO 2018/127819 A1 | 7/2018 |
| WO | WO 2018/178902 A1 | 10/2018 |
| WO | WO 2019/099525 A1 | 5/2019 |
| WO | WO 2019/173539 A1 | 9/2019 |
| WO | WO 2020/139857 A1 | 7/2020 |

OTHER PUBLICATIONS

Arulsamy, N. et al. "Multiplicity Control in the Polygeminai Diazeniumdiolation of Active Hydrogen Bearing Carbons: Chemistry of a New Type of Trianionic Molecular Propeller," S. J. Am. Chem. Soc.,123:10860-10869, (2001).

Backlund et al., "Antibacterial Efficacy of Exogenous Nitric Oxide on Periodontal Pathogens," J Dent Res, 93(11):1089-1094, (2014).

Backlund et al., "Anti-biofilm action of nitric oxide-releasing alkyl-modified poly(amidoamine) dendrimers against *Streptococcus* mutans," Acta Biomaterialia, 29:198-205, (2016).

Backlund et al., "Kinetic-dependent Killing of Oral Pathogens with Nitric Oxide," J Dent Res, 94(8):1092-1098, (2015).

Barraud et al., "Nitric Oxide: A Key Mediator of Biofilm Dispersal with Applications in Infectious Diseases," Curr. Pharm. Des., 21(1):31-42, (2015).

Barraud et al., "Involvement of Nitric Oxide in Biofilm Dispersal of *Pseudomonas aeruginosa*," Journal of Bacteriology, 188(21):7344-7353, (2006).

Beck et al., "Systemic Effects of Periodontitis: Epidemiology of Periodontal Disease and Cardiovascular Disease," J. Periodontol., 76(11)(Suppl.):2089-2100, (2005).

Belley, A. et al., "Assessment by time-kill methodology of the synergistic effects of oritavancin in combination with other antimicrobial agents against *Staphylococcus aureus*," Antimicrob. Agents Chemother., 52:3820-3822, (2008).

Benkovics et al., "A multifunctional β-cyclodextrin-conjugate photodelivering nitric oxide with fluorescence reporting," International Journal of Pharmaceutics, 531: 614-620 (2017).

Bernkop-Schnurch et al., "Improvement in the mucoadhesive properties of alginate by the covalent attachment of cysteine," Journal of Controlled Release, 71(3):277-285, (2001).

Besinis et al., "Review of Nanomaterials in Dentistry: Interactions with the Oral Microenvironment, Clinical Applications, Hazards, and Benefits," ACS Nano, 9(3):2255-2289, (2015).

Beveridge, Terry J., "Structures of Gram-Negative Cell Walls and Their Derived Membrane Vesicles," Journal of Bacteriology, 181(16):4725-4733, (1999).

Bhardwaj, Atul, et al., "A diazen-1-ium-1, 2-diolate analog of 7-azabenzobicyclo [2.2. 1] heptane: Synthesis, nitric oxide and nitroxyl release, in vitro hemodynamic, and anti-hypertensive studies," Bioorganic & Medicinal Chemistry Letters, 23(9):2769-2774, (2013).

Bjarnsholt et al., "Why chronic wounds will not heal: a novel hypothesis," Wound Rep Reg, 16:2-10, (2008).

Boas and Heegaard, "Dendrimers in drug research," Chem. Soc. Rev., 33(1):43-63, (2004).

Bogdan, Christian, "Nitric oxide and the immune response," Nat. Immunol., 2(10):907-916, (2001).

Bollenbach, T., "Antimicrobial interactions: mechanisms and implications for drug discovery and resistance evolution," Curr. Opin. Microbiol., 27:1-9, (2015).

Breed and Dotterrer, "The number of colonies allowable on satisfactory agar plates," J. Bacteriol. 1(3):321-331, (1916).

Calabretta et al., "Antibacterial activities of poly (amidoamine) dendrimers terminated with amino and poly (ethylene glycol) groups," Biomacromolecules, 8(6):1807-1811, (2007).

Caleffi-Ferracioli et al., "Fast detection of drug interaction in *Mycobacterium* tuberculosis by a checkerboard resazurin method," Tuberculosis, 93:660-663, (2013).

Caminade et al., "Dendrimers and hyperbranched polymers," Chem. Soc. Rev, 44(12):3870-3873, (2015).

Cao et al., "Synthesis and striking fluorescence properties of hyperbranched poly (amido amine)," J. Macromol. Sci. Pure Appl. Chem., 44(4):417-424, (2007).

Caraher, E. M. et al., "The effect of recombinant human lactoferrin on growth and the antibiotic susceptibility of the cystic fibrosis

(56) References Cited

OTHER PUBLICATIONS pathogen Burkholderia cepacia complex when cultured planktonically or as biofilms," J. Antimicrob. Chemother., 60:546-554, (2007).
Carlmark et al., "New methodologies in the construction of dendritic materials," Chem. Soc. Rev., 38(2):352-362, (2009).
Carlmark, A. et al., "Dendritic Architechtures Based on bis-MPA: Functional Polymeric Scaffolds for Application-Driven Research," Chem Soc Rev., 42:5858-79, (2013).
Carpenter et al., "Dual action antimicrobials: nitric oxide release from quaternary ammonium-functionalized silica nanoparticies," Biomacromolecules, 13(10):3334-3342, (2012).
Carpenter et al., "Nitric oxide release: Part II. Therapeutic applications," Chem. Soc. Rev., 41(10):3742-3752, (2012).
Centers for Disease Control, Antibiotic Resistance Threats in the United States, (2013).
Chakrapani, Harinath, et al., "Nitric oxide prodrugs: diazeniumdiolate anions of hindered secondary amines," Organic Letters, 9(22): 4551-4554, (2007).
Charbonneau et al., "Reduced chlorhexidine tooth stain coverage by sequential administration of monoperoxyphthalic acid in the beagle dog," J. Dent. Res., 76(9):1596-1601, (1997).
Chen et al., "Cytotoxicity, hemolysis, and acute in vivo toxicity of dendrimers based on melamine, candidate vehicles for drug delivery," J. Am. Chem. Soc., 126(32):10044-10048, (2004).
Chen et al., "Cariogenic Actinomyces Identified with a β-Glucosidase-Dependent Green Color Reaction to Gardenia jasminoides Extract," Journal of Clinical Microbiology, 39(8):3009-3012, (2001).
Chen et al., "Hyperbranched glycoconjugated polymer from natural small molecule kanamycin as a safe and efficient gene vector," Polym. Chem., 2:2674-2682, (2011).
Chen et al., "Hyperbranched polymers from A2 +B 3 strategy: recent advances in description and control of fine topology," Polym. Chem., 7(22):3643-3663, (2016).
Chen et al., "Multifunctional Hyperbranched Giycoconjugated Polymers Based on Natural Aminoglycosides," Bioconjugate Chemistry, 23(6):1189-1199, (2012).
Chen et al., "Selective deprotection of the Cbz amine protecting group for the facile synthesis of kanamycin A dimers linked at N-3" position," Tetrahedron, 65(31)5922-5927, (2009).
Cheng et al., "Michael Addition Polymerization of Trifunctional Amine and Acrylic Monomer: A Versatile Platform for Development of Biomateriais ," Biomacromolecules, 17(10):3115-3126, (2016).
Ciacci, N., et al., "In vitro Synergism of Colistin and N-acetylcysteine against Stenotrophomonas maltophilia," Antibiotics, 8:101, (2019).
Ciofu, O. & Tolker-Nielsen, T., "Tolerance and Resistance of Pseudomonas aeruginosa Biofilms to Antimicrobial Agents—How P. aeruginosa Can Escape Antibiotics," Front. Microbiol., 10:913, (2019).
Cleland, W.W., "Diothiothreitol, A New Protective Reagent for SH Groups," Biochemical., 3(4):480-482, (1964).
Compound Summary, "PubChem Compound Summary for CID 65430: Gallium citrate ga-67," National Library of Medicine: National Center for Biotechnology Information, (Last accessed Aug. 7, 2020), https://pubchem.ncbi.nlm.nih.gov/compound/Gallium-citrate-ga-67.
Compound Summary, "Gallium citrate Ga-67," Drugbank, (Last accessed Aug. 6, 2020), https://www.drugbank.ca/drugs/DB06784.
Compound Summary, "PubChem Compound Summary for CID 61635, Gallium nitrate," National Library of Medicine: National Center for Biotechnology Information, (Last accessed Aug. 7, 2020) https://pubchem.ncbi.nlm.nih.gov/compound/61635.
Coneski and Schoenfisch, "Nitric oxide release: part III. Measurement and reporting," Chem. Soc. Rev, 41(10):3753-3758, (2012).
Coneski, "Design and Synthesis of Nitric Oxide Releasing Polymers for Biomedical Applications", pp. 122-127, (2010). [Retrieved from the Internet: URL:https://cdr.lib.unc.edu/indexablecontent/uuid:d84bce49-d4dd-4026-96a5-3ea9e82dee9c [retrieved on Oct. 9, 2015]].
Coneski, P.N. and Schoenfisch, M.H., "Synthesis of Nitric Oxide-Releasing Polyurethanes with S-Nitrosothiol-Containing Hard and Soft Segments," Polym Chem., 2(4):906-913, (2011).
Coneski, P.N. et al., "Degradable Nitric Oxide-Releasing Biomateriais via Post-Polymerization Functionalization of Cross-Linked Polyesters," Biomacromolecules, 11(11):3208-3215, (2010).
Cooke et al., "Nitric Oxide and Angiogenesis," Circulation, 165:2133-2135, (2002).
Cooke, John P., "NO and Angiogenesis," Atherosclerosis Suppi., 4(4):53-60, (2003).
Cullen, L. & Mcclean, S., "Bacterial adaptation during chronic respiratory infections," Pathogens, 4:66-89, (2015).
Cutrone et al., "Mannoside and 1,2-mannobioside β-cyclodextrin-scaffolded NO-photodonors for targeting antibiotic resistant bacteria", Carbohydr. Polym, 199: 649-660, (2018).
Da Silva et al., "Antimicrobial peptide control of pathogenic microorganisms of the oral cavity: A review of the literature," Peptides, 36(2):315-321, (2012).
Damodaran, V.B. and Reynolds, M.M., "Biodegradable S-Nitrosothiol Tethered Multiblock Polymer for Nitric Oxide Delivery," J Mater Chem., 21:5870-5872, (2011).
Davies et al., "Evolutionary diversification of Pseudomonas aeruginosa in an artificial sputum model," BMC Microbiol. 17:3, (2017).
Davies et al., "Chemistry of the diazeniumdioiates. 2. Kinetics and Mechanism of Dissociation to Nitric Oxide in Aqueous Solution," JACS, 123(23):5473-5481, (2001).
Deng et al., "pH and cation-responsive supramoleculargels formed by cyclodextrin amines in DMSO," Soft Matter, 6:1884-1887, (2010).
Deupree, S. M. & Schoenfisch, M. H., "Morphologicai analysis of the antimicrobial action of nitric oxide on Gram-negative pathogens using atomic force microscopy," Acta Biomater., 5:1405-1415, (2009).
Draget et al., "Chemical, physical and biological properties of alginates and their biomedical implications," Food Hydrocolloids, 25(2):251-256, (2011).
Drug Development Pipeline Status, "Inhaled Gallium: Phase One", Cystic Fibrosis Foundation, (Last accessed Aug. 13, 2020), https://www.cff.org/Trials/Pipeline/details/10146/Inhaled-Gallium.
Ducan and Izzo, "Dendrimer biocompatibility and toxicity," Adv. Drug Deliv. Rev., 57(14):2215-2237, (2005).
Duong et al., "Functional gold nanoparticies for the storage and controlled release of nitric oxide: applications in biofilm dispersal and intracellular delivery," J. Mater. Chem. B-2, 2(31):5003-5011, (2014).
Duong et al., "Nanoparticle (Star Polymer) Delivery of Nitric Oxide Effectively Negates Pseudomonas aeruginosa Biofilm Formation," Biomacromolecules, 15(7):2583-2589, (2014).
Elion et al., "Antagonists of Nucleic Acid Derivatives: VIII. Synergism in combinations of biochemically related antimetabolites," J. Biol. Chem., 208:477-488, (1954).
Falcone et al., "Rheological and cohesive properties of hyaluronic acid," J. Biomed. Mater. Res., Part A, 76A(4):721-728, (2005).
Fang, Ferric C., "Antimicrobial reactive oxygen and nitrogen species: concepts and controversies," Nat. Rev. Micro., 2(10):820-832, (2004).
Feliu, N. et al., "Stability and Biocompatibility of a Library of Polyester Dendrimers in Comparison to Polyamidoamine Dendrimers," Biomaterials., 33(7):1970-1981, (2012).
Fernández-Barat, L. et al., "Phenotypic shift in Pseudomonas aeruginosa populations from cystic fibrosis lungs after 2-week antipseudomonal treatment," J. Cyst. Fibros., 16:222-229, (2017).
Friedman et al., "The negative impact of antibiotic resistance," Clin. Microbiol. Infect., 22:416-422, (2016).
Frost, M.C. and Meyerhoff, M.E., "Synthesis, Characterization, and Controlled Nitric Oxide Release from S-Nitrosothiol-Derivatized Fumed Silica Polyme Filler Particles," J Biomed Mater Res Part A., 72A(4):409-419, (2005).
Fu, et al., "Preparation and reversible photo-crosslinking/photocleavage behavior o 4-methylcoumarin functionalized hyperbranched polyester," Polymer, 49(23): 4981-4988, (2008).
Gabor, G. and Vincze, A., "Determination of Thiols in Non-Aqueous Solutions," Anal Chim Acta., 92(2):429-431, (1977).

(56) References Cited

OTHER PUBLICATIONS

Gao and Koo, "Do catalytic nanoparticles offer an improved therapeutic strategy to combat dental biofilms?," Nanomed. Nanotech. Biol. Med., 12(4):275-279, (2017).

Gao and Yan, "Hyperbranched polymers: from synthesis to applications," Prog. Polym. Sci., 29(3):183-275, (2004).

Gao, Q, et al., "Synthesis and Characterization of Chitosan-Based Diazeniumdiolates [Abstract]," Polymer Materials Science and Engineering, 24(12):415-421, (2008).

Ghosh, S. & Lapara, T. M., "The effects of subtherapeutic antibiotic use in farm animals on the proliferation and persistence of antibiotic resistance among soil bacteria," ISME J., 1:191-203, (2007).

Gibney et al., "Poly(ethylene imine)s as antimicrobial agents with selective activity," Macromol. Biosci., 12(9):1279-1289, (2012).

Gombotz et al., "Protein release from alginate matrices," Advanced Drug Delivery Reviews, 31(3):267-285, (1998).

Grabowski et al., "Toxicity of surface-modified PLGA nanoparticles toward lung alveolar epithelial cells," International Journal of Pharmaceutics, 454:686-694, (2013).

Haggie, P., and Lueck, J.(Eds), "Agenda for Cystic Fibrosis Foundation Research Conference," Cystic Fibrosis Foundation, (2019), https://www.cff.org/Research/Researcher-Resources/Cystic-Fibrosis-Foundation-Research-Conference/.

Hall, J. R. et al., "Mode of nitric oxide delivery affects antibacterial action," ACS Biomater. Sci. Eng., acsbiomaterials.9b01384 (2019).

Hall-Stoodley et al., "Bacterial Biofilms: from the Natural Environment to Infectious Diseases," Nat. Rev. Micro., 2:95-108, (2004).

Harrison et al., "Development of an ex vivo porcine lung model for studying growth Virulence, And signaling of pseudomonas aeruginosa," Infect. Immun., 82:3312-3323, (2014).

Helander, I. M. & Mattila-Sandholm, T., "Fluorometric assessment of Gram-negative bacterial permeabilization," J. Appl. Microbiol., 88:213-219, (2000).

Hetrick and Schoenfisch, "Analytical chemistry of nitric oxide," Annu. Rev. Anal. Chem., 2:409-433, (2009).

Hetrick et al., "Anti-biofilm efficacy of nitric oxide-releasing silica nanoparticies," Biomaterials, 30:2782-2789, (2009).

Hetrick et al., "Bactericidal Efficacy of Nitric-Oxide Releasing Silica Nanoparticles," ACS Nano, 2(2):235-246, (2008).

Hopkins, Sean, "Development of high capacity hyperbranched nitric oxide donors for controlling subcutaneous inflammation," Open Access Dissertation, Michigan Technological University, 154 pages, (2015).

Hossain et al., "Discovery of Two Bacterial Nitric Oxide-Responsive Proteins and Their Roles in Bacterial Biofilm Regulation," Acc. Chem. Res., 50(7):1633-1639, (2017).

Howlin, R. P., et al., "Low-Dose Nitric Oxide as Targeted Anti-biofilm Adjunctive Therapy to Treat Chronic Pseudomonas aeruginosa Infection in Cystic Fibrosis," Mol. Ther., 25:2104-2116, (2017).

Hrabie, Joseph A., et al., "New nitric oxide-releasing zwitterions derived from polyamines," The Journal of Organic Chemistry, 58(6):1472-1476, (1993).

Hu et al., "A smart aminoglycoside hydrogel with tunable gel degradation, on-demand drug release, and high antibacterial activity," Journal of Controlled Release, 247:145-152, (2017).

Huang et al., "Nitric oxide-loaded echogenic liposomes for nitric oxide delivery and inhibition of intimal hyperplasia," J. Am. Coll. Cardiol., 54(7):652-659, (2009).

Huang et al., "Reduction-responsive multifunctional hyperbranched polyaminoglycosides with excellent antibacterial activity, biocompatibility and gene transfection capability," Biomaterials, 106:134-143, (2016).

Hussain et al., "Glucocorticoids can affect Pseudomonas aeruginosa (ATCC 27853) internalization and intracellular calcium concentration in cystic fibrosis bronchial epithelial cells," Experimental Lung Research, 41(7):383-392, (2015).

Imfeld, T. "Chewing gum—facts and fiction: a review of gum-chewing and oral health," Crit. Rev. Oral. Biol. Med., 10(3):405-419, (1999).

Jin et al., "Nitric Oxide-Releasing Cyclodextrins," Journal of the American Chemical Society, 140: 14178-14184 (2018).

Jin et al., "Biocompatible or biodegradable hyperbranched polymers: from self-assembly to cytomimetic applications," Chem. Soc. Rev., 41(18):5986-5997, (2012).

Jones et al., "Antimicrobial properties of nitric oxide and its application in antimicrobial formulations and medical devices," Appl. Microbiol. Biotechnol., 88(2):401-407, (2010).

Jones, C.G., "Chlorhexidine: is it still the gold standard?" Periodontology 2000, 15:55-62, (1997).

Kailasan et al., "Synthesis and characterization of thermoresponsive polyamidoamine-polyethylene glycol-poly (d, l-lactide) core-shell nanoparticies," Acta Biomater. 6(3):1131-1139, (2010).

Kaneko et al., "The transition metal gallium disrupts Pseudomonas aeruginosa iron metabolism and has antimicrobial and antibiofilm activity," The Journal of Clinical Investigations, 117(4):877-888, (2007).

Karatasos, K., "Self-Association and Complexation of the Anti-Cancer Drug Doxorubicin with PEGylated Hyperbranched Polyesters in an Aqueous Environment," J Phys Chem B., 117(8):2564-2575, (2013).

Kassebaum et al., "Global Burden of Untreated Caries: A Systematic Review and Metaregression," Journal of Dental Research, 94(5):650-658, (2015).

Keefer et al., "Chemistry of the Diazeniumdiolates I. Structural and Spectral Characteristics of the [N(O)NO]—Functional Group," Nitric Oxide, 5(4):377-394, (2001).

Keefer et al., "'NONOates' (1-Substituted Diazen- 1-ium-1,2-diolates) as Nitric Oxide Donors: Convenient Nitric Oxide Dosage Forms," Methods in Enzymology, 268:281-293, (1996).

Keefer, Larry K., "Fifty Years of Diazeniumdiolate Research. From Laboratory Curiosity to Broad-Spectrum Biomedical Advances," ACS Chemical Biology, 6(11):1147-1155, (2011).

Keefer, Larry K., "Nitric Oxide (NO)- and Nitroxyi (HNO)-Generating Diazeniumdiolates (NONOates): Emerging Commercial Opportunities," Current Topics in Medicinal Chemistry, 5(7):625-636, (2005).

Khalil et al., "Synergy between Polyethylenimine and Different Families of Antibiotics against a Resistant Clinical Isolate of Pseudomonas aeruginosa," Antimicrob. Agents Chemother., 52:1635-1641, (2008).

Khan et al., "Overcoming Drug Resistance with Alginate Oligosaccharides Able To Potentiate the Action of Selected Antibiotics," Antimicrobial Agents and Chemotherapy, 56(10):5134-5141, (2012).

Kim et al., "NONOates—polyethylenimine hydrogel for controlled nitric oxide release and cell proliferation modulation," Bioconjugate Chem., 22(6):1031-1038, (2011).

Knop et al., "Poly(ethylene glycol) in drug delivery: pros and cons as well as potential alternatives," Angew. Chem. Int. Ed., 49(36):6288-6308, (2010).

Konter, Joerg, et al., "Synthesis of Diazen-1-ium-1 , 2-diolates Monitored by the "NOtizer" Apparatus: Relationship between Formation Rates, Molecular Structure and the Release of Nitric Oxide," European Journal of Organic Chemistry, 2007(4): 616-624, (2007).

Kovach, K. et al., "Evolutionary adaptations of biofilms infecting cystic fibrosis lungs promote mechanical toughness by adjusting polysaccharide production," npj Biofilms Microbiomes, 3, (2017).

Kurniasih et al., "Dendritic nanocarriers based on hyperbranched polymers," Chem. Soc. Rev., 44(12):4145-4164, (2015).

Labena et al., "One-pot synthesize of dendritic hyperbranched PAMAM and assessment as a broad spectrum antimicrobial agent and anti-biofilm," Mater. Sci. Eng. C Mater. Biol. Appl., 58:1150-1159, (2016).

Lee et al., "Alginate: properties and biomedical applications," Prog Polym Sci., 37(1):106-126, (2012).

Lenoir et al., "Polyolefin matrixes with permanent antibacteriai activity: preparation, antibacterial activity, and action mode of the active species," Biomacromolecules, 7(8):2291-2296, (2006).

Liakos et al., "All-natural composite wound dressing films of essential oils encapsulated in sodium alginate with antimicrobial properties," International Journal of Pharmaceutics, 463(2):137-145, (2014).

(56) References Cited

OTHER PUBLICATIONS

Liu et al., "Hollow double-layered polymer microspheres with pH and thermo-responsive properties as nitric oxide-releasing reservoirs," Polym. Chem., 6(17):3305-3314, (2015).

Liu et al., "Synergistic supramolecular encapsulation of amphiphilic hyperbranched polymer to dyes," Macromolecules, 39(23):8102-8111, (2006).

Liu, T. et al., "Hollow Polymer Nanoparticies with S-Nitrosothiols as Scaffolds for Nitric Oxide Release," J Colloid Interface Sci., 459:115-122, (2015).

Loesche et al., "Role of Streptococcus mutans in Human Dental Decay," Microbiological Reviews, 50(4):353-380, (1986).

Lowe et al., "Storage and delivery of nitric oxide via diazeniumdiolated metal organic framework," Micropor. Mesopor. Mat., 181:17-22, (2013).

Lu et al., "Nitric oxide-releasing amphiphilic poly(amidoamine) (PAMAM) dendrimers as antibacterial agents," Biomacromolecules, 14(10):3589-3598, (2013).

Lu et al., "Nitric oxide-releasing chitosan oligosaccharides as antibacteriai agents," Biomaterials, 35(5):1716-1724, (2014).

Lu et al., "Structurally Diverse Nitric Oxide-Releasing Poly(propylene imine) Dendrimers," Chem. Mater., 23(18):4227-4233, (2011).

Lu, Y. et al., "Shape- and Nitric Oxide Flux-Dependent Bactericidal Activity of Nitric Oxide-Releasing Silica Nanorods," Small., 9(12):2189-2198, (2013).

Lu, Y. et al., "S-Nitrosothiol-Modified Nitric Oxide-Releasing Chitosan Oligosacccarides as Antibacterial Agents," Acta Biomater.,12:62-69, (2015).

Luo et al., "Nitric oxide: a newly discovered function on wound healing," Acta Pharmacol. Sin., 26(3):259-264, (2005).

Luo et al., "Poly (ethylene glycol)-conjugated PAMAM dendrimer for biocompatible, high-efficiency DNA delivery," Macromolecules, 35(9):356-3462, (2002).

Lutzke, A. et al., "Nitric Oxide-Releasing S-Nitrosated Derivatives of chitin and Chitosan for Biomedical Applications," J Mater Chem B., 2:7449-7458, (2014).

Lutzke, et al., "Nitric oxide release from a biodegradable cysteine-based polyphosphazene," Journal of Materials Chemistry B, 4(11): 1987-1988, (2016).

Machelart et al., "Intrinsic Antibacterial Activity of Nanoparticies Made of β-Cyclodextrins Potentiates Their Effect as Drug Nanocarriers against Tuberculosis", ACS Nano, 13: 3992-4007, (2019).

Macmicking et al., "Nitric oxide and macrophage function," Annu. Rev. Immunol, 15:323-350, (1997).

Madison, C.J., et al., "Gallium and Nitrite Have Synergistic Antimicrobial Activity," Cystic Fibrosis Conference: Scientific Session VIII: Novel Approaches for Treating Difficult Infections, Abstract, Jun. 26, 2019.

Malmström, E. et al., "Hyperbranched Aliphatic Polyesters," Macromoiecules, 28(5):1698-1703, (1995).

Maragos, Chris M., et al., "Complexes of. NO with nucleophiles as agents for the controlled biological release of nitric oxide. Vasorelaxant effects," Journal of Medicinal Chemistry, 34(11):3242-3247, (1991).

Martinez, J. L. & Baquero, F., "Mutation Frequencies and Antibiotic Resistance," Antimicrob. Agents Chemother., 44:1771-1777, (2000).

Matai et al., "Chemically Cross-Linked Hybrid Nanogels of Alginate and PAMAM Dendrimers as Efficient Anticancer Drug Delivery Vehicles," ACS Biomater. Sci. Eng., 2(2):213-223, (2016).

Mather et al., "Michael addition reactions in macromolecular design for emerging technologies," Prog. Polym. Sci., 31(5):487-531, (2006).

Mendelman, P. M. et al., "Aminoglycoside penetration, inactivation, and efficacy in cystic fibrosis sputum," Am. Rev. Respir. Dis., 132:761-765, (1985).

Miller et al., "Gaseous nitric oxide bactericidal activity retained during intermittent high-dose short duration exposure," Nitric Oxide, 20:16-23, (2009).

Miller et al., "Role of Oxidants in Microbial Pathophysiology," Clinical Microbiology Reviews, 10(1):1-18, (1997).

Miller, MR, and Megson, IL, "Recent developments in nitric oxide donor drugs," Br J Pharmacol.,151(3):305-321, (2007).

Minandri, F., "Promises and failures of gallium as an antibacterial agent," Future Microbiology, 9(3):379-397, (2014).

Moreno-Sastre et al., "Pulmonary delivery of tobramycin-loaded nanostructured lipid carriers for Pseudomonas aeruginosa infections associated with cystic fibrosis," International Journal of Pharmaceutics, 498:263-273, (2016).

Mourtzis et al., "Synthesis, characterization, and remarkable biological properties of cyclodextrins bearing guanidinoalkylamino and aminoalkylamino groups on their primary side,", Chem. Eur. J., 14: 4188-4200 (2008).

Mulani et al., "Emerging Strategies to Combat ESKAPE Pathogens in the Era of Antimicrobial Resistance: A Review," Front. Microbiol., 10, (2019).

Müller, L. et al., "Human airway mucus alters susceptibility of Pseudomonas aeruginosa biofilms to tobramycin, but not colistin," J. Antimicrob. Chemother., 73:2762-2769, (2018).

Nair et al., "Biodegradable polymers as biomaterials," Prog. Polym. Sci., 32(8-9):762-798, (2007).

Nakamoto, H. and Bardwell, J.C.A., "Catalysis of Disulfide Bond Formation and Isomerization in the Escherichia coli Periplasm," Biochim Biophys Acta., 1694(1-3):111-119, (2004).

Nguyen et al., "Co-delivery of nitric oxide and antibiotic using polymeric nanoparticles," Chem Sci., 7(2):1016-1027, (2016).

Nichols et al., "Local delivery of nitric oxide: Targeted delivery of therapeutics to bone and connective tissues," Adv. Drug Delivery Rev, 64(12):1177-1188, (2012).

Nordgard et al., "Alterations in Mucus Barrier Function and Matrix Structure Induced by Guluronate Oligomers," Biomacromolecules, 15:2294-2300, (2014).

Nordgard et al., "Oligosaccharides As Modulators of Rheology in Complex Mucous Systems," Biomacromolecules, 12(8):3084-3090, (2011).

O'Halloran, T.V. and Culotta, V.C., "Metallochaperones, an Intercellular Shuttle Service for Metal Ions," J Biol Chem., 275(33):25057-25060, (2000).

Ohwada, Tomohiko, et al., "7-Azabicyclo [2.2. 1] heptane as a structural motif to block mutagenicity of nitrosamines," Bioorganic & Medicinal Chemistry, 19(8): 2726-2741, (2011).

Park et al., "Nitric oxide integrated polyethylenimine-based triblock copolymer for efficient antibacterial activity," Biomaterials, 34(34):8766-8775, (2013).

Park et al., "Polydopamine Hollow Nanoparticle Functionalized with N-diazeniumdiolates as a Nitric Oxide Delivery Carrier for Antibacterial Therapy," Adv. Healthcare Mater., 5(16):2019-2024, (2016).

Parzuchowski et al., "Synthesis and characterization of polymethacrylate-based nitric oxide donors," J. Am. Chem. Soc., 124(41):12182-12191, (2002).

Paster et al., "The breadth of bacterial diversity in the human periodontal pocket and other oral sites," Periodontology 2000, 42:80-87, (2006).

Paul et al., "Chitosan and Alginate Wound Dressings: A Short Review," Trends Biomater. Artif. Organs, 18(1):18-23, (2004).

Paula and Koo, "Nanosized building blocks for customizing novel antibiofilm approaches," J. Dent. Res., 96(2):128-136, (2017).

Petersen et al., "The global burden of oral diseases and risks to oral health," Bull. World Health Organ., 83(9):661-669, (2005).

Piras et al., "S-Nitroso-Beta-Cyclodextrins as New Bimodal Carriers: Preparation, Detailed Characterization, Nitric-Oxide Release, and Molecular Encapsulation," Chemistry—An Asian Journal, 8:2768-2778 (2013).

Polizzi et al., "Water-Soluble Nitric Oxide-Releasing Gold Nanoparticles," Langmuir, 23:4938-4943, (2007).

Prabaharan, M. et al., "Amphiphilic Multi-Arm-Block Copolymer Conjugated with Doxorubicin via pH-Sensitive Hydrazone Bond for Tumor-Targeted Drug Delivery," Biomaterials., 30(29):5757-5766, (2009).

Pritchard et al., "A New Class of Safe Oligosaccharide Polymer Therapy To Modify the Mucus Barrier of Chronic Respiratory Disease," Molecular Pharmaceutics, 13(3):863-872, (2016).

(56) References Cited

OTHER PUBLICATIONS

Privett et al., "Examination of Bacterial Resistance to Exogenous Nitric Oxide," Nitric Oxide, 26:169-173, (2012).
Privett, B. J., et al., "Synergy of nitric oxide and silver sulfadiazine against gram-negative, gram-positive, and antibiotic-resistant pathogens," Mol. Pharm., 7:2289-2296, (2010).
Product Overiew, "AR-501 (Gallium Citrate): Novel anti-infective for the growing problem of antibiotic resistance," Aridis Pharmaceuticals, (Last accessed Aug. 13, 2020), https://www.aridispharma.com/ar-501/.
Product Overview, "Ardis Pipeline: Blood Stream Infections : Product Candidates," Aridis Pharmaceuticals, (Last accessed Aug. 13, 2020), https://www.aridispharma.com/product-overview/.
PubChem CID 6032, "Kanamycin A," PubChem, NCBI, pp. 1-9, (2005).
Radvar et al., "Comparison of 3 periodontal local antibiotic therapies in persistent periodontal pockets," J. Periodontol., 67(9):860-865, (1996).
Ragheb, M. N. et al. "Inhibiting the Evolution of Antibiotic Resistance," Mol. Cell, 73:157-165.e5, (2019).
Rees et al., "Role of endothelium-derived nitric oxide in the regulation of blood pressure," Proc. Natl. Acad. Sci., 86(9):3375-3378, (1989).
Reighard et al., "Disruption and eradication of P. aeruginosa biofilms using nitric oxide-releasing chitosan oligosaccharides," Biofouling, 31:775-787, (2015).
Reighard, K. P. & Schoenfisch, M. H., "Antibacterial action of nitric oxide-releasing chitosan oligosaccharides against Pseudomonas aeruginosa under aerobic and anaerobic conditions," Antimicrob. Agents Chemother., 59:6506-6513, (2015).
Riccio and Schoenfisch, "Nitric oxide release: part I. Macromolecular scaffolds," Chem. Soc. Rev., 41(10):3731-3741, (2012).
Riccio, D.A. et al., "Photoinitiated Nitric Oxide-Releasing Tertiary S-Nitrosothiol-Modified Xerogels," ACS Appl Mater Interfaces., 4(2):796-804, (2012).
Riccio, D.A. et al., "Stöber Synthesis of Nitric Oxide-Releasing S-Nitrosothiol-Modified Silica Particles," Chem Mater., 23(7):1727-1735, (2011).
Robson, Martin C., "Wound Infection: A Failure of Wound Healing Caused by an Imbalance of Bacteria," Surgical Clinics of North America, 77(3):637-650, (1997).
Rouillard, K. R., et al., "Exogenous Nitric Oxide Improves Antibiotic Susceptibility in Resistant Bacteria," Research Presentation: Univ. of North of Carolina Chapel Hill, (2019).
Roy, B. et al., New Thionitrates: Synthesis, Stability, and Nitric Oxide Generation, J Org Chem., 59(23):7019-7026, (1994).
Safdar et al., "Targeted diazeniumdiolates: Localized nitric oxide release from glioma-specific peptides and proteins," Int. J. Pharm., 422(1-2):264-270, (2012).
Santjit, S. & Indrawattana, N., "Mechanisms of Antimicrobial Resistance in ESKAPE Pathogens," Biomed Res. Int., 2016:1-8, (2016).
Schaffer et al., "Nitric oxide regulates wound healing," J. Surg. Res., 63(1):237-240, (1996).
Schairer et al., "The potential of nitric oxide releasing therapies as antimicrobial agents," Virulence, 3:271-279, (2012).
Schomburg et al., "Preparation, Purification, and Analysis of Alkylated Cyclodextrins," J. High Res. Chromatog., 15:579-584, (1992).
Seabra, A.B. et al., "Antibacterial Nitric Oxide-Releasing Polyester for the Coating of Blood-Contacting Artificial Materials," Artif Organs, 34(7):E204-14, (2010).
Sen et al., "Periodontal Disease and Recurrent Vascular Events in Stroke/TIA Patients," J. Stroke Cerebrovasc Dis., 22(8):1420-1427, (2013).
Shah et al., "Synthesis of S-nitrosoglutathione-alginate for prolonged delivery of nitric oxide in intestines," Drug Deliv., 23(8):2927-2935, (2016).
Shin et al., "Inorganic/Organic Hybrid Silica Nanoparticles as a Nitric Oxide Delivery Scaffold," Chem. Mater., 20:239-249, (2008).
Shishido, S.M. and Oliveira, M.G., "Polyethylene Glycol Matrix Reduces the Rates of Photochemical and Thermal Release of Nitric Oxide from S-Nitroso-N-Acetylcysteine," Photochem Photobiol., 71(3):273-80, (2000).
Singh et al., "Biotechnological applications of cyclodextrins," Biotechnol. Adv., 20:341-359, (2002).
Singh, Simrat Pal, et al., "Rice Nicotianamine Synthase 2 expression improves dietary iron and zinc levels in wheat," Theoretical and Applied Genetics, 130(2): 283-292, (2017).
Slomberg, D.L. et al., "Role of Size and Shape on Biofilm Eradication for Nitric Oxide-releasing Silica," ACS Appl. Mater. Interfaces, 5(19):9322-9329, (2013).
Slots et al., "Antibiotics in periodontal therapy: advantages and disadvantages," J. Clin. Periodontol., 17(7 (Pt2)):479-493, (1990).
Solleti et al., "Antimicrobial properties of liposomal azithromycin for Pseudomonas infections in cystic fibrosis patients," J Antibicrob Chemother, 70:784-796, (2015).
Soto et al., "Design Considerations for Silica-Particle-Doped Nitric-Oxide-Releasing Polyurethane Glucose Biosensor Membranes," ACS Sensors, 2(1):140-150, (2017).
Soto et al., "Functionalized Mesoporous Silica via an Aminosilane Surfactant Ion Exchange Reaction: Controlled Scaffold Design and Nitric Oxide Release," ACS Appl. Mater. Interfaces, 8(3):2220-2231, (2016).
Southerland et al., "Periodontitis and diabetes associations with measures of atherosclerosis and CHD," Atherosclerosis, 222(1):196-201, (2012).
Spellberg, B., et al., "The Epidemic of Antibiotic-Resistant Infections: A Call to Action for the Medical Community from the Infectious Diseases Society of America," Clin. Infect. Dis., 46:155-164, (2008).
Stasko and Schoenfisch, "Dendrimers as a Scaffold for Nitric Oxide Release," J. Am. Chem. Soc., 128(25):8265-8271, (2006).
Stasko et al., "Cytotoxicity of polypropylenimine dendrimer conjugates on cultured endothelial cells," Biomacromolecules, 8(12):3853-3859, (2007).
Stasko, N.A. et al., "S-Nitrosothiol-Modified Dendrimers as Nitric Oxide Delivery Vehicles," Biomacromolecules, 9(3):834-841, (2008).
Suchyta and Schoenfisch, "Controlled release of nitric oxide from liposomes," ACS Biomater. Sci. Eng., 3(9):2136-2143, (2017).
Sun et al., "Nitric Oxide-Releasing Dendrimers as Antibacterial Agents," Biomacromolecules, 13(10):3343-3354, (2012).
Tomalia et al., "A New Class of Polymers: Starburst-Dendritic," Polym. J. 17:117-132, (1985).
Valko, M. et al., "Metals, Toxicity and Oxidative Stress," Curr Med Chem., 12(10):1161-1208, (2005).
Van Strydonck et al., "Plaque inhibition of two commercially available chlorhexidine mouthrinses," J. Clin. Periodontol., 32(3):305-309, (2005).
Vizitiu et al., "Binding of phosphates to aminocyclodextrin biomimetics," J. Org. Chem., 64(17):6235-6238, (1999).
Voit and Lederer, "Hyperbranched and highly branched polymer architectures—synthetic strategies and major characterization aspects," Chem. Rev., 109(11):5924-5973, (2009).
Wan, A., et al., "Characterization of folate-graft-chitosan as a scaffold for nitric oxide release," International Journal of Biological Macromolecules, Elsevier B.V. 43:415-421, (2008).
Wan, A., et al., "Effects of Molecular Weight and Degree of Acetylation on the Release of Nitric Oxide from Chitosan—Nitric Oxide Adducts," Journal of Applied Polymer Science, Wiley Periodicals, Inc., 117:2183-2188, (2010).
Wang et al., "Synthesis and applications of stimuli-responsive hyperbranched polymers," Prog. Polym. Sci., 64:114-153, (2017).
Wang et al., "Synthesis and gene delivery of poly(amido amine)s with different branched architecture," Biomacromolecules, 11 (2):489-495, (2010).
Wang et al., "Bioapplications of hyperbranched polymers," Chemical Society Reviews, 44(12):4023-4071, (2015).
Wang et al., "Synthesis and evaluation of phenylalanine-modified hyperbranched poly (amido amine) s as promising gene carriers," Biomacromolecules, 11(1):241-251, (2009).

(56) References Cited

OTHER PUBLICATIONS

Wang et al., "The effect of a branched architecture on the antimicrobial activity of poly(sulfone amines) and poly(sulfone amine)/silver nanocomposites" J. Mater. Chem., 22:15227-15234, (2012).
Wang, J. and Xu, Tongwen, "Facile Construction of Muitivalent Targeted Drug Delivery System from Boltom® Series Hyperbranched Aliphatic Polyester an Folic Acid," Poly Adv Technol., 22:763-767, (2009).
Williams, D.L.H., "S-Nitrosation and the Reactions of S-Nitroso Compounds," Chem Soc Rev., 14(2):171-196, (1985).
Williams, D.L.H., "The Chemistry of S-Nitrosothiols," Acc Chem Res., 32(10):869-876, (1999).
Wink et al., "DNA deaminating ability and genotoxicity of nitric oxide and its progenitors," Science, 254(5034):1001-1003, (1991).
Wo et al., "Recent advances in thromboresistant and antimicrobial polymers for biomedical applications: just say yes to nitric oxide (NO)," Biomater. Sci., 4(8):1161-1183, (2016).
Wold et al., "Fabrication of Biodegradable Polymeric Nanofibers with Covalently Attached NO Donors," ACS Appl. Mater. Interfaces, 4(6):3022-3030, (2012).
Worley et al., "Anti-Biofilm Efficacy of Dual-Action Nitric Oxide-Releasing Alkyl Chain Modified Poly(amidoamine) Dendrimers," Mol. Pharmaceutics, 12:1573-1583, (2015).
Worley et al., "Nitric Oxide-Releasing Quaternary Ammonium-Modified Poly(amidoamine) Dendrimers as Dual Action Antibacterial Agents," Bioconjugate Chem., 25(5):918-927, (2014).
Wu et al., "'Living' controlled in situ gelling systems: thiol-disulfide exchange method toward tailor-made biodegradable hydrogels," J. Am. Chem. Soc., 132(43):15140-15143, (2010).
Xiao, Y.L. et al., "Multifunctional Unimolecular Micelles for cancer—Targeted Drug Delivery and Positron Emission Tomography Imaging," Biomaterials, 33(11):3071-3082, (2012).
Xu et al., "Well-defined poly (2-hydroxyl-3-(2-hydroxyethylamino) propyl methacrylate) vectors with low toxicity and high gene transfection efficiency," Biomacromolecules, 11(6):1437-1442, (2010).
Yang et al., "S-Nitrosothiol-modified hyperbranched polyesters," Polym. Chem., 7(46):7161-7169, (2016).
Yapor, J.P. et al., "Biodegradabie Citrate-Based Polyesters with S-Nitrosothiol Functional Groups for Nitric Oxide Release," J Mater Chem B., 3(48):9233-9241, (2015).
Žagar, E. and Žigon, M., "Aliphatic Hyperbranched Polyesters Based on 2,2-bis(methylol)propionic Acid—Determination of Structure, Solution and Bulk Properties," Prog Polymer Sci., 36(1):53-88, (2011).
Zambon, Joseph J., "Actinobacillus actinomycetemcomitans in human periodontal disease," Journal of Clinical Periodontology, 12(1):1-20, (1985).
Zamboulis et al: "Polyglycerol Hyperbranched Polyesters: Synthesis, Properties and Pharmaceutical and Biomedical Applications," International Journal of Molecular Sciences, 20(24):6210, (2019).
Zeng, X.H. et al., "Endocytic Uptake and Intracellular Trafficking of Bis-MPA-Based Hyperbranched Copolymer Micelles in Breast Cancer Cells," Biomacromolecules, 13(11):3814-3822, (2012).
Zhai, X. et al., "Amphiphilic Dendritic Molecules: Hyperbranched Polyesters with Alkyl-Terminated Branches," Macromolecules, 36(9):3101-3110, (2003).
Zhang et al., "Nitric oxide-releasing fumed silica particles: synthesis, characterization, and biomedical application," J. Am. Chem. Soc., 125(17):5015-5024, (2003).
Zhang et al., "A physical gel made from hyperbranched polymer gelator," Chem. Commun., 25:2587-2589, (2007).
Zhang et al., "Antibacterial cotton fabric grafted with silver nanoparticles and its excellent laundering durability," Carbohydr. Polym., 92(2):2088-2094, (2013).
Zhang et al., "Synthesis of an amino-terminated hyperbranched polymer and its application in reactive dyeing on cotton as a salt-free dyeing auxiliary," Color. Technol., 123(6):351-357, (2007).
Zhang et al., "The antimicrobial activity of the cotton fabric grafted with an amino-terminated hyperbranched polymer," Cellulose, 16:281-288, (2009).

Zhang, H. et al., "Hyperbranched Polyester Hydrogels with Controlled Drug Release and Cell Adhesion Properties," Biomacromolecules, 14(5):1299-1310, (2013).
Zhang, X.F. et al., "Nitric Oxide Delivery by Core/Shell Superparamagnetic Nanoparticle Vehicles with Enhanced Biocompatibility," Langmuir., 28(35):12879-12885, (2012).
Zheng et al., "Hyperbranched polymers: Advances from synthesis to applications," Chemical Society Reviews, 44(12):4091-4130, (2015).
Zhong, Yong-Li, et al., "Scalable Synthesis of Diazeniumdiolates: Application to the Preparation of MK-8150," Organic letters, 21(11):4210-4214, (2019).
Zhou et al., "Polymethacrylate-Based Nitric Oxide Donors with Pendant N-Diazeniumdiolated Alkyldiamine Moieties: Synthesis, Characterization, and Preparation of Nitric Oxide Releasing Polymeric Coatings," Biomacromolecules, 6:780-789, (2005).
Zhou et al., "Water-soluble poly (ethyieniminej-based nitric oxide donors: preparation, characterization, and potential application in hemodialysis," Biomacromolecules, 7(9):2565-2574, (2006).
Zhu et al., "Influence of Branching Architecture on Polymer Properties," Journal of Polymer Science Part B: Polymer Physics, 49(18):1277-1286, (2011).
European Application No. 18775628.3, Extended European Search Report dated Sep. 28, 2020.
European Application No. 18812540.5, Communication pursuant to Rules 161(1) and 162 EPC, dated Jul. 8, 2020.
European Search Report and Search Opinon dated August 3, 2020 by the European Search Authority for EP Application No. 18736471.6 (8 pages).
European Search Report dated May 4, 2020 by the European Search Authority for EP Application No. 17859196.2 (32 pages).
Supplementary European Search Report dated Feb. 5, 2016 in EP Application No. 13829755.1.
U.S. Appl. No. 16/459,015, Requirement for Restriction/Election dated Oct. 9, 2019.
U.S. Appl. No. 16/725,566, Non-Final Office Action dated Jun. 10, 2021.
WIPO Application No. PCT/IB2018/050051, PCT International Search Report and Written Opinion of the International Searching Authority dated Jun. 8, 2018.
WIPO Application No. PCT/ B2018/052144, PCT International Search Report and Written Opinion of the International Searching Authority dated Aug. 8, 2018.
WIPO Application No. PCT/US2013/055360, PCT International Search Report and Written Opinion of the International Searching Authority dated Dec. 23, 2013.
WIPO Application No. PCT/US2017/055371, PCT International Preliminary Report on Patentability dated Apr. 9, 2019.
WIPO Application No. PCT/US2017/055371, PCT International Search Report and Written Opinion of the International Searching Authority dated Dec. 28, 2017.
WIPO Application No. PCT/US2018/061061, PCT International Search Report and Written Opinion of the International Searching Authority dated Apr. 5, 2019.
WIPO Application No. PCT/US2019/021051, PCT International Search Report and Written Opinion of the International Searching Authority dated Jun. 21, 2019.
WIPO Application No. PCT/US2019/068412, Invitation to Pay Additional Fees dated Feb. 21, 2020.
WIPO Application No. PCT/US2019/068412, PCT International Search Report and Written Opinion of the International Searching Authority dated May 21, 2020.
Hopkins, Sean, "Development of High Capacity Hyperbranched Nitric Oxide Donors for Controlling Subcutaneous Inflammation," Access Dissertation, Michigan Technological University, (2015).
Yang, Lei et al., "Antibacterial Activity of Nitric Oxide-Releasing Hyperbranched Polyamidoamines," Bioconjugate Chem., 29:35-43, (2018).
Chinese Application No. 2018800 80277.6, First Office Action, dated Sep. 3, 2021.
WIPO Application No. PCT/US2019/068412, PCT International Preliminary Report on Patentability dated Jul. 8, 2021.
Newton, David E., Chemistry of New Materials, Shanghai Science and Technology Literature Press, p. 184, (Jul. 31, 2008).

(56) References Cited

OTHER PUBLICATIONS

Smith et al., "Nitric Oxide-Releasing Polymers Containing the AN(O)NoU-Group," Journal of Medicinal Chemistry, 39:1148-1157, (Jan. 1996).
Australian Application 2018205823, Examination Report No. 1 for standard patent application dated Sep. 15, 2021.
JP Application No. 2019-556425, Notice of Reasons for Refusal dated Oct. 26, 2021.
EP Application No. 19763961.0, Extended European Search Report dated Nov. 19, 2021.
EP Application No. 18812540.5, Communication Pursuant to Article 94(3) dated Oct. 14, 2021.

* cited by examiner

NITRIC OXIDE-RELEASING ALGINATES AS BIODEGRADABLE ANTIBACTERIAL SCAFFOLDS AND METHODS PERTAINING THERETO

INCORPORATION BY REFERENCE OF ANY PRIORITY APPLICATIONS

This patent application is a divisional of U.S. application Ser. No. 16/475,615, filed Jul. 2, 2019, which is a 371 National Stage entry of International Application No. PCT/IB2018/050051 with an international filing date of Jan. 3, 2018, which claims the benefit of priority to U.S. Provisional Patent Application Nos. 62/441,742 and 62/483,505, filed Jan. 3, 2017 and Apr. 10, 2017, respectively, which are hereby incorporated by reference in their entireties for all purposes.

GOVERNMENT INTEREST

This invention was made with government support under AI112029 awarded by The National Institutes of Health. The Government has certain rights in the invention.

FIELD

The presently disclosed subject matter relates generally to nitric oxide-releasing alginate polymers which are covalently modified to store and release nitric oxide in a controlled manner. Additionally disclosed are methods of synthesis and use of the alginate polymers as antibacterial agents.

BACKGROUND

Bacterial infections pose a great challenge to human health in community and hospital settings. Several chronic infections, such as those associated with implanted devices, chronic wounds, and cystic fibrosis are frequently caused by biofilm-forming pathogens such as *Pseudomonas aeruginosa* and *Staphylococcus aureus*. Biofilms are cooperative communities of bacteria encapsulated by an exopolysaccharide (EPS) matrix protecting the bacteria from host immune response and antibiotics. It has been reported that eradication of biofilms may require up 1000 times higher antibiotic concentrations relative to those needed for planktonic bacteria. Several factors contribute to the observed antibacterial resistance of biofilms, including slower bacterial metabolism, limited diffusion of the antibacterial agent within the EPS matrix, and altered microenvironments (e.g., regions of nutrient depletion).

SUMMARY

Because of the resistance of biofilms to conventional antibacterials, new antibacterial agents that can effectively penetrate and eradicate biofilm-based bacterial colonies are greatly needed. Such agents, and methods for making the same, and their use in decreasing and/or eliminating microbial load are provided for herein.

Nitric oxide (NO) plays a variety of physiological roles as a signaling molecule and, as disclosed herein, can also play significant roles in pathophysiology, for example as a therapeutic agent. NO use as a therapeutic has heretofore been underused, based at least in part on limited NO payloads of therapeutic compositions, NO release rates that are more rapid than desired, and the lack of targeted NO delivery.

Provided herein are NO-releasing scaffolds, methods of producing such scaffolds, and methods of treating various pathophysiologies using such scaffolds that leverage the enhanced NO-release characteristics and harness the abundant potential of NO-releasing pharmacological potential. In particular, provided herein are compounds that are highly efficacious as antimicrobials.

In several embodiments, there are provided a functionalized alginate comprising one or more covalently modified monomers of Formula I

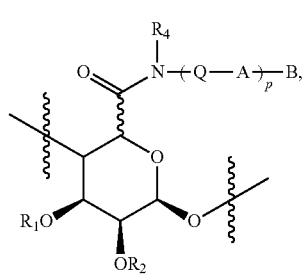

wherein, at least one monomer of Formula I contains a nitric oxide donor. In several embodiments, $R_1$ and $R_2$ are each independently selected from hydrogen, $C_{1-5}$ alkyl (C=O)—, and $C_{1-5}$ alkyl, or combinations thereof. In several embodiments, $R_3$ is hydrogen or $C_{1-5}$ alkyl. In several embodiments, $R_4$ is, in each instance that $R_4$ is present, hydrogen or $C_{1-5}$ alkyl. In several embodiments, Q is —$(CR_aR_b)_v$—, with $R_a$ and $R_b$ independently being hydrogen or $C_{1-5}$ alkyl, and v being an integer ranging from 2 to 6. In several embodiments, A has the following structure (or variants thereof):

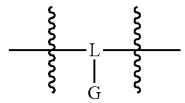

wherein, L is S, O, or N. In several embodiments, G, in each instance, is hydrogen, is taken together with L to form a nitric oxide donor, or, depending on the embodiment is absent. In several embodiments, p is an integer ranging from 1 to 10. In several embodiments, B is selected from the group consisting of hydrogen, —Y—Z, and $C_{1-5}$ alkyl. Depending on the embodiment, the $C_{1-5}$ alkyl is optionally substituted with amino, hydroxyl, nitrile, $CO_2H$, mono($C_{1-6}$)alkylamino-, di($C_{1-6}$)alkylamino-, —(CO)$NR^cR^d$ or —$NR^c(CO)R^d$. Combinations of these substitutions in the $C_{1-5}$ alkyl can be used in the compound, depending on the embodiment. In several embodiments, $R^c$ and $R^d$ are each independently selected from the group consisting of hydrogen and $C_{1-6}$ alkyl. In several embodiments, Y has one of the following structures:

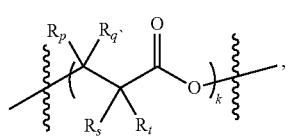

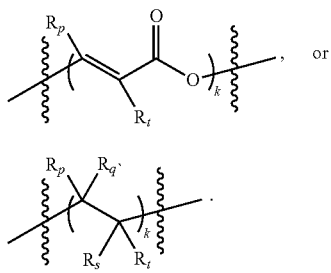

ii or

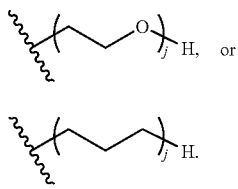

iii

In several embodiments, $R_p$, $R_q$, $R_s$ and $R_t$, in each instance, are independently, hydrogen or hydroxyl. Combinations of the structure for Y can be used in the compound, depending on the embodiment. In several embodiments, k is an integer ranging 1 to 20. In several embodiments, Z has one of the following structures:

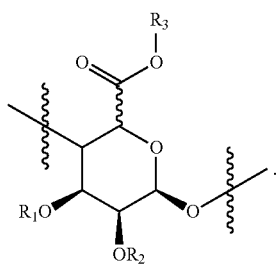

iv or v

In several embodiments, j, in each instance, is an integer ranging from 1 to 100.

In several embodiments, the functionalized alginate further comprises at least one monomer of Formula II.

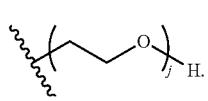

In several embodiments, the nitric oxide donor is diazeniumdiolate, nitrosothiol, a nitrosamine, a hydroxyl nitrosamine, a hydroxyl amine, or a hydroxyurea. In several embodiments, combinations of nitric oxide donors are used. In several embodiments, the nitric oxide generated by the functionalized alginate can optionally be supplemented with one or more additional sources of nitric oxide (either exogenous or endogenous, such as additional compound that enhances endogenous nitric oxide formation). In several embodiments, the functionalized alginate employs diazeniumdiolate as the nitric oxide donor. In several embodiments, the functionalized alginate is formulated such that $R_1$ and $R_2$ are hydrogen or $C_{1-5}$ alkyl, $R_3$ is hydrogen and $R_4$ is, in each instance, hydrogen or $C_{1-5}$ alkyl. In several embodiments, the functionalized alginate is formulated such that $R_1$, $R_2$, $R_3$, and $R_4$ are hydrogen. In several embodiments, the functionalized alginate is formulated such that v is 2 or 3, L is N, p is 1, 2, or 3. In several embodiments, the functionalized alginate is formulated such that B is —Y—Z. In several embodiments, the functionalized alginate is formulated such that Y has the structure:

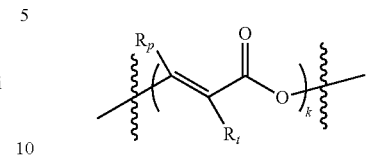

ii

In several embodiments, the functionalized alginate is formulated such that Z has the structure:

iv

In several embodiments, the functionalized alginate is formulated such that B is selected from the group consisting of hydrogen and $C_{1-5}$ alkyl, wherein the $C_{1-6}$alkyl is optionally substituted with amino, hydroxyl, nitrile, $CO_2H$, mono ($C_{1-6}$)alkylamino-, di($C_{1-6}$)alkylamino-, —(CO)NR$^c$R$^d$ or —NR$^c$(CO)R$^d$, and R$^c$ and R$^d$ are each independently selected from the group consisting of hydrogen and $C_{1-6}$ alkyl. In several embodiments, B is hydrogen or unsubstituted $C_{1-5}$ alkyl. In several embodiments, B is hydrogen or $C_3$ alkyl. In several embodiments, the functionalized alginate is formulated such that -(Q-A-)$_p$-B has the structure:

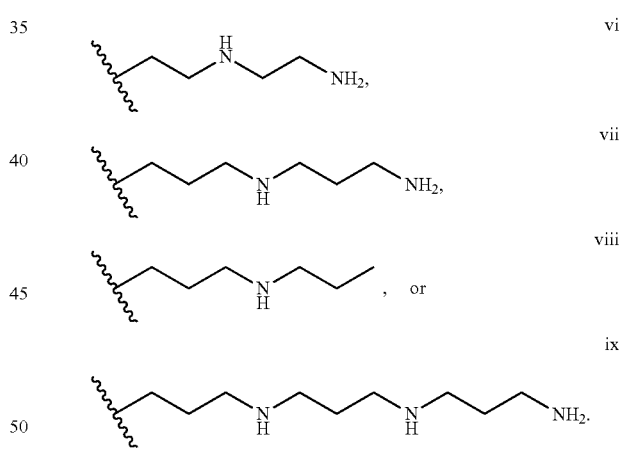

In several embodiments, G is taken together with a nitrogen in structure vi, vii, viii, or ix to form a nitric oxide donor. As discussed above, depending on the embodiment the nitric oxide donor can vary. In several embodiments, the nitric oxide donor is diazeniumdiolate.

In several embodiments, the functionalized alginate is formulated such that -(Q-A-)$_p$-B has the structure:

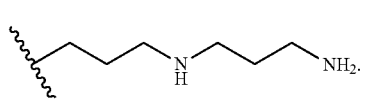

vii

In several embodiments, G is taken together with a nitrogen in structure vii to form a nitric oxide donor.

There is also provided a functionalized alginate comprising one or more covalently modified monomers of Formula I

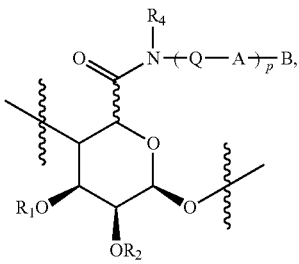

I and optionally, at least one monomer of Formula II'

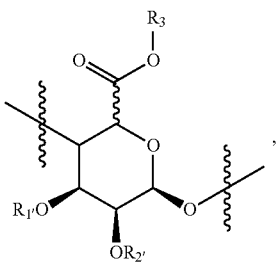

, wherein at least one monomer of Formula I contains a nitric oxide donor. In several embodiments, $R_1$, $R_{1'}$, $R_2$, $R_{2'}$, $R_3$, and $R_4$ are each independently selected from the group consisting of hydrogen, $-((CH_2)_nO)_m-H$, $-(((CH_2)_nO)_m-(CH_2)_o H$, and $C_{1-5}$ alkyl, where m, n, and o are independently an integer from 0 to 6. In several embodiments, Q is $-(CR_aR_b)_v-$. In several embodiments, $R_a$ and $R_b$ are independently hydrogen. In several embodiments, v is an integer from 2 to 6. In several embodiments, A is

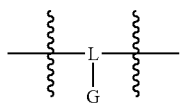

where L is S, O, or N. In several embodiments, G, in each instance, is hydrogen, is taken together with L to form a nitric oxide donor, or is absent. In several embodiments, the nitric oxide donor, where present, is selected from:

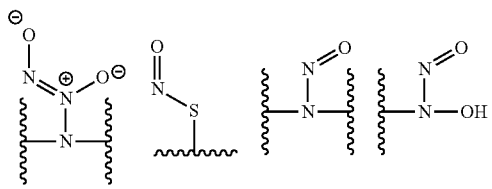

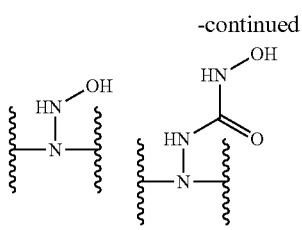

In several embodiments, p is an integer from 1 to 10. In several embodiments, B is absent or is selected from the group consisting of hydrogen, $-Y-Z$, and $C_{1-5}$ alkyl, wherein the $C_{1-5}$ alkyl is optionally substituted with amino, hydroxyl, nitrile, $CO_2H$, mono($C_{1-6}$)alkylamino-, di($C_{1-6}$)alkylamino-, $-(CO)NR^cR^d$ or $-NR^c(CO)R^d$. In several embodiments, $R^c$ and $R^d$ are each independently selected from the group consisting of hydrogen and $C_{1-6}$ alkyl. In several embodiments, Y has a structure of:

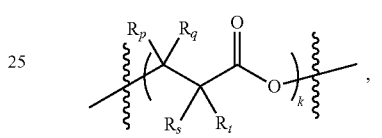

i

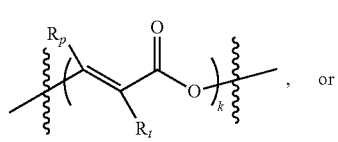

ii

, or

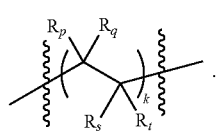

iii

.

In several embodiments, $R_p$, $R_q$, $R_s$ and $R_t$, in each instance, are independently, hydrogen or hydroxyl. In several embodiments, k is an integer from 1 to 20. In several embodiments, Z has a structure of:

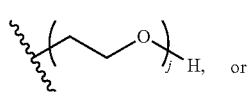

iv

, or

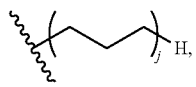

v

, wherein j, in each instance, is an integer from 1 to 100.

In several embodiments,

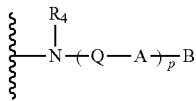

has a structure selected from one or more of the following:

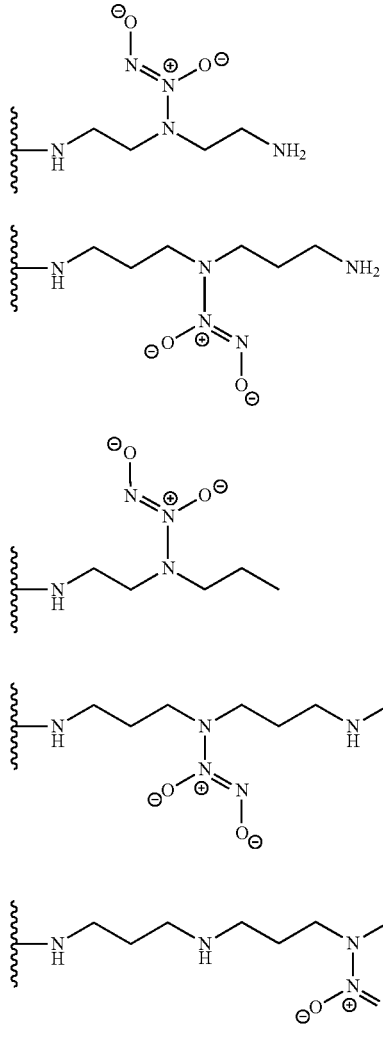

In several embodiments,

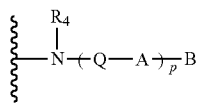

has a structure selected from one or more of the following:

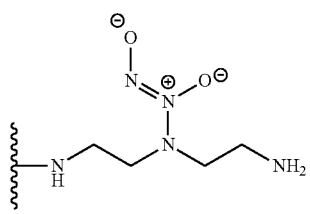

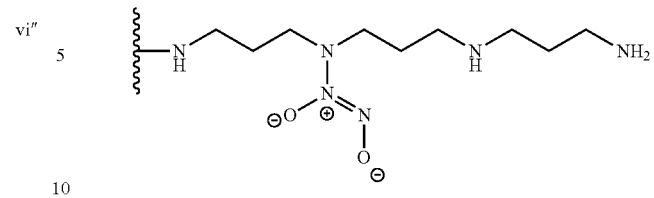

In several embodiments, $R_1$, $R_{1'}$, $R_2$, $R_{2'}$, $R_3$, and $R_4$ are hydrogen.

In several embodiments, the functionalized alginate is water soluble. In several embodiments, the functionalized alginate has a total releasable nitric oxide storage in a range of 0.1-1.0 μmol of NO per milligram of the functionalized alginate, including about 0.1-0.3 μmol/mg, 0.3-0.5 μmol/mg, 0.5-0.7 μmol/mg, 0.7-0.9 μmol/mg, 0.9-1.0 μmol/mg, and any storage amount therebetween, including endpoints. In several embodiments, the NO-release has a half-life in the range of 0.1-24 hour, including about 0.1 to about 0.5 hours, about 0.5 to about 1 hour, about 1 to about 2 hours, about 2 to about 4 hours, about 4 to about 6 hours, about 6 to about 10 hours, about 10 to about 15 hours about 15 to about 20 hours, and about 20 to about 24 hours, including any time therebetween, including endpoints. In several embodiments, the total duration of NO release is in the range of 1-60 hours, including about 1 to about 5 hours, about 5 to about 10 hours, about 10 to about 15 hours, about 15 to about 20 hours, about 20 to about 30 hours, about 30 to about 50 hours, or about 50 to about 60 hours, and any time therebetween, including endpoints. In several embodiments, these NO release characteristics are particularly advantageous because they allow delivery of efficacious quantities of NO to a desired target site, for time periods that allow for reduction in microbial load (among other beneficial effects). This is particularly advantageous given the known short half-life of NO, which, absent the technology disclosed herein, limits the utility of NO. In several embodiments, the total NO release after 4 hours is in the range between 0.1-1.0 μmol of NO per milligram of the functionalized alginate. In several embodiments, the compounds disclosed herein are particularly advantageous because they allow for the delivery of higher concentrations of NO to a target site as compared to other methods of delivering NO. For example, in several embodiments, the compounds (and methods of their use) result in an NO concentration of between about 10 and 500 μM at a target site, including about 10 to about 20 μM, 20 to about 50 μM, 50 to about 100 μM, 100 to about 150 μM, 150 to about 200 μM, 200 to about 250 μM, 250 to about 300 μM, 300 to about 350 μM, 350 to about 400 μM, 400 to about 450 μM, 450 to about 500 μM, and any concentration in between those listed, including endpoints. In several embodiments, these concentrations are maintained for times that exceed those achieved by other NO delivery methods. For example, in several embodiments, a microbicidal concentration of NO is maintained for about 1 hour, about 2 hours, about 4 hours, about 8 hours, about 12 hours, about 18 hours, or about 24 hours (or any time therebetween, including endpoints).

In several embodiments, 15% or more of the monomers in the functionalized alginate are monomers of Formula I. In several embodiments, the functionalized alginate has a molecular weight in the range of 1-600 kDa. In several embodiments, the functionalized alginate has two or more different covalently modified monomers of Formula I.

There is also provided for herein, in several embodiments, a compound for microbial reduction comprising a nitric oxide (NO) releasing water-soluble functionalized alginate, the functionalized alginate comprising an amine-containing group covalently bound to at least a repeat unit of the alginate, wherein the amine-containing group comprises an NO donor, wherein the NO donor generates NO and induces oxidative and/or nitrosative damage to microbial DNA and membrane structures, thereby reducing microbial load. In several embodiments, at least 15% of the repeat units in the compound are monomers of Formula I. In several embodiments, the compound optionally further comprises at least one repeat unit of Formula II'. In several embodiments, the compound does not result in the formation of nitrosamine.

Also provided for herein is a dual action compound for the decrease of microbial load and reduction of mucus viscoelasticity comprising a water-soluble functionalized alginate comprising an amine-containing group coupled to at least one repeat unit of the alginate, wherein the amine-containing group comprises an NO donor that generates NO, wherein the NO induces damage to microbial DNA and membrane structures, thereby reducing microbial load, and wherein the NO disrupts mucin-mucin interactions in a mucus layer, thereby decreasing mucus viscoelasticity. In several embodiments, the disulfide-reducing reactivity of NO is responsible, at least in part, for reducing mucus viscosity. In several embodiments, the reduced mucus viscosity can enhance the efficacy of subsequent NO treatments and/or increase the ability of a subject's innate immune system to further control microbial loads. In several embodiments, the dual action compound does not result in the formation of nitrosamine.

There is also provided for herein, in several embodiments, a compound for microbial reduction comprising a water-soluble nitric oxide (NO) releasing scaffold comprising an amine-containing group coupled to the scaffold, wherein the amine-containing group comprises an NO donor, wherein the NO donor generates NO and induces oxidative and/or nitrosative damage to microbial DNA and membrane structures, thereby reducing microbial load. In several embodiments, the scaffold comprises a biopolymer. In several embodiments, the biopolymer is chitosan, alginate, or hyaluronic acid, among others disclosed herein. In some embodiments, the water-soluble nitric oxide (NO) releasing scaffold does not comprise and/or lacks chitosan or hyaluronic acid. In some embodiments, the water-soluble nitric oxide (NO) releasing scaffold does not comprise and/or lacks a dendrimer. In some embodiments, the water-soluble nitric oxide (NO) releasing scaffold does not comprise and/or lacks polyamidoamine or polyurethane. In several embodiments, the nitric oxide releasing scaffold does not result in the formation of nitrosamine Also provided for herein, in several embodiments, are pharmaceutical formulations comprising any of the functionalized NO-releasing alginates disclosed herein and a pharmaceutically acceptable excipient.

Methods for preparing functionalized alginates as disclosed herein are also provided. For example, in several embodiments, the method comprises contacting an amine of Formula III

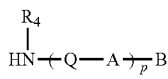

III with an alginate in the presence of a peptide coupling reagent, to form a modified monomer of Formula I

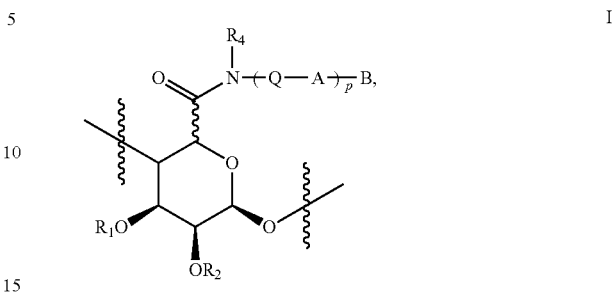

I and contacting the alginate containing the covalently modified monomer of Formula I with a nitric oxide source to form a functionalized alginate as described above. In several embodiments, $R_1$, $R_2$, $R_4$, Q, A, B and/or p are as described above. In several embodiments, $R_1$ and $R_2$ are hydrogen or $C_{1-5}$ alkyl, $R_3$ is hydrogen or $C_{1-5}$ alkyl, $R_4$ is, in each instance, hydrogen or $C_{1-5}$ alkyl, v is 2 or 3, L is N, and p is an integer from 1 to 3. In several embodiments, $-(Q-A-)_p-B$ has the structure:

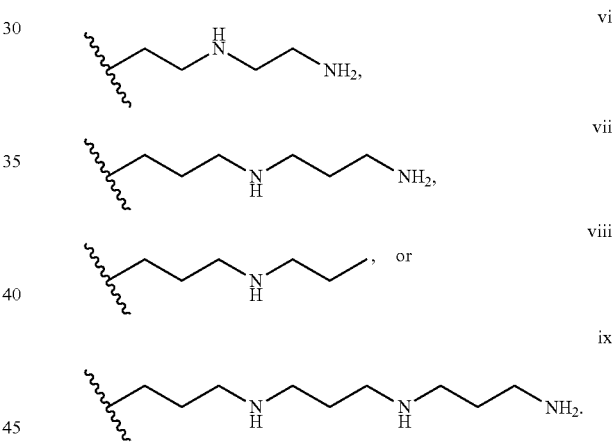

In several embodiments, G is taken together with a nitrogen to form a nitric oxide donor. In several embodiments, the method comprises using diazeniumdiolate as the nitric oxide donor. In several embodiments, the resulting functionalized alginate is water-soluble.

Also provided herein are methods for delivering nitric oxide to a subject, comprising administering an effective amount of any of the functionalized alginates disclosed herein to the subject. Methods of treating a disease state are also provided for herein, the methods comprising, in several embodiments administering an effective amount of any of the functionalized alginates disclosed herein to a subject in need of treatment, wherein the disease state is selected from the group consisting of a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases. In several embodiments, the disease state is a microbial infection. In several embodiments, the disease state is cystic fibrosis.

There is also provided for herein the use of a compound in the preparation of a medicament for treatment of cystic fibrosis, the compound comprising a water-soluble functionalized alginate comprising an amine-containing group coupled to at least one repeat unit of the alginate, wherein the amine-containing group comprises an NO donor that generates NO, wherein the NO induces damage to microbial DNA and membrane structures, thereby reducing microbial load, wherein the NO disrupts mucin-mucin interactions in a mucus layer, thereby decreasing mucus viscoelasticity, and wherein the decreased mucus viscoelasticity allows for improved lung clearance of microbes. In several embodiments, the compound is formulated for delivery to the lungs of a subject having cystic fibrosis. In several embodiments, the compound is formulated for delivery at least twice daily to a subject having cystic fibrosis.

In several embodiments, there is provided for herein a method of reducing microbial load on a surface comprising applying a compound to a surface contaminated with a plurality of microbes wherein the compound comprises a nitric oxide (NO) releasing water-soluble functionalized alginate, the functionalized alginate comprising an amine-containing group covalently bound to at least a repeat unit of the alginate, wherein the amine-containing group comprises an NO donor, wherein the NO donor generates NO and induces oxidative and/or nitrosative damage to microbial DNA and membrane structures, thereby reducing microbial load, and wherein the plurality of microbes comprises two or more of the following: gram-positive bacteria, gram-negative bacteria, fungi, yeast, and viruses. In several embodiments, the surface is an organic surface. In several embodiments, the surface is human skin. In several embodiments, application of the compound does not induce skin irritation. In several embodiments, the surface is animal skin. In several embodiments, application of the compound does not induce skin irritation. In several embodiments, the surface is human airway tissue. In several embodiments, application of the compound (e.g., inhalation) does not induce irritation of airway epithelial cells. In several embodiments, the surface is an inorganic surface. In several embodiments, the inorganic surface is an external or internal surface of a medical device. In several embodiments, the application of the compound generates an anti-microbial coating on the external or internal surface of the medical device. In several embodiments, the medical device comprises an endoscope.

In several embodiments, the microbial load to be reduced and/or eliminated comprises drug-resistant bacteria. In several embodiments, the drug-resistant bacteria comprise carbapenem-resistant Enterobacteriaceae. In several embodiments, the drug-resistant bacteria comprise Methicillin-resistant *Staphylococcus aureus*. In several embodiments, the microbe comprises human immunodeficiency virus, herpes simplex virus, papilloma virus, parainfluenza virus, influenza, hepatitis, Coxsackie Virus, herpes zoster, measles, mumps, rubella, rabies, pneumonia, hemorrhagic viral fevers, H1N1, and the like), prions, parasites, fungi, mold, yeast and bacteria (both gram-positive and gram-negative) including, among others, *Candida albicans, Aspergillus niger, Escherichia coli* (*E. coli*), *Pseudomonas aeruginosa* (*P. aeruginosa*), and *Staphylococcus aureus* (*S. aureus*), Group A streptococci, *S. pneumoniae, Mycobacterium tuberculosis, Campylobacter jejuni, Salmonella, Shigella*, and a variety of drug resistant bacteria. The terms microorganism and microbe shall be used interchangeably. Microbes can include wild-type, genetically-engineered or modified organisms. In several embodiments, the formulations and methods disclosed herein are for topical use or treatment of a surface.

In several embodiments, there is provided a method of treating a microbial infection comprising, contacting a surface contaminated with a plurality of microbes with a compound comprising a nitric oxide (NO) releasing water-soluble functionalized alginate, the functionalized alginate comprising an amine-containing group covalently bound to at least a repeat unit of the alginate, wherein the amine-containing group comprises an NO donor, wherein the NO donor generates NO and induces damage to the membrane and/or DNA of the microbes, thereby reducing the number of viable microbes and treating the infection, and wherein the plurality of microbes comprises one or more of viruses, gram positive bacteria, gram negative bacteria, drug resistant bacteria, molds, yeasts, fungi, and combinations thereof.

In several embodiments, there is provided a method of reducing the viscoelasticity of a mucus layer, comprising contacting a surface a comprising a mucus layer with a compound comprising a nitric oxide releasing water-soluble functionalized alginate, the functionalized alginate comprising an amine-containing group covalently bound to at least a repeat unit of the alginate, wherein the amine-containing group comprises a nitric oxide donor, wherein the nitric oxide donor generates nitric oxide and wherein the nitric oxide disrupts mucin-mucin interactions in the mucus layer, thereby decreasing mucus viscoelasticity. In several embodiments, the mucus layer results from the presence of a plurality of microbes. In several embodiments, the microbes comprise *Staphylococcus aureus*. In several embodiments, the microbes comprise *Pseudomonas aeruginosa*. In several embodiments, the microbes comprise *Burkholderia cepacia*. In several embodiments, the microbes contribute to development of cystic fibrosis. In several embodiments, the methods further comprise contacting the mucus layer with an antimicrobial. In several embodiments, the antimicrobial is amoxicillin. In several embodiments, the antimicrobial is cefdinir. In several embodiments, the antimicrobial is tetracycline.

Depending on the embodiment, the methods and uses employ compounds disclosed herein that are formulated for administration via a topical route, via injection, via ingestion, or via inhalation. In several embodiments, the route is inhalation (e.g., through an inhaler) and the methods and uses of the No-releasing compound are for the treatment of cystic fibrosis.

In some embodiments, the subject matter disclosed herein is directed to functionalized high molecular weight alginates having small molecule polyamines that can be modified with N-diazeniumdiolate NO donors to produce NO-releasing biopolymers capable of diverse and tunable release kinetics. At least one structural unit in the alginate backbone contains the structural unit of Formula I.

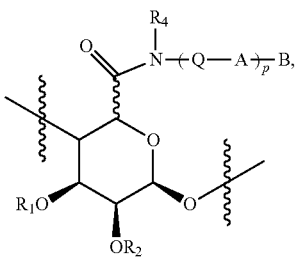

I

Optionally, at least one structural unit of the alginate further comprises the structural unit of Formula II and/or the structural unit of Formula II'.

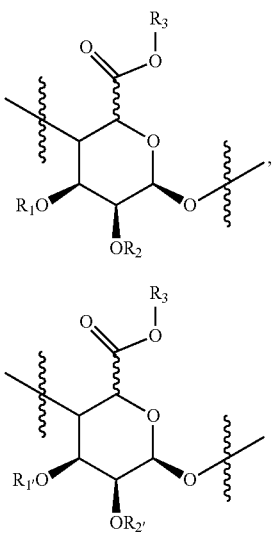

II

,

II'

Advantageously, in some embodiments, the alginates described herein are water soluble, tunable with respect to NO storage and NO-release kinetics, and/or capable of delivering NO to a target.

In some embodiments, the subject matter disclosed herein is directed to methods of preparing an alginate comprising at least one structural unit of Formula I and/or, optionally, at least one structural unit of Formula II.

In some embodiments, the subject matter disclosed herein is directed to methods of delivering and/or releasing NO to a subject. In some embodiments, the methods comprise administering to a subject an alginate comprising at least one structural unit of Formula I and/or, optionally, at least one structural unit of Formula II.

In some embodiments, the subject matter disclosed herein is directed to methods of treating a disease state in a subject. In some embodiments, the method comprises administering to a subject an alginate comprising at least one structural unit of Formula I and/or, optionally, at least one structural unit of Formula II.

In some embodiments, the subject matter disclosed herein is directed to a pharmaceutical composition comprising an alginate containing at least one structural unit of Formula I and/or, optionally, at least one structural unit of Formula II and one or more pharmaceutically acceptable excipients.

In some embodiments, the subject matter disclosed herein is directed to a method of disrupting, eradicating and/or preventing a biofilm by employing an alginate comprising at least one structural unit of Formula I and/or, optionally, at least one structural unit of Formula II.

In several embodiments described herein, NO is released and/or generated from any of the nitric-oxide releasing scaffolds. In other embodiments, one or more of NO, NO+ and NO− are released and/or generated from any of the nitric-oxide releasing scaffolds.

BRIEF DESCRIPTION OF THE FIGURES

(FIG. 1B) a plot of total NO release vs time.

FIG. 2A shows the bactericidal efficacy for embodiments of NO-releasing alginate materials at 8 mg/mL concentrations. FIG. 2B shows the bactericidal efficacy of embodiments of fast NO-releasing alginates at their respective minimum biofilm eradication concentration at 24 hours (MBEC24h).

DETAILED DESCRIPTION

Figure 1A:
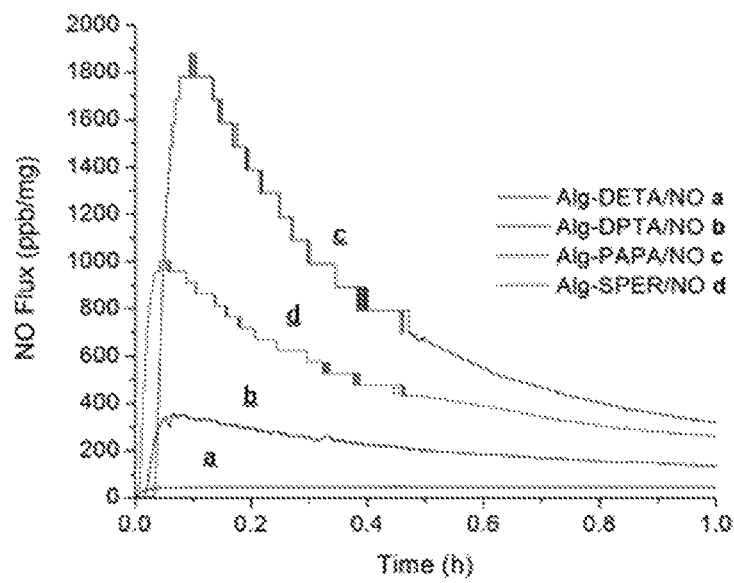
FIGS. 1A and 1B show (FIG. 1A) real time NO-release profiles for the first 1 hour from an embodiment of a NO-releasing alginate.

New antibacterial agents are needed, and nitric oxide (NO) is an endogenously produced, broad-spectrum antibacterial agent capable of eradicating both planktonic bacteria and biofilms, primarily through the formation of reactive NO byproducts (e.g., peroxynitrite and dinitrogen trioxide) that cause oxidative and nitrosative damage to microbial DNA and membrane structures. The wide range of mechanisms by which NO exerts its antibacterial effects makes it unlikely that bacteria will foster resistance. However, the difficulties associated with delivering gaseous NO necessitate the use of molecular NO donors capable of storing and releasing NO under specific environmental conditions. In particular, N-diazeniumdiolate NO donors have garnered interest for applications in controlled NO delivery owing to their spontaneous, proton-initiated NO release in physiological conditions. The NO-release kinetics can be tuned based on several parameters, e.g. pH, temperature, and the chemical structure of the precursor amine as described herein. Although low molecular weight N-diazeniumdiolate NO donors have been extensively utilized as therapeutics, indirect NO delivery to a specific site of action and off-target toxicity remains an issue. Thus, there is a need for the development of macromolecular NO-release scaffolds as alternative delivery agents that can be tuned to control and localize NO release at the site of interest (e.g., dendrimers, silica nanoparticles).

Some embodiments pertain to high molecular weight alginates chemically modified to store and release nitric oxide (NO). In some embodiments, alginate carboxylic acid moieties are first modified with a series of small molecule amine groups using coupling chemistry (e.g., carbodiimide chemistry). In some embodiments, the coupling reaction results in an alginate comprising secondary amines. In some embodiments, the secondary amines are reacted with pressurized NO gas to form N-diazeniumdiolate NO donors. In some embodiments, the resulting NO-releasing macromolecular alginates described herein have a range of NO release (μmol NO-mg-1) properties. In some embodiments, the resulting NO-releasing macromolecular alginates have diverse NO-release kinetics (e.g., $t_{1/2}$). In some embodiments, the release kinetics of the alginates is dependent on the precursor amine structure.

Biomacromolecules such as chitosan, cellulose, etc. represent potential NO donor scaffolds due to their low toxicity and biodegradability. However, high molecular weight biomacromolecules based on polymers such as PLGA and chitosan have low water solubility and low nitric oxide loading. In some embodiments, the presently disclosed nitric oxide (NO) releasing alginates are advantageously biodegradable, water soluble, and/or tunable with respect to NO loading, storage, and release. In some embodiments, one or more of these properties contribute to the usefulness of the presently disclosed alginates in therapeutics and/or in treating disease states where water soluble therapeutics are advantageous, for example, in the treatment of bacteria. According to some embodiments, some advantages over known NO releasing particles that the presently disclosed functionalized NO releasing alginates possess include, but are not limited to, one or more of the following:

1) Efficient and unique synthesis routes and resultant chemical composition generated, in several embodiments, by contacting amine-containing chains with non-functionalized alginates;
2) the NO storage and NO-release kinetics of the generated nitric-oxide releasing scaffolds can be tuned for a particular application. This tuning is achieved, in several embodiments, by altering the type and/or number of functionalized monomers of e.g., Formula I. In several embodiments, additional functionalization of the amines in the generated nitric-oxide releasing scaffolds, for example, by compounds of different hydrophobicity/hydrophilicity further enables the control over NO-release kinetics. Indeed, excellent NO storage was observed by the presently disclosed functionalized alginates;
3) In contrast to particles, the functionalized alginates described herein are water soluble, facilitating a wider range of applications including biomedical application where water-solubility is desired. It is believed that NO-releasing chitosans are not water soluble. Thus, in several embodiments, the presently disclosed water soluble functionalized alginates can readily penetrate and eradicate biofilms; and
4) Reduced generation of byproducts or compounds that can have adverse effects. For example, the presence of nitrosamine was not observed in the UV-vis spectra for any of the NO releasing alginates disclosed and/or tested herein, even after 24 h of NO-release in PBS pH 7.4. Accordingly, in some embodiments, the formation of nitrosamine is not detectable by UV-vis spectra prior to or after substantial NO release. Nitrosamine has been linked to the formation of cancer in animals.

In some embodiments, the secondary amine group directly influences the stability of the N-diazeniumdiolate, allowing for control over both NO storage and release kinetics. The antibacterial efficacy of NO-releasing materials is dependent on both NO payloads and associated release kinetics. Disclosed herein is the bactericidal efficacy of the alginates with respect to NO-release kinetics, total NO storage, and amine structure.

The subject matter described herein can be embodied in different forms and should not be construed as limited to the embodiments set forth herein. Rather, these embodiments are provided for illustration and so that this disclosure will be thorough and complete, and will convey the scope of the subject matter to those skilled in the art. For example, features illustrated with respect to one embodiment can be incorporated into other embodiments, and features illustrated with respect to a particular embodiment can be deleted to provide another embodiment. In addition, numerous variations and additions to the embodiments suggested herein are contemplated herein in light of the instant disclosure, which do not depart from the instant subject matter.

Unless otherwise defined, all technical and scientific terms used herein have the same meaning as commonly understood by one of ordinary skill in the art to which this subject matter belongs. The terminology used in the description of the subject matter herein is for the purpose of describing particular embodiments only and is not intended to be limiting of the subject matter.

As used herein, "a," "an," or "the" can mean one or more than one. For example, "a" NO releasing moiety can mean a single or a multiplicity.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of the current subject matter, dose, time, temperature, and the like, is meant to encompass variations of ±20%, ±10%, ±5%, ±1%, ±0.5%, or even ±0.1% of the specified amount.

The term "effective amount," as used herein, refers to that amount of a functionalized alginate that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, an effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In some embodiments, an improvement in a condition can be a reduction in infection. In some embodiments, an improvement can be reduction of bacterial load (e.g., bioburden) on a surface or in a subject). In some embodiments, reduction in the thickness, production or other characteristic of a mucus layer is an improvement. Actual dosage levels of active ingredients in an active composition of the presently disclosed subject matter can be varied so as to administer an amount of the active compound(s) that is effective to achieve the desired response for a particular subject and/or application. The selected dosage level will depend upon a variety of factors including the activity of the composition, formulation, route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of an effective dose, as well as evaluation of when and how to make such adjustments, are contemplated herein.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

The terms "disrupting" and "eradicating" refer to the ability of the presently disclosed functionalized alginates to combat biofilms. The biofilms may be partially eradicated or disrupted, meaning that the cells no longer attach to one another or to a surface. The biofilm may be completely eradicated, meaning that the biofilm is no longer an interconnected, cohesive or continuous network of cells to a substantial degree. Depending in the embodiment, the biofilm (or bacteria) is reduced by at least about 20%, about 30%, about 40%, about 50% about 60% or more. In several embodiments, the biofilm is substantially eradicated, such that the biofilm is no longer capable of, for example, creating an environment (e.g., a local environment) that causes exhibition of symptoms of an infection.

As used herein, the term "water soluble" means that the alginate is capable of being dissolved in water. In some embodiments, water soluble functionalized alginates disclosed herein are soluble such that >20 mg of functionalized alginate dissolves per mL of water. In some embodiments, water soluble functionalized alginates disclosed herein are soluble such that >50 mg of functionalized alginate dissolves per mL of water. In some embodiments, water soluble functionalized alginates disclosed herein are soluble such that >75 mg of functionalized alginate dissolves per mL of water. In some embodiments, water soluble functionalized alginates disclosed herein are soluble such that >100 mg of functionalized alginate dissolves per mL of water. In some embodiments, the water soluble functionalized alginates disclosed herein are ones that are soluble in water to a concentration of greater than or equal to about: 10 mg/mL, 20 mg/mL 50 mg/mL, 75 mg/mL, 100 mg/mL, or ranges including and/or spanning the aforementioned values.

As used herein, the term "high molecular weight" means that the polymer has a molecular weight >10 kDa. Particularly useful alginates are polymers that can range in size from between 10 kDa to 1000 kDa, 50 kDa to 800 kDa, 200 kDa to 600 kDa, or 300 kDa to 400 kDa. In some embodiments, "high molecular weight" polymers are those having a molecular weight greater than or equal to about: 10 kDa, 50 kDa, 200 kDa, 300 kDa, 400 kDa, 600 kDa, 800 kDa, 1000 kDa, or ranges including and/or spanning the aforementioned values.

The terms "nitric oxide donor" or "NO donor" refer to species that donate, release and/or directly or indirectly transfer a nitric oxide species, and/or stimulate the endogenous production of nitric oxide in vivo and/or elevate endogenous levels of nitric oxide in vivo such that the biological activity of the nitric oxide species is expressed at the intended site of action.

The term "nitric oxide releasing" refers to species that donate, release and/or directly or indirectly transfer any one (or two or more) of the three redox forms of nitrogen monoxide (NO+, NO−, NO) and/or methods of donating, releasing and/or directly or indirectly transferring any one (or two or more) of the three redox forms of nitrogen monoxide (NO+, NO−, NO). In some embodiments, the nitric oxide releasing is accomplished such that the biological activity of the nitrogen monoxide species is expressed at the intended site of action.

The term "microbial infection" as used herein refers to bacterial, fungal, viral, yeast infections, as well other microorganisms, and combinations thereof.

The "patient" or "subject" treated in the many embodiments disclosed herein is, in some embodiments, a human patient, although it is to be understood that the principles of the presently disclosed subject matter indicate that the presently disclosed subject matter is effective with respect to all vertebrate species, including mammals, which are intended to be included in the terms "subject" and "patient." Suitable subjects are generally mammalian subjects. The subject matter described herein finds use in research as well as veterinary and medical applications. The term "mammal" as used herein includes, but is not limited to, humans, non-human primates, cattle, sheep, goats, pigs, horses, cats, dog, rabbits, rodents (e.g., rats or mice), monkeys, etc. Human subjects include neonates, infants, juveniles, adults and geriatric subjects.

In some embodiments, the subject can be a subject in need of the methods disclosed herein can be a subject that is experiencing a disease state and/or is anticipated to experience a disease state, and the methods and compositions of the subject matter described herein are used for therapeutic and/or prophylactic treatment.

As used herein, the term "functionalized alginate" refers to alginate polymers which contain one or more covalently modified monomer. Such "functionalized alginates" may or may not have a nitric oxide donor moiety attached. "Covalently modified monomer", as used herein, refers to a monomer which is an analog or derivative of a mannuronic acid and/or guluronic acid monomer. The term "monomer" refers to a single unit, which may or may not be joined with other sugars to form, for example, an alginate. The term monomer, thus, includes monomeric units (e.g., repeat units) in a polymer chain. Non-limiting examples of a monomer are guluronic acid and mannuronic acid.

Alginate is a naturally occurring anionic polymer harvested from algal sources and is composed of 1,4-linked α-1-guluronic acid (G) and β-d-mannuronic acid (M) units.

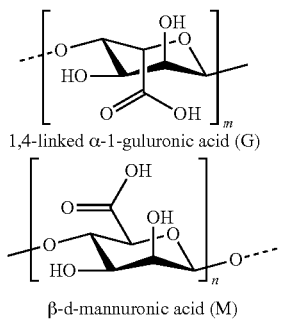

1,4-linked α-1-guluronic acid (G)

β-d-mannuronic acid (M)

Alginate is a biopolymer that maintains its water solubility even at high molecular weights (including those over >200 kDa). Advantageously, the functionalized alginates disclosed herein are water soluble. In some embodiments, the functionalized alginates disclosed herein have a solubility of 100 mg/mL or greater, as disclosed elsewhere herein. Alginate has been used in numerous biomedical applications, including as wound dressings, drug delivery vehicles, and mucin modifiers for cystic fibrosis, etc. Alginate may be chemically modified using the hydroxyl and carboxylic acid functional groups. An advantageous feature of useful alginates is an available carboxylic acid on the carbohydrate backbone that is derivatized according to the methods described herein to form a NO-releasing alginate.

As disclosed elsewhere herein, some embodiments pertain to a functionalized alginate. In some embodiments, the functionalized alginate comprises one or more covalently modified monomers of Formula I

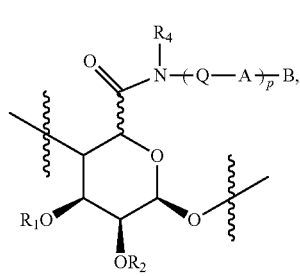

and optionally, at least one monomer of Formula II and/or optionally, at least one monomer of Formula II':

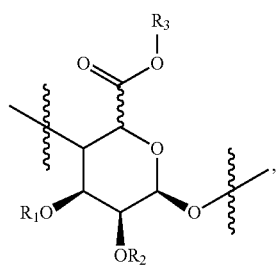

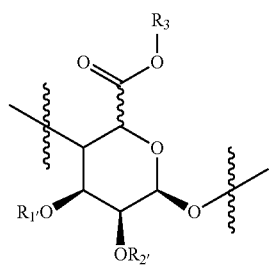

wherein, $R_1$, $R_1'$, $R_2$ and $R_2'$, in each instance, are each independently selected from the group consisting of hydrogen, $C_{1-5}$ alkyl(C=O)—, and $C_{1-5}$ alkyl;

$R_3$ is, in each instance, hydrogen or $C_{1-5}$ alkyl;

$R_4$ is, in each instance, hydrogen or $C_{1-5}$ alkyl;

Q is $—(CR_aR_b)_v—$;

wherein $R_a$ and $R_b$ are independently hydrogen or $C_{1-5}$ alkyl; and v is an integer from 2 to 6;

A is

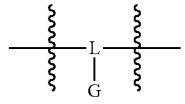

wherein, L is S, O, or N; and

G, in each instance, is hydrogen, is taken together with L to form a nitric oxide donor, or is absent;

p is an integer from 1 to 10;

B is selected from the group consisting of hydrogen, —Y—Z, and $C_{1-5}$ alkyl, wherein the $C_{1-5}$ alkyl is optionally substituted with amino, hydroxyl, nitrile, $CO_2H$, mono($C_{1-6}$)alkylamino-, di($C_{1-6}$)alkylamino-, —(CO)$NR^cR^d$ or —$NR^c$(CO)$R^d$, or B is absent;

wherein $R^c$ and $R^d$ are each independently selected from the group consisting of hydrogen and $C_{1-6}$ alkyl, wherein Y has a structure of:

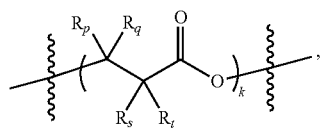

i

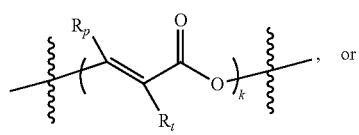

, or

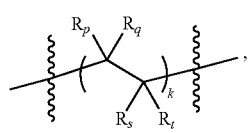

iii wherein $R_p$, $R_q$, $R_s$ and $R_t$, in each instance, are independently, hydrogen or hydroxyl; and k is an integer from 1 to 20; and Z has a structure of:

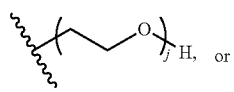

iv

, or

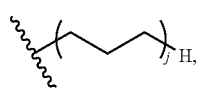

v wherein j, in each instance, is an integer from 1 to 100; and wherein at least one monomer of Formula I contains a nitric oxide donor.

In several embodiments, a functionalized alginate wherein the nitric oxide donor is selected from the group consisting of a diazeniumdiolate, nitrosothiol, a nitrosamine, a hydroxyl nitrosamine, a hydroxyl amine, a hydroxyurea, and a combination thereof. In some embodiments, the nitric oxide donors (e.g., G taken together with L) can be depicted structurally as:

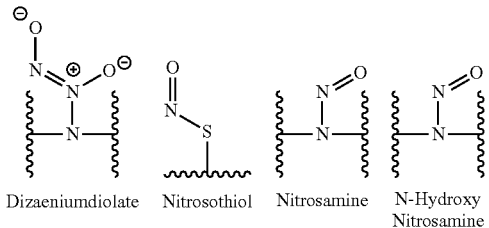

Diazeniumdiolate   Nitrosothiol   Nitrosamine   N-Hydroxy Nitrosamine

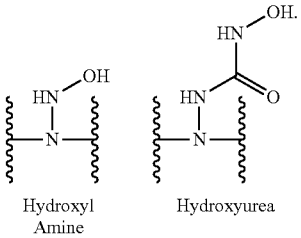

Hydroxyl Amine     Hydroxyurea

In some embodiments, the nitric oxide donor is diazeniumdiolate.

In some embodiments, $R_1$, $R_{1'}$, $R_2$ and $R_{2'}$ are hydrogen or $C_{1-5}$ alkyl;

$R_3$ is hydrogen; and/or $R_4$ is, in each instance, hydrogen or $C_{1-5}$ alkyl.

In some embodiments, $R_1$, $R_{1'}$, $R_2$, $R_{2'}$, $R_3$, and $R_4$ are hydrogen.

In some embodiments, $R_1$, $R_{1'}$, $R_2$, $R_{2'}$, $R_3$, and $R_4$ are each independently selected from the group consisting of hydrogen, —(($CH_2$)$_n$O)$_m$—H, —((($CH_2$)$_n$O)$_m$—($CH_2$)$_o$H and $C_{1-5}$ alkyl. In some embodiments, m, n, and o are independently an integer from 0 to 10. In some embodiments, m, n, and o are independently an integer from 0 to 6. In some embodiments, n is 2.

In some embodiments, v is 2 or 3;

L is N; and/or p is an integer from 1 to 3.

In some embodiments, B is —Y—Z.

In some embodiments, Y has the structure:

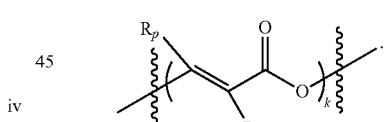

ii

In some embodiments, Z has the structure:

iv

In some embodiments, B is selected from the group consisting of hydrogen and $C_{1-5}$ alkyl, wherein the $C_{1-5}$ alkyl is optionally substituted with amino, hydroxyl, nitrile, $CO_2H$, mono($C_{1-6}$)alkylamino-, di($C_{1-6}$)alkylamino-, —(CO)$NR^cR^d$ or —$NR^c$(CO)$R^d$, wherein $R^c$ and $R^d$ are each independently selected from the group consisting of hydrogen and $C_{1-6}$ alkyl.

In some embodiments, B is hydrogen or unsubstituted $C_{1-5}$ alkyl.

In some embodiments, B is hydrogen or $C_3$ alkyl.

In some embodiments, in each instance, -(Q-A-)$_p$-B has the can comprise one or more of the following structures:

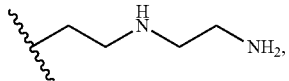
vi

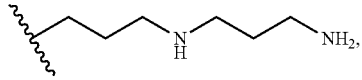
vii

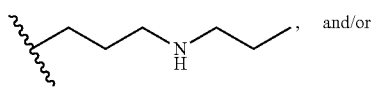
viii
, and/or

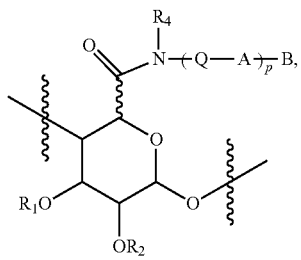
ix

In some embodiments, G is taken together with a nitrogen in structure vi, vii, viii, or ix to form a nitric oxide donor (e.g., by replacing an amine H in one or more of vi, vii, viii, or ix with G to provide an L-G).

In some embodiments, the nitric oxide donor is diazeniumdiolate.

In some embodiments, -(Q-A-)$_p$-B has the structure:

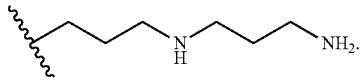
vii

In some embodiments, G is taken together with a nitrogen in structure vii to form a nitric oxide donor.

In some embodiments, the nitric oxide donor is diazeniumdiolate.

In some embodiments, the functionalized alginate comprises one or more covalently modified monomers of Formula Ia:

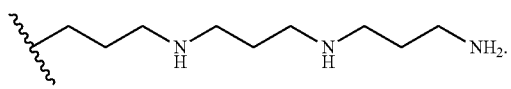
Ia and optionally, at least one monomer of Formula II'a:

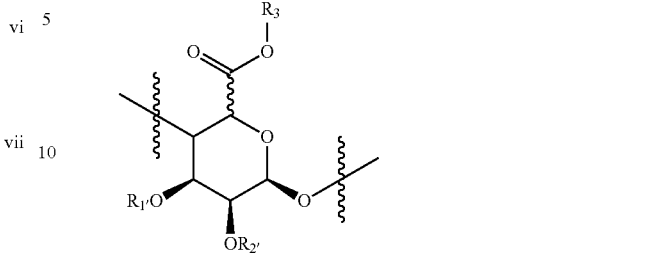
II'a where $R_1$, $R_{1'}$, $R_2$, $R_{2'}$, $R_3$, $R_4$, and -(Q-A-)$_p$-B are as defined elsewhere herein.

In some embodiments, the functionalized alginate comprises one or more covalently modified monomers of Formula I, Ia, II, II', and/or IIa, where $R_1$, $R_{1'}$, $R_2$, $R_{2'}$, $R_3$, $R_4$, and -(Q-A-)$_p$-B are as defined elsewhere herein.

In some embodiments, -(Q-A-)$_p$-B, has a structure selected from one or more of the following:

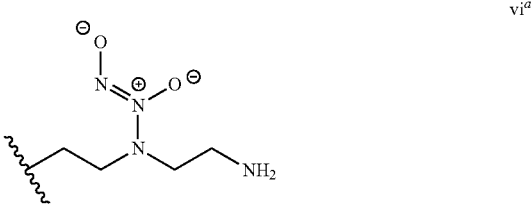
vi$^a$

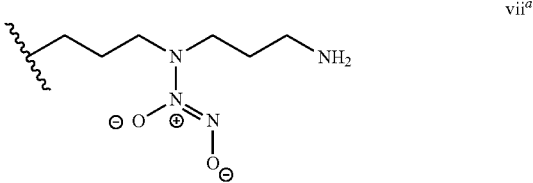
vii$^a$

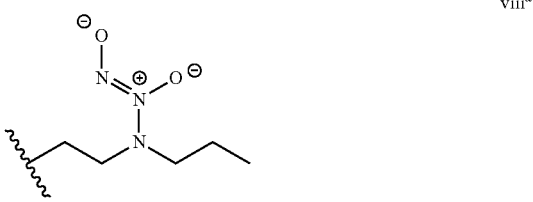
viii$^a$

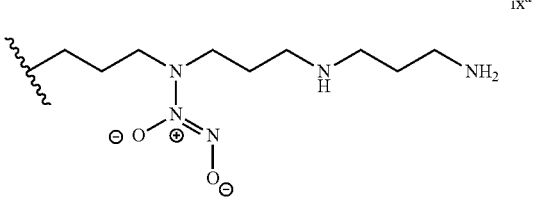
ix$^a$

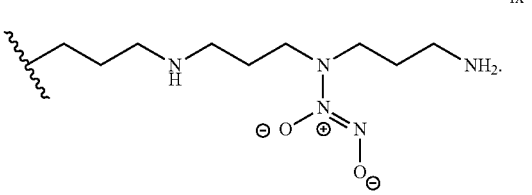
ix$^b$

In some embodiments,

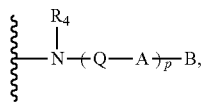

as shown elsewhere herein, has a structure selected from one or more of the following:

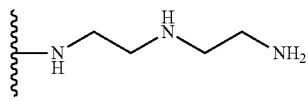

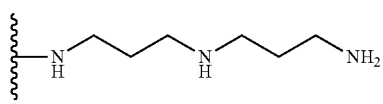

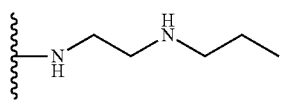

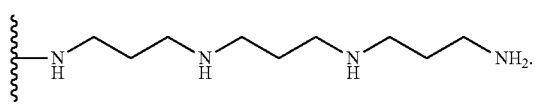

In some embodiments,

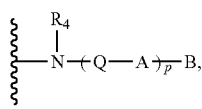

as shown elsewhere herein, has a structure selected from one or more of the following:

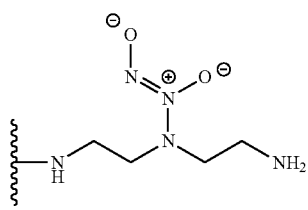

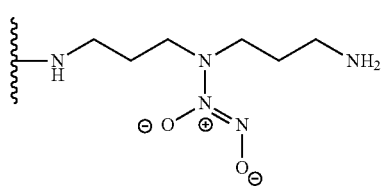

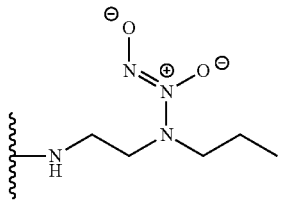

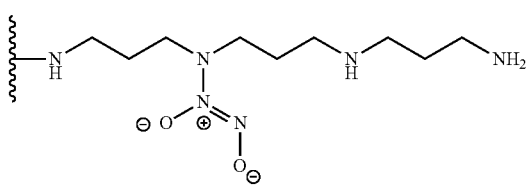

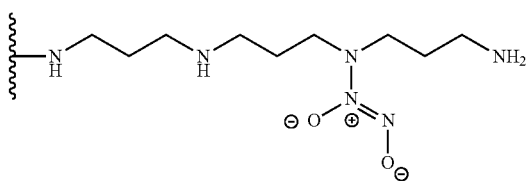

In some embodiments, the functionalized alginate is water soluble.

In some embodiments, the functionalized alginate has a total releasable nitric oxide storage in a range of 0.1-1.0 µmol of NO per milligram of the functionalized alginate. In some embodiments, the total releaseable nitric oxide storage is in the range between about 0.15-0.9, 0.2-0.8, 0.3-0.7, or 0.4-0.6 µmol of NO per milligram of the functionalized alginate. In some embodiments, on a µmol of NO per milligram of functionalized alginate basis, the functionalized alginate has a total releasable nitric oxide storage of greater than or equal to about: 0.1, 0.15, 0.2, 0.5, 0.7, 0.8, 0.9, 1.0, or ranges including and/or spanning the aforementioned values.

In several embodiments, a functionalized alginate wherein the NO-release has a half-life in the range of 0.1-24 hours. In some embodiments, the half-life is in the range between about 0.25-18 hours, 0.5-13 hours, 1-8 hours, 2-6 hours, or 3-4 hours. In some embodiments, NO-release half-life of the functionalized alginate is greater than or equal to about: 0.1 hours, 0.25 hours, 0.5 hours, 1 hour, 2 hours, 3 hours, 4 hours, 6 hours, 8 hours, 13 hours, 18 hours, 24 hours, or ranges including and/or spanning the aforementioned values.

In some embodiments, the total duration of NO release is in the range of 1-60 hours. In some embodiments, the total duration is in the range between about 2-50 hours, 3-40 hours, 4-30 hours, 5-20 hours, or 6-10 hours. In some embodiments, the total duration is greater than or equal to about: 1 hour, 2 hours, 3 hours, 4 hours, 5 hours, 6 hours, 10 hours, 20 hours, 30 hours, 40 hours, 50 hours, 60 hours, or ranges including and/or spanning the aforementioned values.

In some embodiments, the total NO release after 4 hours is in the range between 0.1-1.0 µmol of NO per milligram of the functionalized alginate. In some embodiments, the total releasable nitric oxide storage after 4 hours is in the range between about 0.15-0.9, 0.2-0.8, 0.3-0.7, or 0.4-0.6 µmol of NO per milligram of the functionalized alginate. In some embodiments, the total releasable nitric oxide storage after 4 hours (in µmol of NO per milligram of the functionalized alginate) is greater than or equal to about: 0.1, 0.15, 0.2, 0.3, 0.3, 0.6, 0.7, 0.8, 0.9, 1.0, or ranges including and/or spanning the aforementioned values.

In some embodiments, more than 15% of the monomers (e.g., repeat units) in the functionalized alginate are monomers of Formula I. In some embodiments, the percentage of monomers in the functionalized alginate are more than 20%, 25%, 30%, 40%, 50%, 60%, 70%, 80%, 90%, 95%, or 99% monomers of Formula I. In some embodiments, the percentage of monomers in the functionalized alginate having Formula I is greater than or equal to about: 20%, 25%, 30%, 40%, 50%, 60%, 70%, 80%, 90%, 95%, or 99%, or ranges including and/or spanning the aforementioned values.

In some embodiments, the functionalized alginate has a molecular weight in the range of 200-600 kDa. In some embodiments, the functionalized alginate has a molecular weight in the range of about 1 kDa to 1000 kDa, 5 kDa to 900 kDa, 50 kDa to 800 kDa, 200 kDa to 600 kDa, or 300 kDa to 400 kDa. In some embodiments, the functionalized alginate has a molecular weight of greater than or equal to about: 1 kDa, 5 kDa, 10 kDa, 50 kDa, 200 kDa, 300 kDa, 400 kDa, 600 kDa, 800 kDa, 1000 kDa, or ranges including and/or spanning the aforementioned values. In some embodiments, the functionalized alginate has a molecular weight of less than or equal to about: 5 kDa, 10 kDa, 50 kDa, 200 kDa, 300 kDa, 400 kDa, 600 kDa, 800 kDa, 1000 kDa, or ranges including and/or spanning the aforementioned values.

In some embodiments, the functionalized alginate comprising two or more different covalently modified monomers of Formula I.

Useful NO releasing moieties include any NO releasing group known in the art. In some embodiments, the NO releasing moieties are residues of NO releasing groups, i.e. NO donors, which are covalently bound to N on the functionalized alginate. In some embodiments, the NO donor is taken together with the atom on the alginate to which it is bound to form a moiety selected from the group consisting of a diazeniumdiolate, —NO as part of a nitrosothiol group for example, a nitrosamine, a hydroxyl nitrosamine, a hydroxyl amine, a hydroxyurea, and combination thereof. Preferably, the NO releasing moiety is a diazeniumdiolate. In some embodiments, these groups may be present in the form of a salt.

In some embodiments, the NO donor is a N-diazeniumdiolate (i.e., a 1-amino-substituted deazen-1-lum-1,2-diolate). N-Diazeniumdiolates are particularly attractive as NO donors due to their ability to generate NO spontaneously under biological conditions. Several N-diazeniumdiolate compounds have been synthesized using a range of nucleophilic residues that encompass primary and secondary amines, polyamines, and secondary amino acids. In the formation of the N-diazeniumdiolate, one equivalent of amine reacts with two equivalents of nitric oxide under elevated pressure. A base (e.g., an alkoxide like methoxide) removes a proton from the amine nitrogen to create the anionic, stabilized [N(O)NO] group. While stable under ambient conditions, N-diazeniumdiolates decompose spontaneously in aqueous media to generate NO at rates dependent upon pH, temperature, and/or the structure of the amine moiety. For example, N-diazeniumdiolate-modified proline (PROLI/NO), 2-(dimethylamino)-ethylputreamlne (DMAEP/NO), N,N-dimethylhexanediamine (DMHD/NO), and diethylenetriamine (DETA/NO) have been developed as small molecule NO donors with diverse NO release half-lives ranging from 2 seconds to 20 hours at pH 7.4 and 37° C.

In some embodiments, nitrosamine is not present during N-diazeniumdiolate formation.

In some embodiments, nitrosamine is not present during NO release. In some embodiments, the NO release may occur over a period of about 0.01 hours, 0.1 hours, 0.25 hours, 0.5 hours, 1 hour, 2 hours, 3 hours, 4 hours, 5 hours, 10 hours, 15 hours, 20 hours, 24 hours, 36 hours, 48 hours, or 60 hours. In some embodiments, the NO release occurs in less than or equal to about: 0.01 hours, 0.1 hours, 0.25 hours, 0.5 hours, 1 hour, 2 hours, 3 hours, 4 hours, 5 hours, 10 hours, 15 hours, 20 hours, 24 hours, 36 hours, 48 hours, 60 hours, or ranges including and/or spanning the aforementioned values. As used herein the phrase "nitrosamine is not present" refers to levels nitrosamine which are not detectable as determined by a UV-vis spectrum (or by other accepted methods in the art).

The term "amino" and "amine" refer to nitrogen-containing groups such as $NR_3$, $NH_3$, $NHR_2$, and $NH_2R$, wherein R can be as described elsewhere herein. Thus, "amino" as used herein can refer to a primary amine, a secondary amine, or a tertiary amine. In some embodiments, one R of an amino group can be a diazeniumdiolate (i.e., NONO).

The term "quaternary amine" refers to an amino group having an additional (i.e., a fourth) group, for example a hydrogen or an alkyl group bonded to the nitrogen. Thus, quaternary amines carry a positive charge.

The term "alkyl" denotes a straight or branched hydrocarbon chain containing 1-24 carbon atoms, e.g., 1-12 carbon atoms. Examples of alkyl group include methyl, ethyl, propyl, isopropyl, butyl, isobutyl, tert-butyl, and the like. Whenever it appears herein, a numerical range such as "1 to 24" or 1-24 refers to each integer in the given range; e.g., "1 to 10 carbon atoms" or "$C_1$-$C_5$ alkyl" means that the alkyl group may consist of 1 carbon atom, 2 carbon atoms, 3 carbon atoms, etc., up to and including 10 carbon atoms, (although the present definition also covers the occurrence of the term "alkyl" where no numerical range is designated, e.g., 1 to 24). By way of example only, "$C_1$-$C_5$ alkyl" indicates that there are one to five carbon atoms in the alkyl chain, i.e., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl, ethyl, propyl, isopropyl, butyl, isobutyl, tertiary butyl, pentyl and hexyl.

When a range of integers is given, the range includes any number falling within the range and the numbers defining ends of the range. For example, when the terms "integer from 1 to 10" is used, the integers included in the range are 1, 2, 3, 4, 5, 6, 7, 8, 9, and 10.

The term "covalently bound" or "covalently linked" refers to a chemical bond formed by sharing of one or more pairs of electrons.

As used herein, the term "contacting" refers to reagents in close proximity so that a reaction may occur.

In some embodiments, combinations of substituents and/or variables are permissible only if such combinations result in compounds that conform to a known valence for each atom.

Some embodiments pertain to a method for preparing a functionalized alginate. In some embodiments, the method comprises one or more of the following steps:

i. contacting an amine of Formula III

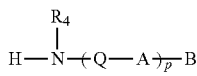

with an alginate in the presence of a peptide coupling reagent, wherein, $R_4$, Q, A, B and p are as described above, wherein a covalently modified monomer of Formula I is prepared

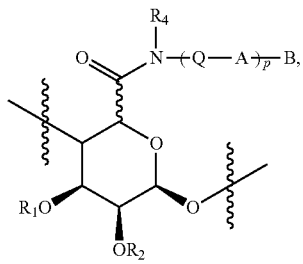

wherein, $R_1$, $R_2$, $R_4$, Q, A,
B and p are as described above; and
ii. contacting the alginate containing the covalently modified monomer of Formula I

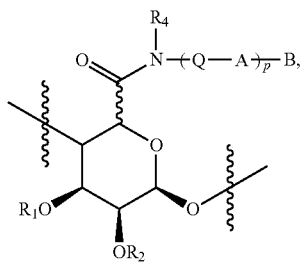

with a nitric oxide source, wherein,
$R_1$, $R_2$, $R_4$, Q, A, B and p are as described above, wherein a functionalized alginate is prepared.

In some embodiments, $R_1$ and $R_2$ are hydrogen or $C_{1-5}$ alkyl;
$R_3$ is hydrogen or $C_{1-5}$ alkyl; and
$R_4$ is, in each instance, hydrogen or $C_{1-5}$ alkyl;
v is 2 or 3;
L is N; and
p is an integer from 1 to 3.
In some embodiments, -(Q-A-)$_p$-B has one or more of the following structures:

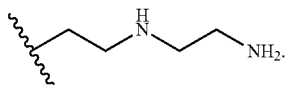

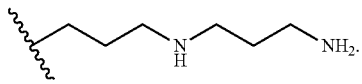

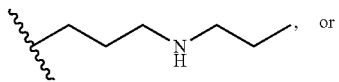

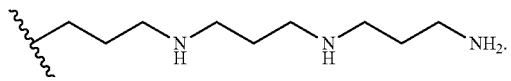

In some embodiments, G is taken together with a nitrogen to form a nitric oxide donor.

In some embodiments, the nitric oxide donor is diazeniumdiolate.

Functionalized alginates can be prepared through covalent modification of any available alginate polymer. Covalently modified monomers can be introduced into alginate polymers using a variety of synthetic procedures known in the art.

Representative chemical structures of an alginate are as follows:

The individual units are labeled as mannuronic acid (M) and guluronic acid (G) units. This representation depicts non-limiting potential polymer linkages which are designated as G block, M block, GM block, and MG blocks within a representative alginate. In some embodiments, at least one of M or G is replaced with a monomer of Formula I. In some embodiments, the percentage of monomers of Formula I in the functionalized alginate is at least 15%, at least 20%, at least 25%, at least 30%, at least 40%, at least 50%, at least 60%, at least 70%, at least 80%, at least 90%, at least 95%, or at least 99%. In some embodiments, the functionalized alginate further comprises a percentage of a monomer of Formula II. In some embodiments, the percentage of monomers of Formula II in the functionalized alginate is at least 15%, at least 20%, at least 25%, at least 30%, at least 40%, at least 50%, at least 60%, at least 70%, at least 80%, at least 90%, at least 95%, or at least 99%. In some embodiments, the percentage of monomers of Formula II in the functionalized alginate is at greater than or equal to about: 15%, 20%, 25%, 30%, 40%, 50%, 60%, 70%, 80%, 90%, least 95%, 99%, or ranges including and/or spanning the aforementioned values. In some embodiments. the combined percentage of monomers of Formula I and Formula II in the functionalized alginate is at least at least 15%, at least 20%, at least 25%, at least 30%, at least 40%, at least 50%, at least 60%, at least 70%, at least 80%, at least 90%, at least 95%, or at least 99%. In some embodiments, combined percentage of monomers of Formula I and Formula II in the functionalized alginate is at greater than or equal to about: 15%, 20%, 25%, 30%, 40%, 50%, 60%, 70%, 80%, 90%, least 95%, 99%, or ranges including and/or spanning the aforementioned values. In some embodiments, the monomer of Formula II is an unmodified M or G monomer. In some embodiments, the ratio of Formula I to Formula II monomers can be about: 30:1, 20:1, 10:1, 5:1, 1:1, 1:5, 1:10, 1:20, 1:30, ratios between the aforementioned ratios, or otherwise.

The proportion, distribution, and length of these G and M blocks in an alginate can affect the chemical and physical properties of alginate polymers. In some embodiments, embodiments of a "high-G alginate" are used. In high-G alginate there are more guluronate monomers present than other types of monomers or there are more guluronate monomers present than mannuronate monomers. For example, a high-G alginate can include over about 50% or at least about 65% of the alginate monomers as guluronate by molar percentage or by weight percentage. In some embodiments, embodiments of a "high-M alginate" are used. In high-M alginate there are more mannuronate monomers present than other types of monomers or there are more mannuronate monomers present than guluronate monomers. For example, a high-M alginate can include over about 50% or at least about 65% of the alginate monomers as mannuronate by molar percentage or by weight percentage. In some embodiments, there are about as many M monomers as G monomers. In some embodiments, the percentage of "G" monomers in the functionalized alginate is at least 15%, at least 20%, at least 25%, at least 30%, at least 40%, at least 50%, at least 60%, at least 70%, at least 80%, at least 90%, at least 95%, or at least 99%. In some embodiments, the percentage of "M" monomers in the functionalized alginate is at least 15%, at least 20%, at least 25%, at least 30%, at least 40%, at least 50%, at least 60%, at least 70%, at least 80%, at least 90%, at least 95%, or at least 99%.

In some embodiments, mannuronate and guluronate monomers are covalently modified via esterification and/or amidation of their carboxylic acid moiety. Stoichiometric variation of the reactants during covalent modification can be used to vary the amount of covalently modified monomer in the functionalized alginate. For example, in an embodiment, the stoichiometric ratio of EDC:monomer or amine: monomer during the formation of a functionalized alginate may be 10:1, 5:1, 4:1, 3:1, 2:1, 1:1, or 0.5:1. Preferably, the ratio is 2:1, EDC:monomer and/or 2:1 amine:monomer. In addition to the reactions discussed below, alternative synthetic methodologies for the covalent modification of mannuronate and guluronate monomers are known in the art. (See, for example, Smith, M. and March, J., March's Advanced Organic Chemistry: Reactions, Mechanisms, and Structure, 5th ed., New York: Wiley, 2001). Furthermore, variations in other reaction conditions, such as solvent, pH, and temperature are known in the art.

As used herein, a "buffer" is a solution that resists changes in pH when acid or base is added to it. Buffers typically involve a weak acid or bases together with one of its salts. Non-limiting examples of buffers are Tris, HEPES, PBS (phosphate buffered saline), triethylammonium acetate buffer, and triethylammonium bicarbonate buffer. The buffer may have a specified concentration and/or pH. In an embodiment, the buffer has a pH of about 2, 2.5, 3, 3.5, 4, 4.5, 5, 5.5, 6, 6.5, 7, 7.5, 8, 8.5, 9, 9.5, 10, 10.5, 11, 11.5, 12, or 12.5. In some embodiments, the pH is about 7.3 to about 11. In other embodiments, the pH is about 7.8 to about 9.3. In some embodiments, the pH is about 6.5. In some embodiments, the pH is about 7.5. In some embodiments, the pH is about 8.5. In some embodiments, the peptide coupling reactions can be performed in buffered solutions.

As used herein, the term "peptide coupling reagent" refers to a chemical used to facilitate the reaction between an amine and a carboxylic acid to form an amide bond. In some embodiments, suitable peptide coupling reagents include, without limitation, carbodiimide reagents, e.g., dicyclohexylcarbodiimide (DCC) or 1-(3-dimethylaminopropyl)-3-ethylcarbodiimide (EDC); phosphonium reagents, e.g., (benzotriazol-1-yloxy)tris(dimethylamino)phosphonium hexafluorophosphate (BOP); and uronium reagents, e.g., 0-(1H-benzotriazol-1-yl)-N,N,N',N'-tetramethyluronium tetrafluoroborate (TBTU). In some embodiments, one or more peptide coupling reagents can be used to covalently link primary or secondary amine containing groups to alginates via the carboxylic acid of the alginate. In some embodiments, as described elsewhere herein, one or more of bis(3-aminopropyl) amine (DPTA), diethylenetriamine (DETA), N-propyl-1,3-propanediamine (PAPA), spermine (SPER), can be functionalized to an alginate to provide a functionalized alginate. In some embodiments, a peptide coupling reagent is used with one or more compounds to provide functionalized alginate with a -(Q-A-)$_p$-B having one or more structures selected from vi, vii, viii, and ix.

As used herein, the term "nitric oxide source" refers to a source of nitric oxide useful for forming, for example, diazeniumdiolate NO donors. A non-limiting example of a nitric oxide source is NO gas.

In some embodiments, there are provided methods of delivering nitric oxide to a subject, comprising administering an effective amount of a functionalized alginate to a subject.

In some embodiments, there are provided methods of treating a disease state, comprising administering an effective amount of a functionalized alginate to a subject in need thereof. In some embodiments, the disease state is selected from the group consisting of a cancer, a cardiovascular disease, a microbial infection, platelet aggregation and/or platelet adhesion caused by the exposure of blood to a medical device, pathological conditions resulting from abnormal cell proliferation, transplantation rejections, autoimmune diseases, inflammation, vascular diseases; scar tissue, wound contraction, restenosis, pain, fever, gastrointestinal disorders, respiratory disorders, sexual dysfunctions, sexually transmitted diseases, and/or cystic fibrosis. In some embodiments, the disease state is a microbial infection, such as a bacterial infection. In some embodiments, the microbial infection is associated with another disease state such as cystic fibrosis.

In some embodiments, there are provided methods of disrupting, eradicating or preventing a biofilm. In some embodiments, the method comprises contacting a surface or area that contains a biofilm or is susceptible to a biofilm forming or occupying some or all of the surface or area with a functionalized alginate as described herein. The term "biofilm" is intended to mean an aggregate of one or more microorganisms in which cells adhere to each other, usually on a surface. Most any free-floating microorganisms can form a biofilm and/or attach to a surface. Microorganisms can adhere to a surface or each other through weak, reversible adhesion via van der Waals forces. The microorganisms can more permanently anchor using cell adhesion or structures such as pili.

In some embodiments, there is provided a pharmaceutical formulation comprising a functionalized alginate. In some embodiments, the pharmaceutical formulation comprises a pharmaceutically acceptable excipient. In some embodiments, the functionalized alginate is water-soluble as described elsewhere herein.

"Pharmaceutically acceptable," as used herein, means a material that is not biologically or otherwise undesirable, i.e., the material can be administered to an individual along with the compositions of the subject matter described herein, without causing substantial deleterious biological effects or interacting in a deleterious manner with any of the other components of the composition in which it is contained. The material would naturally be selected to minimize any degradation of the active ingredient and to minimize any adverse side effects in the subject (See, e.g., Remington's Pharmaceutical Science; 20 ed. 2005). Example pharmaceutically acceptable excipients for the compositions of the subject matter described herein include, but are not limited to, sterile pyrogen-free water and sterile pyrogen-free physiological saline solution.

The presently disclosed therapeutic compositions, in some embodiments, comprise a composition that includes a presently disclosed nitric oxide-releasing alginate and a pharmaceutically acceptable excipient. Suitable compositions include, but are not limited to, aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In some embodiments, the compositions used in the methods disclosed herein can take such forms as suspensions, solutions or emulsions in oily or aqueous vehicles, and can contain formulatory agents, such as suspending, stabilizing and/or dispersing agents. Alternatively, the active ingredient can be in powder form for constitution with a suitable vehicle, e.g., sterile pyrogen-free water, before use.

In some embodiments, the therapeutic compositions disclosed elsewhere herein can be presented in unit-dose or multi-dose containers, for example sealed ampoules and vials, and can be stored in a frozen or freeze-dried (lyophilized) condition requiring only the addition of sterile liquid carrier immediately prior to use.

In some embodiments, for oral administration, the compositions disclosed elsewhere herein can take the form of, for example, tablets or capsules prepared by a conventional technique with pharmaceutically acceptable excipients, such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art. For example, a therapeutic agent can be formulated in combination with hydrochlorothiazide, and as a pH stabilized core having an enteric or delayed release coating which protects the therapeutic agent until it reaches the target organ.

A "pharmaceutically acceptable excipient" refers to an ingredient in a pharmaceutical formulation, other than an active ingredient, which is nontoxic to a subject. A pharmaceutically acceptable excipient includes, but is not limited to, a buffer, carrier, stabilizer, or preservative. In some embodiments, the subject matter disclosed herein is directed to a pharmaceutical formulation comprising a functionalized alginate and a pharmaceutically acceptable excipient.

In some embodiments, liquid preparations of the disclosed compounds can be prepared. In some embodiments, liquid preparations for oral administration can take the form of, for example, solutions, syrups or suspensions, or they can be presented as a dry product for constitution with water or other suitable vehicle before use. In some embodiments, the such liquid preparations can be prepared by conventional techniques with pharmaceutically acceptable additives, such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). In some embodiments, the preparations can contain buffer salts, flavoring, coloring and sweetening agents as appropriate. In some embodiments, the preparations for oral administration can be suitably formulated to give controlled release of the active compound. In some embodiments, for buccal administration the compositions can take the form of tablets or lozenges formulated in conventional manner.

In some embodiments, the compounds disclosed elsewhere herein also can be formulated as a preparation for implantation or injection. Thus, for example, in some embodiments, the compounds can be formulated with suitable polymeric or hydrophobic materials (e.g., as an emulsion in an acceptable oil) and/or ion exchange resins, and/or as sparingly soluble derivatives (e.g., as a sparingly soluble salt). In some embodiments, the compounds also can be formulated in rectal compositions (e.g., suppositories or retention enemas containing conventional suppository bases, such as cocoa butter or other glycerides), creams or lotions, and/or transdermal patches.

In some embodiments, pharmaceutical formulations of the compounds disclosed herein are provided. In some embodiments, the pharmaceutical formulations are suitable for administration as an aerosol by inhalation. In some embodiments, the functionalized alginates described herein are formulated in solution and/or aerosol form. In some embodiments, these formulations comprise a solution or suspension of a NO-releasing alginate described herein. In some embodiments, the desired formulation can be placed in a small chamber and nebulized. In some embodiments, nebulization can be accomplished by compressed air or by ultrasonic energy to form a plurality of liquid droplets or solid particles comprising the NO-releasing alginate. For example, in some embodiments, the disclosed NO-releasing alginate can be administered via inhalation to treat bacterial infections related to cystic fibrosis. In some embodiments, the disclosed NO-releasing alginates can provide dual action antibacterial and mucolytic action. In some embodiments, this dual action is beneficial in the treatment of cystic fibrosis.

Cystic fibrosis is a genetic disorder caused by a malfunction of the cystic fibrosis transmembrane conductance regulator (CFTR) gene. The CFTR protein serves as an ion channel for chloride and bicarbonate ions which influence pH around airway epithelial cells and mucus viscoelasticity, a heterogeneous gel secreted from goblet cells consisting of water, proteins, salts, lipids, and mucins. Malfunction of these channels causes dehydration of the epithelial surface and increased mucin concentration. Although CF affects all mucus-producing organs, the progression in lung disease is the most life threatening effect. The increased viscoelasticity of mucus in CF contributes to the pathogenesis of the disease because removal of pathogens from the lungs becomes very difficult. The thickened mucus layer adheres to the surface of the airway epithelium and mucociliary clearance fails, leading to airway obstruction, bacterial infection, chronic inflammation, and permanent structural damage to the airway.

The accumulation of viscous mucus provides an ideal environment for bacterial growth, serving as both a physical support and nutrient source, and leads to further inflammation of the airway. Lung infections caused by pathogens such as *Pseudomonas aeruginosa*, which infects about 80% of CF adults, can become chronic, forming biofilms which traditional antibiotics cannot eradicate even at high doses. In addition, the abnormal mucus found in CF airways mitigates penetration of antibacterial agents to the colonies and leads to chronic infection, pulmonary obstruction, and patient mortality. Biofilm growth worsens mucus rheology as neutrophils recruited to the site of infection die and release DNA into the mucus, further increasing viscosity. Highly elastic mucus in CF patients correlates to worsening bacterial colonization and disease severity.

The majority of commercially available CF treatments aim to control mucus hypersecretion and eradicate bacterial infections. Two therapies designed to directly affect mucus rheology used today are N-acetylcysteine (NAC) and dornase alfa, operating through disulfide bond disruption and enzymatic degradation of DNA, respectively. The efficacy of NAC is limited by low potency and airway irritation, while dornase alfa treatment has been associated with upper airway irritation, rash, chest pain, and conjunctivitis, with some patients developing resistance to the drug. Additionally, CF pathogens like *P. aeruginosa* are largely protected from traditional antibiotic treatment (i.e. tobramycin and azithromycin) by biofilm formation in the viscous mucus. Bacteria surviving treatment can redevelop biofilms and promote antibiotic resistant strains. Disclosed herein are improved CF therapeutics that combine bacteria eradication with decreasing mucus viscoelasticity to improve clearance.

Cystic fibrosis-related bacterial infections include, but are not limited to *stenotrophomonis, mybacterium avium intracellulaire* and *M. abcessus, burkhoderia cepacia* and *Pseudomonas aeruginosa (P. aeruginosa)* infections. In some embodiments, the disclosed NO-releasing alginates can be used to treat infection by one or more of *stenotrophomonis, mybacterium avium intracellulaire* and *M. abcessus, burkhoderia cepacia* and/or *Pseudomonas aeruginosa (P. aeruginosa)*. In some embodiments, the disclosed NO-releasing alginates are mucolytic. In some embodiments, as disclosed elsewhere herein, the disclosed NO-releasing alginates are both mucolytic and antimicrobial and provide enhanced treatment efficacy for CF.

In some embodiments, the disclosed NO-releasing alginates can decrease the viscosity of mucus associated with CF by at least about: 20%, 50%, 70%, 90%, 95%, or ranges including and/or spanning the aforementioned values. In some embodiments, the disclosed NO-releasing alginates can decrease the elasticity of mucus associated with CF by at least about: 10%, 20%, 50%, 60%, 80%, or ranges including and/or spanning the aforementioned values. In some embodiments, the disclosed NO-releasing alginates do not cause collapse of mucin layers associated with CF and/or retain the thickness of the mucin layer. In some embodiments, the disclosed NO-releasing alginates do not increase and/or reduce the viscoelasticity of mucin layers associated with CF. In some embodiments, the disclosed NO-releasing alginates decrease G', G" and/or $\eta^*$ of mucus to promote drug diffusion through mucus. In some embodiments, the disclosed NO-releasing alginates decrease G', G" and/or $\eta^*$ of mucus by at least about: 20%, 50%, 70%, 90%, 95%, or ranges including and/or spanning the aforementioned values.

In some embodiments, for administration of a composition as disclosed herein, conventional methods of extrapolating human dosage based on doses administered to a murine animal model can be carried out. In some embodiments, extrapolations can be performed using the following conversion factor for converting the mouse dosage to human dosage: Dose Human per kg=Dose Mouse per kg×12. In some embodiments, drug doses also can be given in milligrams per square meter of body surface area because this method rather than body weight achieves a good correlation to certain metabolic and excretionary functions. Moreover, body surface area can be used as a common denominator for drug dosage in adults and children as well as in different animal species. Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

In some embodiments, suitable methods for administering to a subject a composition of the presently disclosed subject matter include, but are not limited to, systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. In some embodiments, where applicable, continuous infusion can enhance drug accumulation at a target site.

The particular mode of drug administration used in accordance with the methods of the presently disclosed subject matter depends on various factors, including but not limited to the agent and/or carrier employed, the severity of the condition to be treated, and mechanisms for metabolism or removal of the active agent following administration.

In some embodiments, one or more additional therapeutic agents can be used in combination with the functionalized alginate. In some embodiments, such additional agents can be part of a formulation comprising the functionalized alginate or dosed as a separate formulation prior to, after, or at the same time (concurrently) as a formulation including the functionalized alginate. In some embodiments, such additional therapeutic agents include, in particular, anti-cancer therapeutics, anti-microbial agents, pain relievers, anti-inflammatories, vasodilators, and immune-suppressants, as well as any other known therapeutic agents that could enhance the alleviation of the disease or condition being treated. In some embodiments, "concurrently" means at the same time or sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. In some embodiments, the two compounds can be administered in the same or different formulations or sequentially. In some embodiments, concurrent administration can be carried out by mixing the compounds prior to administration, or by administering the compounds in two different formulations, for example, at the same point in time but at different anatomic sites or using different routes of administration.

In some embodiments, the choice of additional therapeutic agents to be used in combination with an NO-releasing alginate will depend on various factors including, but not limited to, the type of disease, the age, and the general health of the subject, the aggressiveness of disease progression, and the ability of the subject to tolerate the agents that comprise the combination.

In some embodiments, the additional therapeutic agent(s) is an antimicrobial agents. As used herein, the term "antimicrobial agent" refers to any agent that kills, inhibits the growth of, or prevents the growth of a bacteria, fungus, yeast, or virus. Suitable antimicrobial agents that can be incorporated into the presently disclosed NO-releasing functionalized alginates to aid in the treatment or prevention of a microbial infection, include, but are not limited to, antibiotics such as vancomycin, bleomycin, pentostatin, mitoxantrone, mitomycin, dactinomycin, plicamycin and amikacin. Other antimicrobial agents include antibacterial agents such as 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefmenoxime, cefninox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clindamycin phosphate, clomocycline, colistin, cyclacillin, dapsone, demecicycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin and vancomycin. Antimicrobial agents can also include anti-fungals, such as amphotericin B, azaserine, candicidin(s), chlorphenesin, dermostatin(s), filipin, fungichromin, mepartricin, nystatin, oligomycin(s), perimycin A, tubercidin, imidazoles, triazoles, and griesofulvin. In several embodiments, the antimicrobial is selected from amoxicillin, amphotericin B, ampicillin, azithromycin, cefdinir, cephalosporin C, chloramphenicol, ciprofloxacin, clarithromycin, clindamycin, doxycycline, erythromycin, mupirocin, rifampin, tetracycline, and vancomycin.

In some embodiments, the NO-releasing alginate can be incorporated into polymeric films. In some embodiments, such incorporation can be through physically embedding the alginate into polymer surfaces, via electrostatic association of the alginate onto polymeric surfaces, or by covalent attachment of functionalized alginate onto reactive groups on the surface of a polymer. In some embodiments, the functionalized alginate can be mixed into a solution of liquid polymer precursor, becoming entrapped in the polymer matrix when the polymer is cured. In some embodiments, polymerizable groups can also be used to further functionalize the functionalized alginate, whereupon, the alginate can be co-polymerized into a polymer during the polymerization process. In some embodiments, suitable polymers into which the NO-releasing alginate can be incorporated include polyolefins, such as polystyrene, polypropylene, polyethylene, polytetrafluoroethylene, and polyvinylidene, as well as polyesters, polyethers, polyurethanes, and the like. In some embodiments, polyurethanes can include medically segmented polyurethanes. Medically segmented polyurethanes can also include one or more expander moieties, such as alkylene chains, that add additional length or weight to the polymer. Such polyurethanes are also generally nontoxic. One example of a medically segmented polyurethane is TECOFLEX®.

In some embodiments, the NO-releasing alginate can be incorporated into biodegradable and/or biocompatible polymers. In some embodiments, the NO-releasing polymer is a biodegradable and/or biocompatible polymer that is not alginate-based. In some embodiments, the biodegradable and/or biocompatible polymer can include one or more (e.g., copolymers or mixtures) of polylactic acid, poly(lactic-co-glycolic) acid, poly(caprolactone), polyglycolide, polylactide, polyhydroxobutyrate, chitosan, hyaluronic acid, hydrogels, poly(2-hydroxyethyl-methacrylate), poly(ethylene glycol), chitosan, poly(L-lactide), and combinations thereof. In some embodiments, a NO-releasing alginate can be incorporated into biodegradable and/or biocompatible polymers in a film.

In some embodiments, polymeric films containing NO-releasing alginates can be used to coat a variety of articles, particularly surgical tools, biological sensors, and medical implants to prevent platelet adhesion, to prevent bacterial infection, to act as a vasodilator. In some embodiments, these articles can be of use in vascular medical devices, urological medical devises, biliary medical devices, gastrointestinal medical devices, medical devices adapted for placement at surgical sites, and medical devices adapted for placement on skin wounds or openings. In some embodiments, the polymers can be used to coat arterial stents, guide wires, catheters, trocar needles, bone anchors, bone screws, protective platings, hip and joint replacements, electrical leads, biosensors, probes, sutures, surgical drapes, wound dressings, and bandages.

In some embodiments, the device being coated can have a metallic surface, such as, for example, stainless steel, nickel, titanium, aluminum, copper, gold, silver, platinum, and combinations thereof. In some embodiments, the films or polymers containing the NO-releasing alginate can be used to coat non-metallic surfaces, such as glass or fiber (e.g., cloth or paper).

In some embodiments, polymers containing NO-releasing alginate can be used to form the devices, themselves. For example, the polymers can be fashioned into storage bags for blood or tissue or as wound dressings.

In some embodiments, surfaces that can be contacted with a functionalized alginate to prevent or disrupt biofilms include those selected from the group consisting of medical devices, plumbing fixtures, condenser coils, optical surfaces, boat hulls and aircrafts. Other non-limiting examples include counter tops, windows, appliances, hard floors, rugs, tubs, showers, mirrors, toilets, bidets, bathroom fixtures, sinks, refrigerators, microwaves, small kitchen appliances, tables, chairs, cabinets, drawers, sofas, love seats, benches, beds, stools, armoires, chests, dressers, display cabinets, clocks, buffets, shades, shutters, entertainment centers, arm rails, lamps, banisters, libraries, cabinets, desks, doors, shelves, couches, carts, pianos, statues and other art, racks, fans, light fixtures, pool tables, ping pong tables, soccer tables, card tables, tools (e.g., hand powered and/or hand held tools, electrical tools, air powered tools, etc.), telephones, radios, televisions, stereo equipment, CD and DVD players, analog and digital sound devices, palm computers, laptop computers, desktop and tower computers, computer monitors, mp3 players, memory storage devices, cameras, camcorders, vehicle surfaces (e.g., windshield; tires; metal, fiberglass, composite material and/or plastic outer surfaces; fabric and/or vinyl outer surfaces; fabric, vinyl, and/or leather interior surfaces; metal, plastic, wood and/or composite material interior surfaces, glass interior surfaces, etc.), bicycles, snowmobiles, motorcycles, off-road-vehicles, yard equipment, farm equipment, washing equipment (e.g., power washers, etc.), painting equipment (e.g., electric and air powered painting equipment, etc.), medical and/or dental equipment, marine equipment (e.g., sail boats, power boats, rafts, sail board, canoe, row boats, etc.), toys, writing implements, watches, framed pictures or paintings, books, and/or the like. Any surface where it is desirable to cause one or more types of liquids to run off of a surface, to not be absorbed into a surface, and/or to not stain a surface, can be a substrate. For example, a surface that is exposed to environmental conditions. Also where the surface can become a locus for microbial adhesion such as medical devices that contact bodily tissues or fluids is particularly preferred.

In some embodiments, as disclosed elsewhere herein, medical devices can be coated or otherwise treated with a functionalized alginate to prevent or disrupt biofilms. Medical devices such as catheters, which are adapted for movement through blood vessels or other body lumens, are typically provided with low-friction outer surfaces. If the surfaces of the medical devices are not low-friction surfaces, insertion of the devices into and removal of the devices from the body lumens becomes more difficult, and injury or inflammation of bodily tissue may occur. Low friction surfaces are also beneficial for reducing discomfort and injury that may arise as a result of movement between certain long term devices (e.g., long term catheters) and the surrounding tissue, for example, as a result of patient activity. Medical devices include a variety of implantable and insertable medical devices (also referred to herein as "internal medical devices"). Examples of such medical devices include, devices involving the delivery or removal of fluids (e.g., drug containing fluids, pressurized fluids such as inflation fluids, bodily fluids, contrast media, hot or cold media, etc.) as well as devices for insertion into and/or through a wide range of body lumens, including lumens of the cardiovascular system such as the heart, arteries (e.g., coronary, femoral, aorta, iliac, carotid and vertebro-basilar arteries) and veins, lumens of the genitourinary system such as the urethra (including prostatic urethra), bladder, ureters, vagina, uterus, spermatic and fallopian tubes, the nasolacrimal duct, the eustachian tube, lumens of the respiratory tract such as the trachea, bronchi, nasal passages and sinuses, lumens of the gastrointestinal tract such as the esophagus, gut, duodenum, small intestine, large intestine, rectum, biliary and pancreatic duct systems, lumens of the lymphatic system, the major body cavities (peritoneal, pleural, pericardial) and so forth. Non-limiting, specific examples of internal medical devices include vascular devices such as vascular catheters (e.g., balloon catheters), including balloons and inflation tubing for the same, hydrolyser catheters, guide wires, pullback sheaths, filters (e.g., vena cava filters), left ventricular assist devices, total artificial hearts, injection needles, drug delivery tubing, drainage tubing, gastroenteric and colonoscopic tubing, endoscopic devices, endotracheal devices such as airway tubes, devices for the urinary tract such as urinary catheters and ureteral stents, and devices for the neural region such as catheters and wires, trocar needles, bone anchors, bone screws, protective platings, joint replacements, electrical leads, biosensors, probes, sutures, surgical drapes, wound dressings, and bandages. Many devices in accordance with the subject matter described herein have one or more portions that are cylindrical in shape, including both solid and hollow cylindrical shapes.

In some embodiments, solid substrate materials can be coated or otherwise treated with a functionalized alginate to prevent or disrupt biofilms. Solid substrate materials can include organic materials (e.g., materials containing 50 wt % or more organic species) such as polymeric materials, and inorganic materials (e.g., materials containing 50 wt % or more inorganic species), such as metallic materials (e.g., metals and metal alloys) and non-metallic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others). Specific examples of non-metallic inorganic materials can be materials containing one or more of the following: metal oxides, including aluminum oxides and transition metal oxides (e.g., oxides of titanium, zirconium, hafnium, tantalum, molybdenum, tungsten, rhenium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Further, the NO-releasing alginate can be incorporated into detergents, such as, but not limited to, anti-microbial soaps. In some embodiments, NO-release from functionalized alginate embedded in bar soaps can be triggered by contact with water and/or a drop in pH upon use. In some embodiments, as the outer surface of the bar is eroded or dissolved, additional functionalized alginate within the bar surface become exposed for subsequent uses of the bar. NO-releasing alginate also can be suspended in liquid soaps. Such soaps or detergents can be used for personal hygiene or to provide anti-microbial treatments for fibers. Such soaps or detergents can also be used to treat household surfaces or any surface in a hospital or other medical environment that may be exposed to microbes such as bacteria, fungi or viruses.

The term "biocompatible" refers herein to organic solvents that do not induce toxic or unwanted side effects when administered to a patient in certain amounts.

In some embodiments, the functionalized alginate can be provided as a pharmaceutically acceptable salt. The formulations include all pharmaceutically acceptable salt forms thereof. Examples of such salts include those derived from pharmaceutically acceptable inorganic and organic acids and bases. Examples of suitable acid salts include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the subject matter described herein and their pharmaceutically acceptable acid addition salts.

In some embodiments, salts derived from appropriate bases are used. Such salts include, without limitation, alkali metal (e.g., sodium, potassium), alkaline earth metal (e.g., magnesium and calcium), ammonium and N-(alkyl)$_4^+$ salts.

In some embodiments, the functionalized alginates also include those having quaternization of any basic nitrogen-containing group therein, thus providing a quaternary amine.

In some embodiments, the disclosed functionalized NO-releasing alginates have antimicrobial activity and provide greater than or equal to 99% bacterial reduction in a bacterial viability assay performed under static conditions over 4 hours with *P. aeruginosa* and/or *S. aureus* at a polymer concentration of equal to or less than 8 mg/mL. In some embodiments, the disclosed functionalized NO-releasing alginates elicit at least about 3-log reduction (i.e., 99.9% killing) in bacterial viability over 4 h ($MBC_{4h}$) with *P. aeruginosa* and/or *S. aureus* at a polymer concentration of equal to or less than 8 mg/mL. In some embodiments, the disclosed functionalized NO-releasing alginates have antimicrobial activity and provide greater than or equal to 99% bacterial reduction in a bacterial viability assay performed under static conditions over 4 hours at a polymer concentration of equal to or less than 8 mg/mL. In some embodiments, the disclosed functionalized NO-releasing alginates elicit at least about 3-log reduction (i.e., 99.9% killing) in bacterial viability over 4 h ($MBC_{4h}$) at a polymer concentration of equal to or less than 8 mg/mL. In some embodiments, the disclosed functionalized NO-releasing alginates elicit at least about 5-log reduction in bacterial viability over 8 h at a polymer concentration of equal to or less than 8 mg/mL.

The discussion herein is, for simplicity, provided without reference to stereoisomerism. The alginates described herein can contain one or more asymmetric centers and thus occur as racemates and racemic mixtures, single optical isomers, individual diastereomers, and diastereomeric mixtures. All such isomeric forms of these compounds are expressly included in the present subject matter.

Several embodiments of the present subject matter are explained in greater detail in the following non-limiting Examples.

EXAMPLES

Example 1: Synthetic Methods

Materials. Alginic acid sodium salt from brown algae (low viscosity), bis(3-aminopropyl) amine (DPTA), diethylenetriamine (DETA), N-propyl-1,3-propanediamine (PAPA), spermine (SPER), and trypan blue solution (0.4%) were purchased from Sigma-Aldrich (St. Louis, Mo.). Common laboratory salts and solvents were purchased from Fischer Scientific (Fair Lawn, N.J.). Unless otherwise specified, all chemicals were used as received without further purification. Tryptic soy broth (TSB) and tryptic soy agar (TSA) were obtained from Becton, Dickinson, and Company (Franklin Lakes, N.J.). The laboratory *Pseudomonas aeruginosa* (*P. aeruginosa*; ATCC #19143), *Staphylococcus aureus* (*S. aureus*; ATCC #29213), and A549 human lung adenocarcinoma cells (ATCC CCL-185) were obtained from American Type Tissue Culture Collection (Manassas, Va.). Bronchial Epithelial Cell Growth Medium (BGEM) used for cell growth was obtained from the UNC Tissue Procurement and Cell Culture Core (Chapel Hill, N.C.). Argon, carbon dioxide (CO2), nitrogen (N2), nitric oxide (NO) calibration (25.87 ppm, balance $N_2$) gas cylinders were purchased from Airgas National Welders (Raleigh, N.C.). Pure NO gas (99.5%) was obtained from Praxair (Sanford, N.C.). Distilled water was purified to a resistivity of 18.2 MΩ·cm and a total organic content of <10 ppb using a Millipore Milli-Q UV Gradient A10 System (Bedford, Mass.).

Instrumentation. $^1H$ and $^{13}C$ nuclear magnetic resonance (NMR) spectra were recorded on a Bruker (600 MHz) spectrometer. Elemental (carbon, hydrogen, and nitrogen; CHN) analysis was performed using a PerkinElmer Elemental Analyzer Series 2400 Instrument (Waltham, Mass.). Zeta potential measurements were taken in phosphate buffer (PB; pH 7.4) using a Zetasizer Nano (Malvern Instruments, UK). All UV measurements were obtained in 50 mM sodium hydroxide (NaOH) using a UV-vis Lambda 40 Spectrophotometer (PerkinElmer, Waltham, Mass.).

Synthesis of Polyamine-Functionalized Alginates. Alginate materials (designated "Alg-polyamine") were modified with either diethylenetriamine (DETA), bis(3-aminopropyl) amine (DPTA), N-propyl-1,3-propanediamine (PAPA), or spermine (SPER) through covalent amide bond formation between the carboxylic acid moieties of alginate and the primary amines of the polyamine. Briefly, alginate (100 mg) was dissolved in 10 mL phosphate buffered saline (PBS; 10 mM; pH 6.5) with a 2:1 molar ratio of 1-ethyl-3-(3-dimethylaminopropyl)carbodiimide hydrochloride (EDC) and 2:1 molar ratio of N-hydroxysuccinimide with respect to the carboxylic moieties of the alginate scaffold. A 2:1 molar ratio of the polyamine with respect to the carboxylic acid groups of the alginate scaffold was then added to the mixture, and the reaction was allowed to proceed for 24 h at room temperature. The amine-functionalized alginates were precipitated in methanol, collected via centrifugation, washed twice with methanol, and dried in vacuo to yield a white solid for each modification.

Representative $^1H$ NMR of alginate and the polyamine-functionalized alginates included the following peaks described below.

Alginate: $^1H$ NMR (600 MHz, $D_2O$, δ) 3.60-4.05 (OCHCH(OH)CH(OH)), 4.30 (OCHCH(OH)CH(OH), 4.50-4.60 (NHCOCH), 4.90 (OCH(CHOH)O).

Alg-DETA: $^1H$ NMR (600 MHz, $D_2O$, δ) 2.30-3.30 ($CH_2CH_2NHCH_2CH_2NH_2$), 3.60-4.05 (OCHCH(OH)CH (OH)), 4.30 (OCHCH(OH)CH(OH), 4.50-4.60 (NHCOCH), 4.90 (OCH(CHOH)O).

Alg-DPTA: $^1H$ NMR (600 MHz, $D_2O$, δ) 1.60-1.80 ($CH_2CH_2CH_2NHCH_2CH_2CH_2NH_2$), 2.60-2.30 ($CH_2CH_2CH_2NHCH_2CH_2CH_2NH_2$), 2.80-3.10 ($CH_2CH_2CH_2NHCH_2CH_2CH_2NH_2$), 3.60-4.05 (OCHCH (OH)CH(OH)), 4.30 (OCHCH(OH)CH(OH), 4.50-4.60 (NHCOCH), 4.90 (OCH(CHOH)O).

Alg-PAPA: $^1$H NMR (600 MHz, D$_2$O, δ) 0.70-0.80 (NHCH$_2$CH$_2$CH$_3$), 1.52 (NHCH$_2$CH$_2$CH$_3$), 1.85 (CH$_2$CH$_2$CH$_2$NHCH$_2$CH$_2$CH$_3$), 2.80-3.10 (CH$_2$CH$_2$CH$_2$NHCH$_2$CH$_2$CH$_3$), 3.60-4.05 (OCHCH(OH)CH(OH)), 4.30 (OCHCH(OH)CH(OH), 4.50-4.60 (NHCOCH), 4.90 (OCH(CHOH)O).

Alg-SPER: $^1$H NMR (600 MHz, D2O, 6) 1.13 (NHCH2(CH2)2CH2NH), 1.56 (NHCH2CH2CH2NH), 1.80 (C(O)NHCH2CH2CH2NH), 2.20-2.40 (CH2CH2CH2NH, NHCH2(CH2)2CH2NH, NHCH2CH2CH2NH2), 2.68 (NHCH2CH2CH2NH2), 2.80-3.10 (C(O)NHCH2CH2CH2NH, NHCH2CH2CH2NH2), 3.60-4.05 (OCHCH(OH)CH(OH)), 4.30 (OCHCH(OH)CH(OH), 4.50-4.60 (NHCOCH), 4.90 (OCH(CHOH)O).

Representative $^{13}$C NMR of alginate and the polyamine-functionalized alginate included the following peaks described below.

Alginate: $^{12}$C NMR (600 MHz, D$_2$O, δ) 65.0-80.0 (OCHCH(OH)CH(OH)CH(OH)CH(O)), 100.0 (OCHCH(OH)), 175.0 (CHC(O)).

Alg-DETA: $^{12}$C NMR (600 MHz, D$_2$O, δ) 39.0-47.0 (C(O)NHCH$_2$CH$_2$NHCH$_2$CH$_2$NH$_2$), 65.0-80.0 (OCHCH(OH)CH(OH)CH(OH)CH(O)), 100.0 (OCHCH(OH)), 160.0 (CHC(O)NH), 175.0 (CHC(O)).

Alg-DPTA: $^{13}$C NMR (600 MHz, D$_2$O, δ) 26.9-29.5 (C(O)NHCH$_2$CH$_2$CH$_2$NH, NHCH$_2$CH$_2$CH$_2$NH$_2$), 37.6-46.0 CH2 (C(O)NHCH$_2$CH$_2$CH$_2$NH, NHCH$_2$CH$_2$CH$_2$NH$_2$), 65.0-80.0 (OCHCH(OH)CH(OH)CH(OH)CH(O)), 100.0 (OCHCH(OH)), 160.0 (CHC(O)NH), 175.0 (CHC(O)).

$^{13}$C NMR (600 MHz, D$_2$O, δ) 10.9 (NHCH$_2$CH$_2$CH$_3$), 20.0 (NHCH$_2$CH$_2$CH$_3$), 31.3-49.0 (C(O)NHCH$_2$CH$_2$CH$_2$NH, NHCH$_2$CH$_2$CH$_3$), 65.0-80.0 (OCHCH(OH)CH(OH)CH(OH)CH(O)), 100.0 (OCHCH(OH)), 160.0 (CHC(O)NH), 175.0 (CHC(O)).

$^{13}$C NMR (600 MHz, D$_2$O, δ) 23.2 (NHCH$_2$(CH2)2CH$_2$NH), 34.8-45.0 (C(O)NHCH$_2$CH$_2$CH$_2$NH), 65.0-80.0 (OCHCH(OH)CH(OH)CH(OH)CH(O)), 100.0 (OCHCH(OH)), 160.0 (CHC(O)NH), 175.0 (CHC(O)).

Synthesis of secondary amine-functionalized alginate. Alginates are typically found in nature as polydisperse, high molecular weight polymers (200-500 kDa) and are water soluble even as large polysaccharides. The addition of secondary amine-bearing functional groups and other groups allows for nitric oxide storage and release capabilities for alginate through the subsequent formation of, for example, N-diazeniumdiolate NO donors. As described herein, small molecule amines were attached to the carboxylic acid moieties of alginate via EDC/NHS reactions (Scheme 1).

Scheme 1 Scheme 1 depicts the synthesis of amine-functionalized alginate.

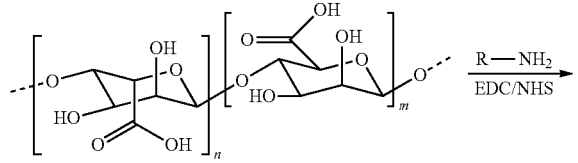

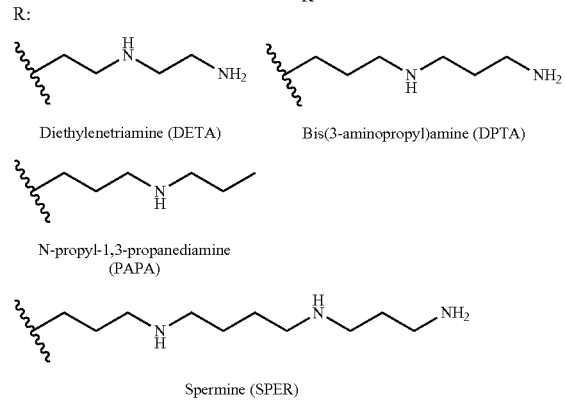

Diethylenetriamine (DETA)  Bis(3-aminopropyl)amine (DPTA)

N-propyl-1,3-propanediamine (PAPA)

Spermine (SPER)

Both $^1$H and $^{13}$C NMR were used to characterize the resulting alginate modifications (FIG. 4 and FIG. 5) and verify modification of the alginate backbone. Elemental analysis also confirmed amine attachment (Table 1). Grafting of the small amine moieties on the alginate backbone resulted in the presence of increasing nitrogen content from ~6 to 8 wt. % for Alg-PAPA, Alg-DETA, Alg-DPTA, and Alg-SPER (i.e., ~40-50% reaction conversion). A positive shift in the surface charge of the molecule is also seen with an increase in amines present in the scaffold (Table 1).

TABLE 1

Elemental (CHN) analysis and zeta potential measurements for secondary amine-functionalized alginate.[a]

| Sample | % C | % H | % N | Zeta Potential (mV)[b] |
|---|---|---|---|---|
| Alg | 30.41 ± 0.44 | 4.72 ± 0.42 | 0.05 ± 0.02 | −47.17 ± 2.83 |
| Alg-DETA | 35.15 ± 0.49 | 7.41 ± 0.51 | 7.65 ± 0.53 | −24.23 ± 2.41 |
| Alg-DPTA | 34.68 ± 0.56 | 7.37 ± 0.62 | 7.52 ± 1.11 | −23.10 ± 2.94 |
| Alg-PAPA | 34.71 ± 1.15 | 5.45 ± 0.05 | 6.69 ± 0.21 | −33.40 ± 1.62 |
| Alg-SPER | 40.41 ± 2.00 | 7.65 ± 0.53 | 8.28 ± 0.09 | −13.01 ± 2.51 |

[a]Each parameter was analyzed with multiple replicates (n ≥ 3).
[b]Measured in phosphate buffer, pH 7.4.

Synthesis of NO-releasing Alginates. To form N-diazeniumdio late NO donors on the alginate scaffolds, polyamine-functionalized alginate (45 mg) was dissolved using 50 mM NaOH solution (3 mL) in a 1-dram glass vial. The open vials were placed in a stainless steel reactor with continuous magnetic stirring. Oxygen was removed from the vessel by purging with argon (10 s, 7 bar) three times, followed by three additional long purges with argon (10 mins. 7 bar). The vessel was then pressurized to 10 bar with NO gas (purified over potassium hydroxide) for 3 days. Afterward, the same argon purging protocol was repeated to remove unreacted NO. The NO-releasing alginates were then precipitated in methanol, collected by centrifugation, dried overnight in vacuo, and stored at −20° C. as a white powder.

Characterization of NO Storage and Release. Nitric oxide release was evaluated in real-time using a Sievers 280i Chemiluminescence NO analyzer (NOA, Boulder, Colo.). Prior to analysis, the NOA was calibrated with air passed through a NO zero filter (0 ppm NO) and 25.87 ppm of NO standard gas (balance $N_2$). In a typical measurement, NO-releasing alginates (1 mg) were dissolved in 30 mL of PBS (pH 7.4, 37° C.). Nitrogen was flowed through the solution at a flow rate of 70 mL/min to carry the liberated NO from the alginate scaffold to the analyzer. Additional nitrogen flow was supplied to the flask to match the collection rate of the instrument (200 m/min). Nitric oxide analysis was terminated when NO levels fell below 10 ppb of NO/mg of alginate (the limit of detection of the instrument).

Synthesis of N-diazeniumdiolate-functionalized alginate. Secondary amine-functionalized alginates were exposed to high pressures of NO under basic conditions to form N-diazeniumdiolate NO donors. Nitric oxide storage was optimized for each sample by using aqueous 50 mM NaOH as the reaction solvent. N-diazeniumdiolate formation was confirmed using UV-vis spectroscopy with the presence of a characteristic absorbance maximum at 253 nm—a peak absent in the absorbance spectra of the secondary amine-functionalized alginates prior to diazeniumdiolate formation (FIG. 6).

Figure 1B:
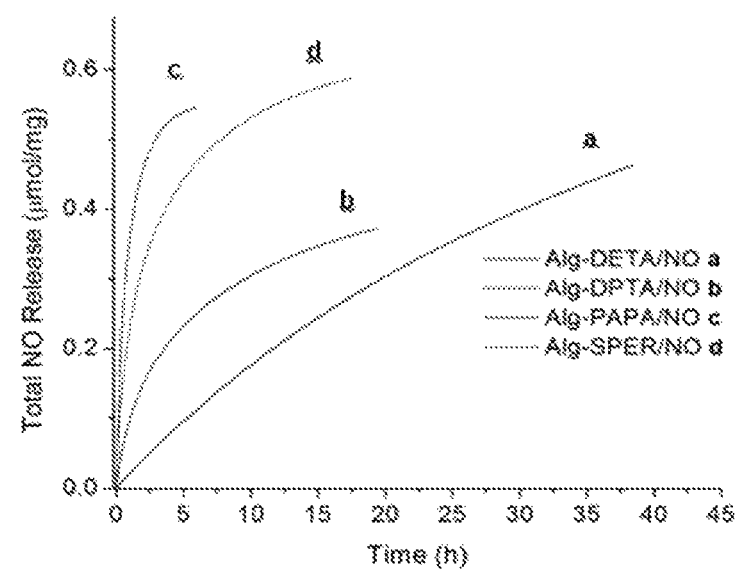

FIG. 1 shows the representative NO-release profiles for the N-diazeniumdiolate-functionalized alginates in PBS (pH 7.4) at 37° C. Both Alg-SPER/NO and Alg-PAPA/NO were found to have similar total NO storage of ~0.6 μmol/mg, whereas both Alg-DETA/NO and Alg-DPTA/NO released lower amounts of NO (~0.4 μmol/mg; Table 2). The above values are comparable to other macromolecular NO-releasing biopolymeric scaffolds, including reported NO totals achieved with NO-releasing chitosan oligosaccharides, a linear biodegradable scaffold. However, a broad range of NO-release kinetics was observed for the alginate scaffolds, with Alg-PAPA/NO having the shortest NO-release half-life (~0.5 h), and Alg-DETA/NO having the longest (~13 h). Without being bound by theory, it is believed that these trends in NO release kinetics were dependent on the amine precursor structure. Half-life values for small molecule precursors have been reported. These examples described herein demonstrate the ability to tune and control to a highly desirable specificity both total NO storage and release kinetics by varying the chemical structure of amine precursor grafted on the alginate backbone.

TABLE 2

Nitric oxide-release properties of N-diazeniumdiolate-functionalized alginate in PBS (pH 7.4, 37° C.).[a]

| Scaffold | t[NO][b] (μmol/mg) | [NO]$_{max}$[c] (ppb/mg) | $t_{1/2}$[d] (h) | $t_d$[e] (h) | t[NO]$_{4h}$[f] (μmol/mg) |
|---|---|---|---|---|---|
| Alg-DETA/NO | 0.40 ± 0.04 | 232 ± 78 | 13.1 ± 5.8 | 40.3 ± 14.2 | 0.10 ± 0.01 |
| Alg-DPTA/NO | 0.42 ± 0.04 | 428 ± 124 | 3.4 ± 0.6 | 16.1 ± 2.9 | 0.23 ± 0.01 |
| Alg-PAPA/NO | 0.61 ± 0.13 | 2110 ± 1240 | 0.5 ± 0.1 | 6.1 ± 1.0 | 0.59 ± 0.11 |
| Alg-SPER/NO | 0.65 ± 0.16 | 1236 ± 240 | 1.3 ± 0.4 | 14.6 ± 3.5 | 0.49 ± 0.11 |

[a]Each parameter was analyzed with multiple replicates (n ≥ 3).
[b]Total NO released.
[c]Maximum flux of NO release.
[d]NO-release half-life.
[e]Duration of NO release.
[f]Total NO released after 4 h.

Example 2: Biological Assays

Planktonic Bactericidal Assays. *P. aeruginosa* and *S. aureus* bacterial cultures were grown from a frozen (−80° C.) stock overnight in TSB at 37° C. A 500 μL aliquot of culture was grown in 50 mL of fresh TSB to a concentration of $10^8$ colony forming units per mL (CFU/mL). A working bacterial stock was generated by plating the bacterial suspension on TSA and incubating at 37° C. overnight. The TSA bacterial stocks were prepared weekly and stored at 4° C. For bactericidal assays, colonies of *P. aeruginosa* and *S. aureus* were taken from the TSA plate, inoculated in 3 mL TSB overnight at 37° C., and recultured in fresh TSB (50 mL) to a concentration of $10^8$ CFU/mL. These cultures were centrifuged, resuspended in PBS, and diluted to $10^6$ CFU/mL. Weighed samples of non-NO-releasing and NO-releasing alginates were added to a 1-dram vial. Corresponding volumes of the $10^6$ CFU/mL bacteria were then added to obtain a range of alginate concentrations (0.5 to 16 mg/mL) and incubated for 4 h at 37° C. Untreated controls (blanks) were included in each experiment to ensure bacteria viability over the duration of the experiment. Following treatment, the bacterial solutions were serially diluted (10- and 100-fold dilutions), spiral plated on TSA using an Eddy Jet spiral plater (IUL; Farmingdale, N.Y.), and incubated overnight at 37° C. Bacterial viability was assessed using a Flash & Go colony counter (IUL; Farmingdale, N.Y.). The minimum bactericidal concentration after a 4-hour exposure ($MBC_{4h}$) was defined as the minimum concentration required to achieve a 3-log reduction in bacterial viability compared to untreated cells (i.e., reduced bacterial counts from $10^6$ to $10^3$ CFU/mL). The plate counting method used has a limit of detection of $2.5 \times 10^3$ CFU/mL. The corresponding NO dose was calculated by multiplying the $MBC_{4h}$ of the alginate samples (mg/mL) with the available NO in PBS (pH 7.4; μmol NO/mg alginate).

Biofilm Eradication Assays. Similar to planktonic experiments, *P. aeruginosa* and *S. aureus* bacterial cultures were grown overnight in TSB at 37° C., and recultured in fresh TSB to a concentration of $10^8$ CFU/mL. The bacterial solutions were then diluted to $10^6$ CFU/mL in sterile medium (*P. aeruginosa*, TSB; *S. aureus*, TSB+0.1% glucose) and grown for 48 h at 37° C. with gentle shaking. The viscous microcolony biofilms formed were easily separated from the growth media via pipetting. The biofilms (250 μL) were combined with 750 μL of PBS and added to 1-dram vials containing premeasured samples of the non-NO-releasing and NO-releasing alginates, with final alginate concentrations ranging from 4 to 64 mg/mL. The samples were incubated with gentle shaking for 24 h at 37° C. Untreated controls (blanks) were included in each experiment to ensure bacterial viability over the duration of the experiment. The dispersed biofilms were vortexed, serially diluted (10-, 100-, 1000-, and 10,000-fold dilutions), plated on TSA plates using an Eddy Jet spiral plater (IUL; Farmingdale, N.Y.), and incubated overnight at 37° C. Bacterial viability was assessed using a Flash & Go colony counter (IUL; Farmingdale, N.Y.). The minimum biofilm eradication concentration at 24 h ($MBEC_{24}h$) was defined as the concentration that reduced the viability of the biofilm to below the limit of detection of the plate counting method ($2.5 \times 10^3$ CFU/mL) after the 24 h treatment. The corresponding NO dose was calculated by multiplying the $MBEC_{24h}$ of the alginate samples (mg/mL) with the available NO in PBS (pH 7.4; μmol NO/mg alginate).

Time-Based Biofilm Eradication Assay. *P. aeruginosa* biofilms were grown and treated with NO-releasing alginates (8 mg/mL) following the same protocol for the biofilm eradication assays. Untreated controls (blanks) were included to ensure bacteria viability over the duration of the experiment. The samples were incubated with gentle shaking at 37° C. with different lengths of exposure (1-8 h) before plating on TSA plates using an Eddy Jet spiral plater (IUL; Farmingdale, N.Y.) and overnight incubation at 37° C. Bacterial viability was assessed using a Flash & Go colony counter (IUL; Farmingdale, N.Y.). A similar experiment was carried out at the $MBEC_{24h}$ for Alg-PAPA/NO and Alg-SPER/NO for comparison to the time-based killing at 8 mg/mL.

In Vitro Cytotoxicity Assay. A549 human adenocarcinoma cells were grown in BGEM media and incubated in 5% $C_{O2}$ under humidified/aerobic conditions at 37° C. After reaching 80% confluency, the cells were seeded onto polystyrene 96-well plates at a density of $1 \times 10^4$ cells/mL per well, and incubated at 37° C. for 24 h. The supernatant was then aspirated and replaced with 200 μL fresh growth medium and 20 μL of alginate in PBS with a final alginate concentration equivalent to $MBEC_{24h}$ against *P. aeruginosa* or *S. aureus* biofilms. After 24 h incubation at 37° C., 50 μL trypan blue solution was added, and the mixture was incubated at room temperature for ~3 mins. The supernatant was aspirated and the wells were washed with PBS. Cells in each well were imaged using a Nikon Eclipse TE2000-E inverted microscope at a magnification of 40× equipped with Nikon Digital Sight DS-U2 controller. Images were processed using the NIS-Imaging Software, and a custom MATLAB script was used to differentiate and count the number of viable and dead cells in each image. Cell viability for each sample was calculated as follows:

$$\% \text{ Cell viability} = \frac{\text{total number of viable cells}}{\text{total number of cells}} \times 100$$

Example 3: Antibacterial Studies

Bactericidal activity of the NO-releasing alginates against *Pseudomonas aeruginosa* and *Staphylococcus aureus* pathogens were dependent on the NO-release kinetics, with ~4 h release half-lives requiring lower alginate concentrations to eradicate both planktonic and biofilm-based bacteria relative to faster releasing systems. Both NO-releasing and control alginates elicited low toxicity against human respiratory epithelial (A549) cells at concentrations needed to achieve a 5-log reduction in viability for biofilm-based bacteria.

Figure 7A:
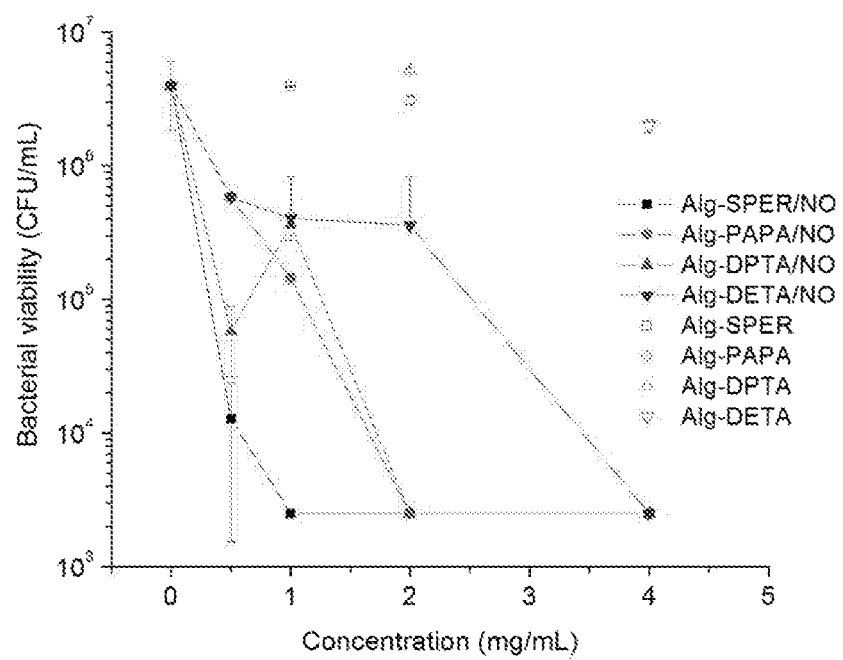
FIGS. 7A and 7B show anti-bacterial efficacy of embodiments of NO-releasing (filled markers) and control (hollow markers) alginates against planktonic (FIG. 7A) P. aeruginosa and (FIG. 7B) S. aureus. For all measurements, n≥3 pooled experiments.
Figure 7B:
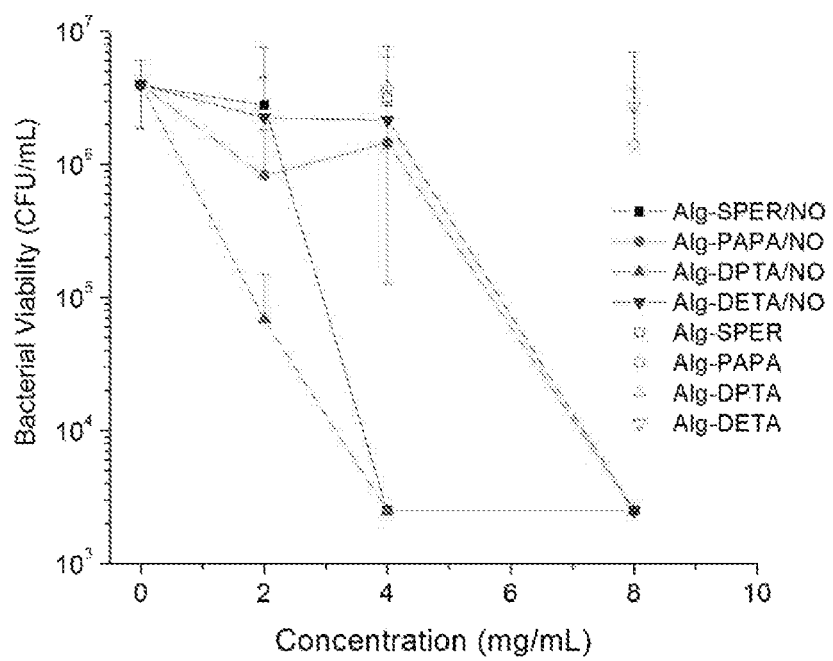
Figure 8A:
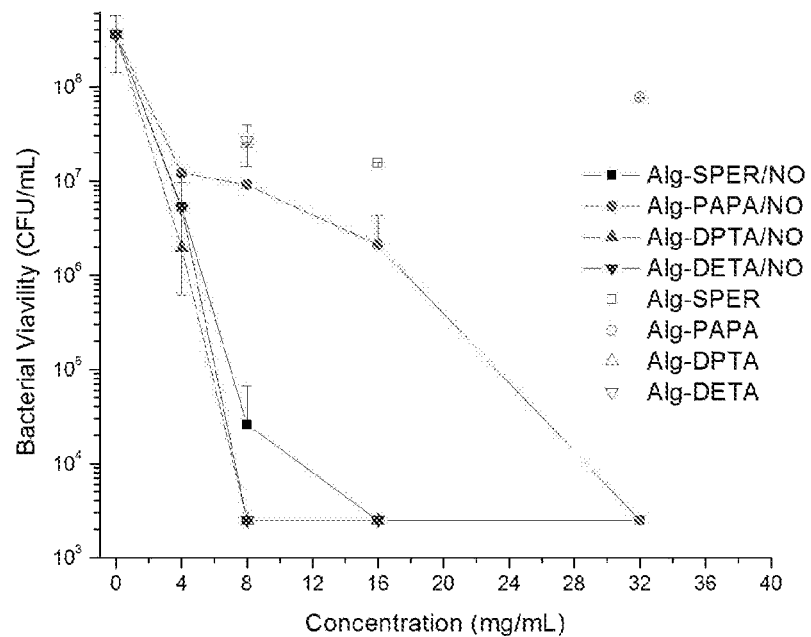
FIGS. 8A and 8B show anti-biofilm efficacy of an embodiment of NO-releasing (filled markers) and control (hollow markers) alginates against (FIG. 8A) P. aeruginosa and (FIG. 8B) S. aureus biofilms. For all measurements, n≥3 pooled experiments.
Figure 8B:
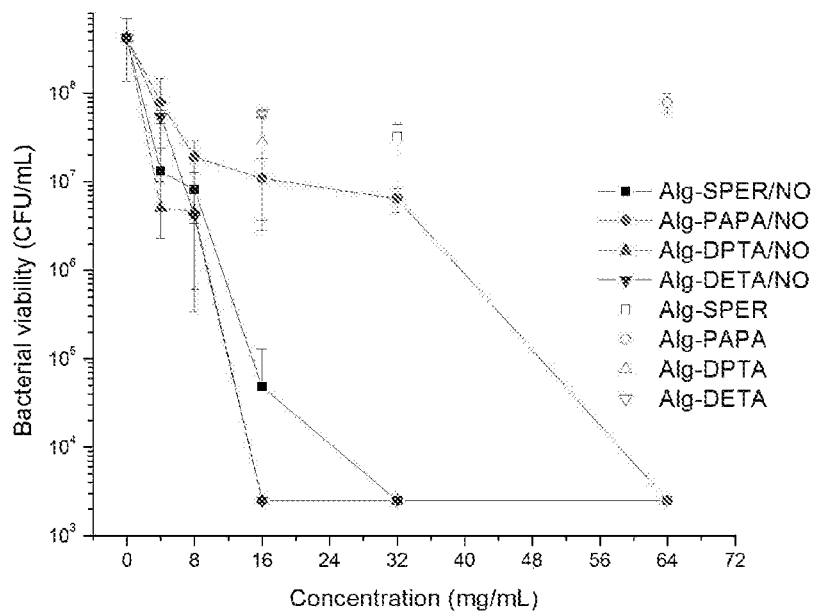
Figure 9A:
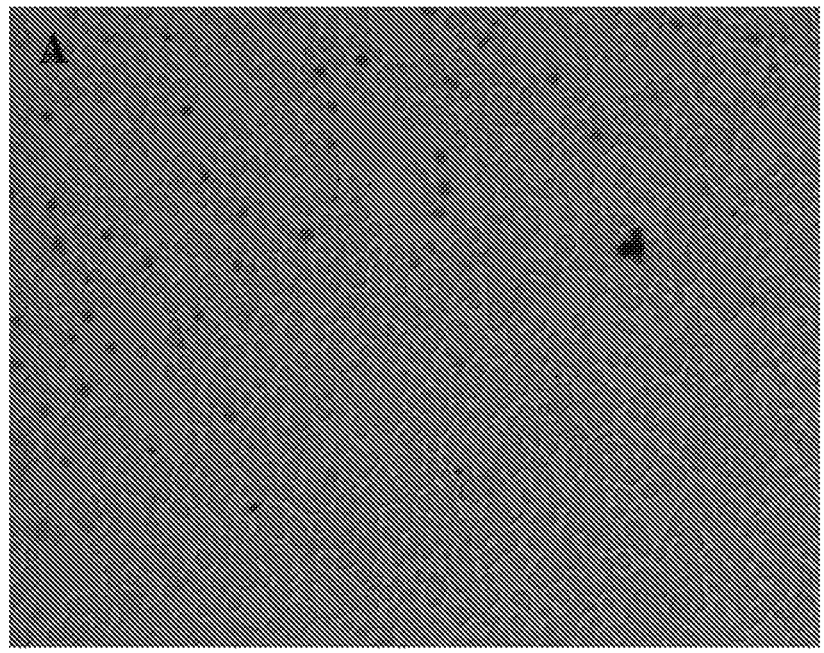
FIGS. 9A-9D show representative microscopy images of A549 cells treated for 24 h with (FIG. 9A) PBS pH 7.4 and with 32 mg/mL of (FIG. 9B) alginate, (FIG. 9C) an embodiment of Alg-SPER, and (FIG. 9D) an embodiment of Alg-SPER/NO.
Figure 9B:
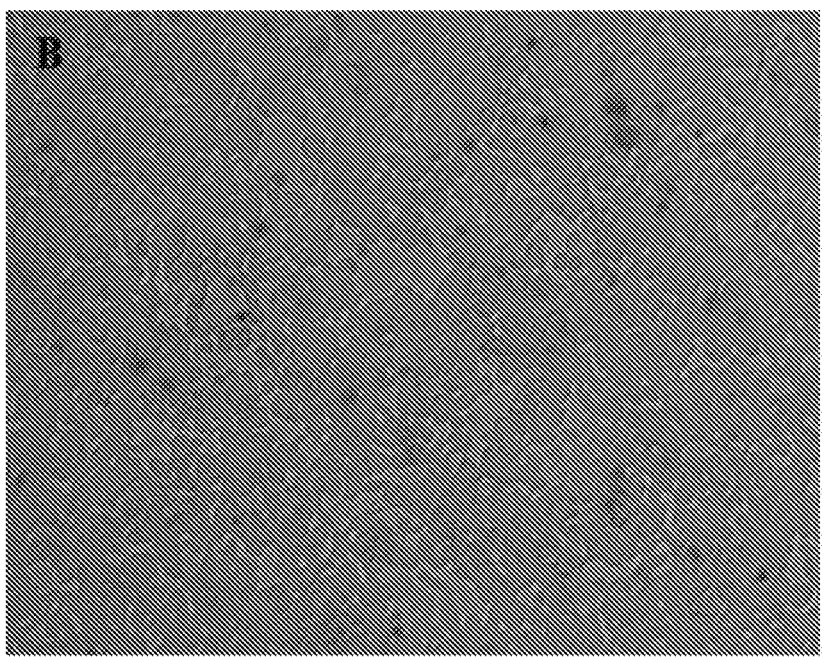
Figure 9C:
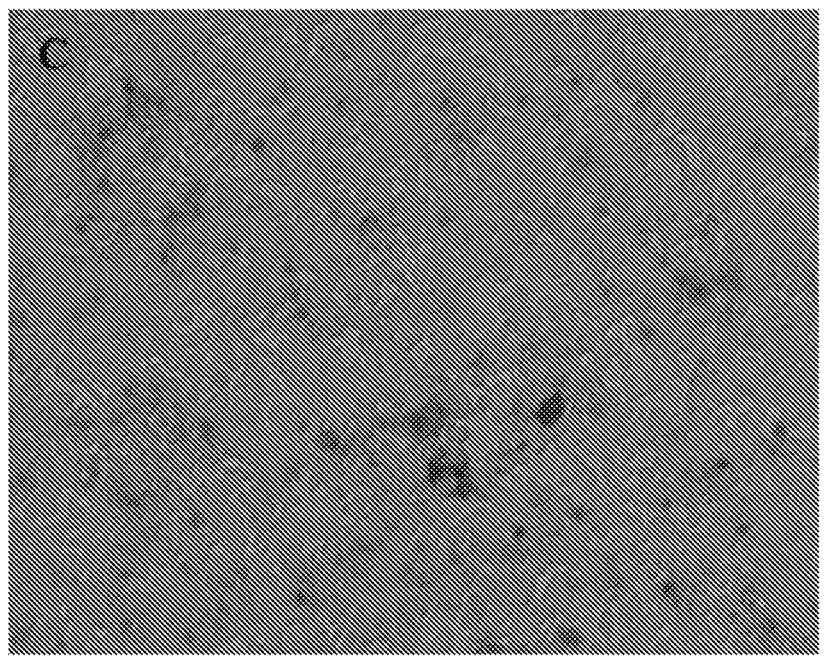
Figure 9D:
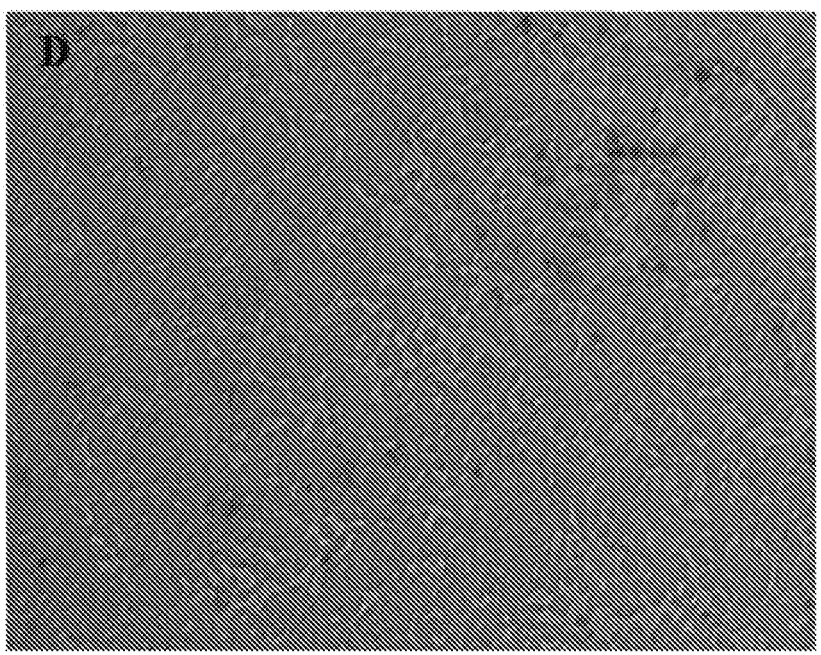
Figure 10:
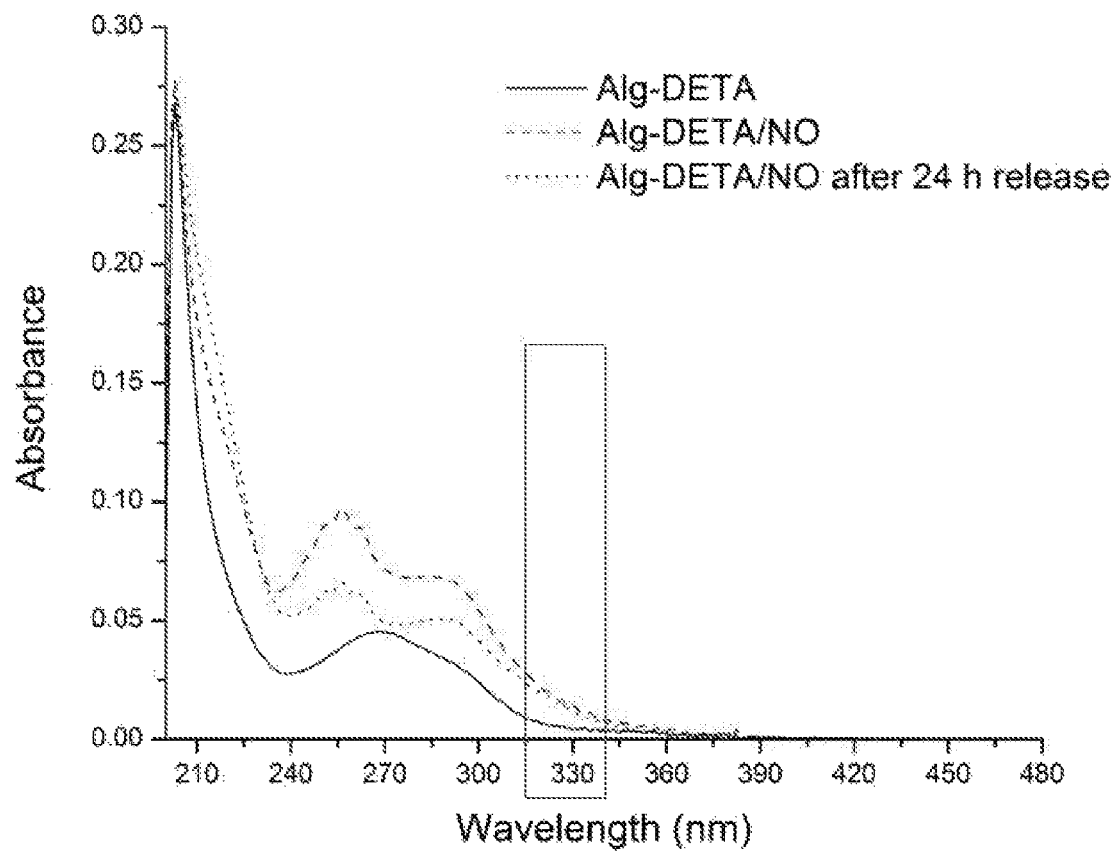
FIG. 10 shows a UV-vis spectra of an embodiment of Alg-DETA/NO releasing alginate. The area around 330 nm is boxed to highlight the absence of the sharp peak that corresponds to nitrosamine formation even after 24 h of NO-release in PBS pH 7.4.
Figure 11:
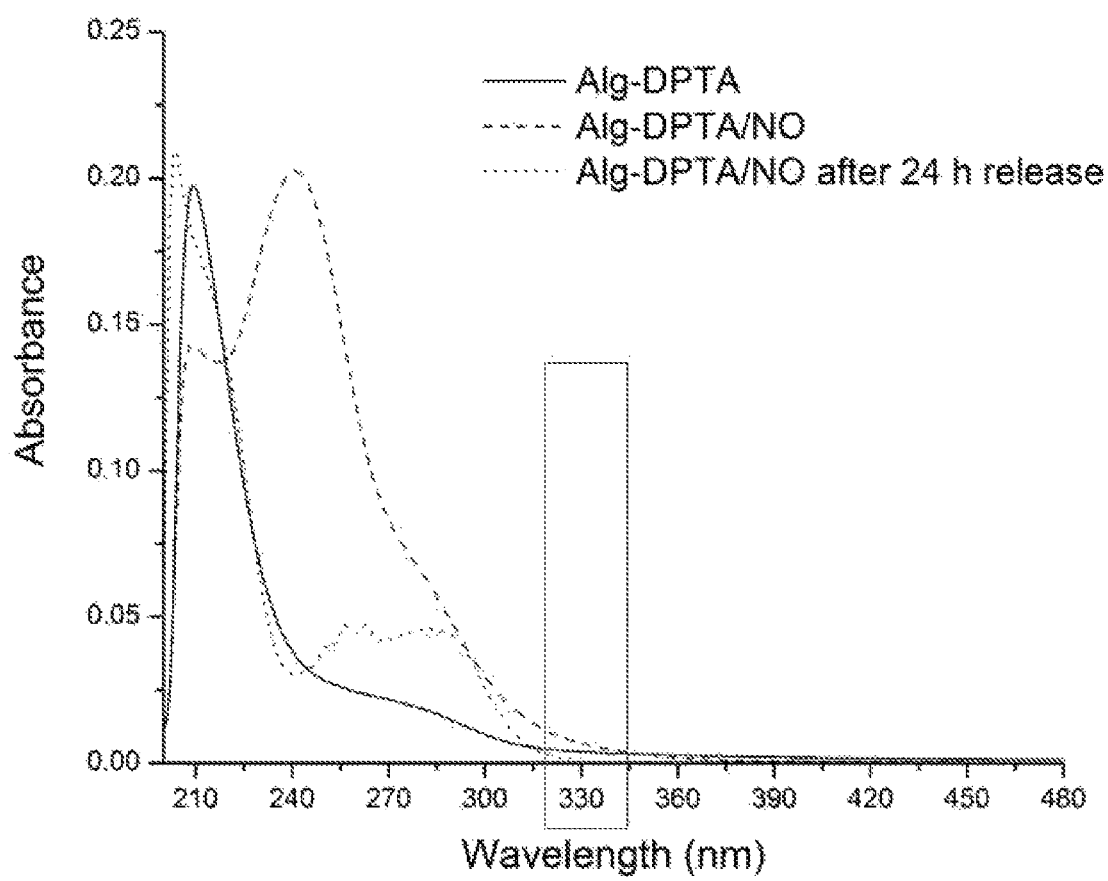
FIG. 11 shows a UV-vis spectra of an embodiment of Alg-DPTA/NO releasing alginate. The area around 330 nm is boxed to highlight the absence of the sharp peak that corresponds to nitrosamine formation even after 24 h of NO-release in PBS pH 7.4.
Figure 12:
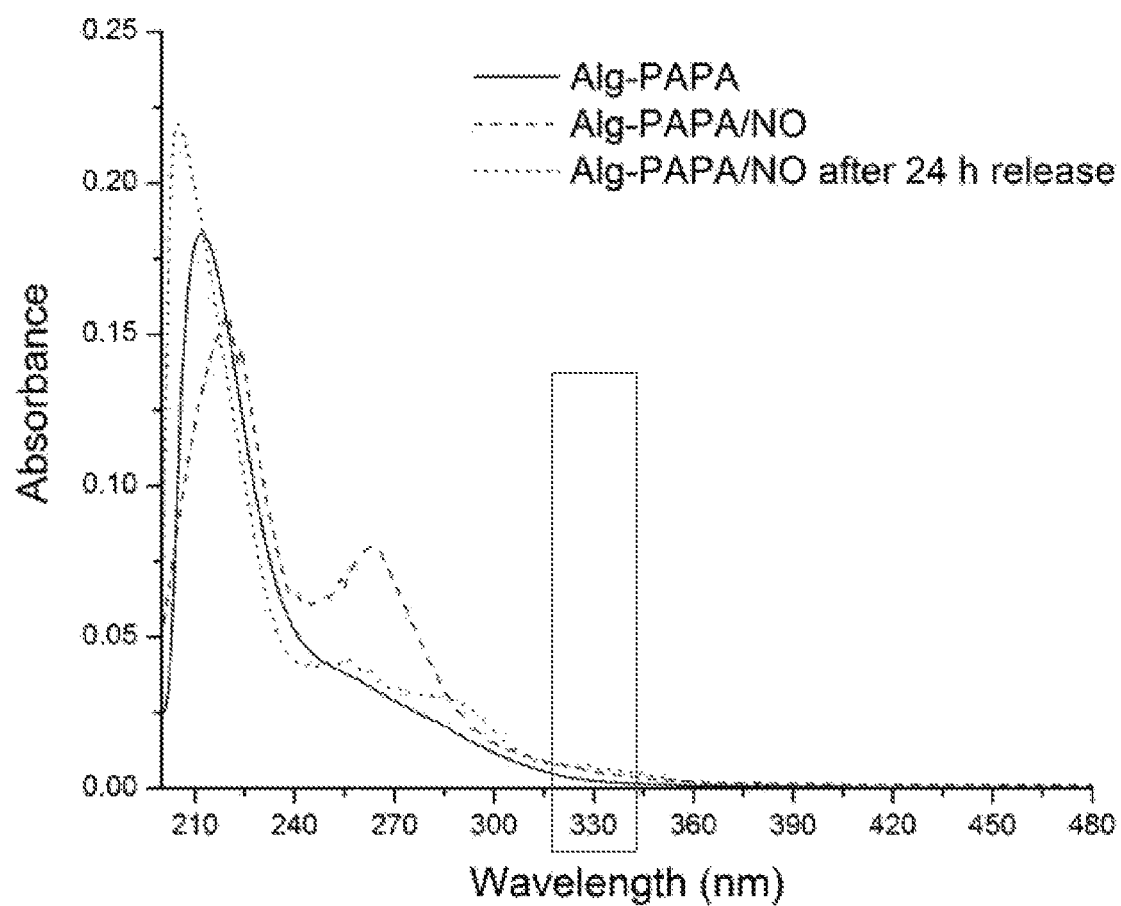
FIG. 12 shows a UV-vis spectra of an embodiment of Alg-PAPA/NO releasing alginate. The area around 330 nm is boxed to highlight the absence of the sharp peak that corresponds to nitrosamine formation even after 24 h of NO-release in PBS pH 7.4.
Figure 13:
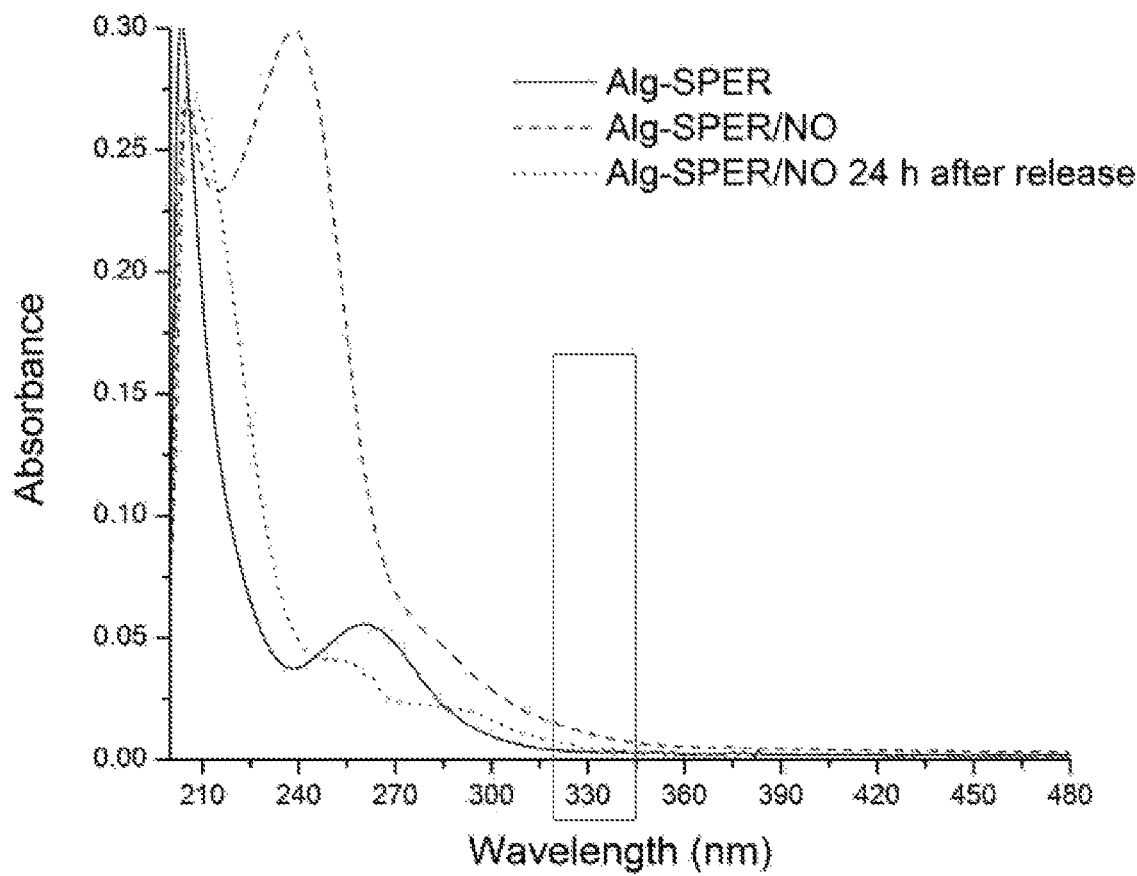
FIG. 13 shows a UV-vis spectra of an embodiment of Alg-SPER/NO releasing alginate. The area around 330 nm is boxed to highlight the absence of the sharp peak that corresponds to nitrosamine formation even after 24 h of NO-release in PBS pH 7.4.

Antibacterial action against planktonic bacteria. The antibacterial activities of the control and NO-releasing alginates were evaluated against *P. aeruginosa* and *S. aureus*, two of the most common pathogens associated with chronic infections. Bacterial viability assays were performed under static conditions to determine the minimum concentration of the NO-releasing alginates required to elicit a 3-log reduction (i.e., 99.9% killing) in bacterial viability over 4 h ($MBC_{4h}$). Both the $MBC_{4h}$ and the bactericidal NO dose required for each alginate modification are provided in Table 3. At equivalent concentrations, the control alginate materials did not exhibit a significant reduction in bacterial viability for both *P. aeruginosa* and *S. aureus*, implicating NO as the bactericidal agent (FIG. 7).

TABLE 3

Minimum bactericidal concentrations ($MBC_{4\ h}$) against planktonic *P. aeruginosa* and *S. aureus*.[a]

| | *P. aeruginosa* | | *S. aureus* | |
|---|---|---|---|---|
| Scaffold | $MBC_{4\ h}$ (mg/mL) | NO dose[b] (μmol/mL) | $MBC_{4\ h}$ (mg/mL) | NO dose[b] (μmol/mL) |
| Alg-DETA/NO | 4 | 0.40 ± 0.04 | 8 | 0.80 ± 0.08 |
| Alg-DPTA/NO | 2 | 0.45 ± 0.01 | 4 | 0.88 ± 0.02 |
| Alg-PAPA/NO | 2 | 1.18 ± 0.24 | 4 | 4.75 ± 0.95 |
| Alg-SPER/NO | 2 | 0.49 ± 0.11 | 8 | 1.96 ± 0.45 |

[a]Each parameter was analyzed with multiple replicates (n ≥ 3).
[b]NO dose was calculated from NO totals at 4 h in PBS at pH 7.4..

Each of the NO-releasing alginate scaffolds achieved ≥99.9% bacterial killing at relatively low concentrations (<8 mg/mL), with the less negatively charged alginate modifications requiring lower concentrations to achieve bactericidal activity (Table 1). Previous studies have reported that positively charged scaffolds associate more readily with bacteria, resulting in enhanced bactericidal action. The data disclosed herein show that Alg-SPER/NO needs the lowest concentration to elicit bactericidal action and Alg-PAPA/NO requires the highest. Without being bound by theory, it is believed release kinetics play a role in the concentration needed to elicit bactericidal action for the alginate materials, with Alg-PAPA/NO having the same MBC concentration as Alg-DPTA/NO and Alg-DETA/NO against *P. aeruginosa* and *S. aureus*, respectively. Despite greater total NO release (~0.6 μmol/mg), the fast release kinetics associated with Alg-PAPA/NO could have resulted from premature NO release (i.e., prior to associating with the bacteria). On the other hand, the greater concentrations needed for Alg-DETA/NO can be attributed to the lower amounts of NO released by the system after 4 h (~0.10 μmol/mg) compared to the other three alginate modifications.

Greater concentrations of the NO-releasing alginates were necessary to achieve bactericidal activity against *S. aureus* relative to *P. aeruginosa*. This decrease in susceptibility is believed to be due to differences in the composition of the peptidoglycan layer between Gram-positive and -negative bacteria. Gram-negative bacteria, such as *P. aeruginosa*, possess a lipid-rich outer membrane and thin peptidoglycan sheet as opposed to the thicker more resistant peptidoglycan layer on the outer wall of Gram-positive bacteria, such as *S. aureus*. This more robust membrane is believed to decrease the diffusion of NO into the bacterium, thus requiring higher NO doses to achieve killing.

Anti-biofilm efficacy. In addition to exhibiting bactericidal action against planktonic bacteria, the NO-releasing alginate scaffolds also proved effective against P. aeruginosa and S. aureus biofilms. To evaluate the anti-biofilm efficacy of the different NO-releasing alginate scaffolds, P. aeruginosa and S. aureus biofilms were exposed to 4-64 mg/mL NO-releasing alginates for 24 h in PBS (pH 7.4). Similar to planktonic studies, increased bactericidal activity was seen against P. aeruginosa compared to S. aureus biofilms (Table 4). Worley et al. demonstrated reduced penetration of NO-releasing poly(amido amine) dendrimers into S. aureus biofilms relative to P. aeruginosa due to differences relating to the biofilm architecture. Without being bound to a particular mechanism, this observation suggests increased NO tolerance for S. aureus biofilms over P. aeruginosa due to hindered NO donor scaffold diffusion. In addition, P. aeruginosa and S. aureus biofilms have been reported to exhibit distinct planktonic dispersal mechanisms believed to influence their susceptibility to antibacterial agents.

TABLE 4

Minimum biofilm eradication concentrations ($MBEC_{24\,h}$) against P. aeruginosa and S. aureus biofilms.[a]

| Scaffold | P. aeruginosa | | S. aureus | |
| --- | --- | --- | --- | --- |
| | $MBC_{24\,h}$ (mg/mL) | NO dose[b] (μmol/mL) | $MBC_{24\,h}$ (mg/mL) | NO dose[b] (μmol/mL) |
| Alg-DETA/NO | 8 | 2.6 ± 0.1 | 16 | 5.2 ± 0.2 |
| Alg-DPTA/NO | 8 | 3.4 ± 0.0 | 16 | 6.8 ± 0.1 |
| Alg-PAPA/NO | 32 | 19.6 ± 3.8 | 64 | 39.2 ± 7.6 |
| Alg-SPER/NO | 16 | 10.3 ± 1.8 | 32 | 20.7 ± 3.6 |

[a]Each parameter was analyzed with multiple replicates (n ≥ 3).
[b]NO dose was calculated from 24 h NO totals in PBS pH 7.4.

Figure 2A:
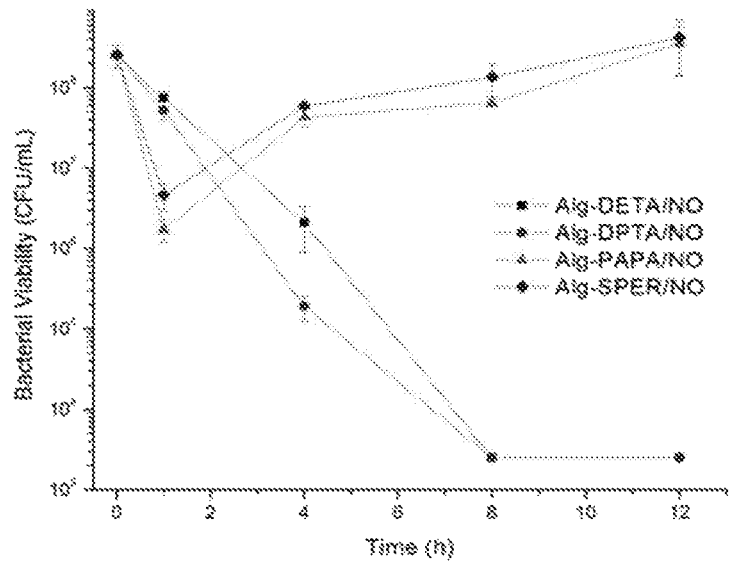
FIGS. 2A and 2B show time-based bactericidal efficacy for embodiments of NO-releasing alginates.
Figure 2B:
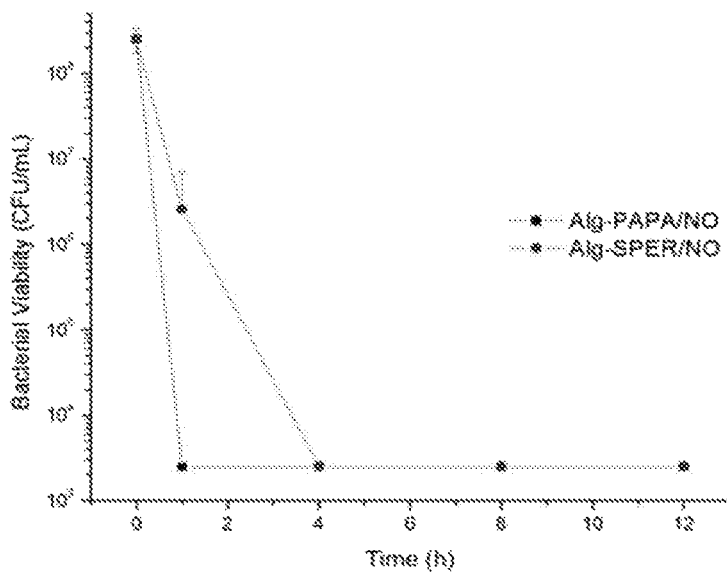

The alginate scaffolds with longer half-lives (~4-13 h) consistently required lower alginate concentrations, and thus lower NO doses, to eradicate biofilm-based bacteria than alginate scaffolds with shorter half-lives (~0.5-1 h). This feature was observed regardless of Gram class and suggests that slower, sustained NO release ensures more effective NO delivery. In agreement with this rationale, premature NO release from both Alg-SPER/NO and Alg-PAPA/NO decreased the amount of NO delivered to the biofilm. To test the eradication efficacy of the materials over time, P. aeruginosa biofilms were treated with equal concentrations (8 mg/mL) of the different NO-releasing alginates (FIG. 2A) and viability was assessed at various exposure times. At 1 h, treatment with either Alg-PAPA/NO or Alg-SPER/NO resulted in a 1 to 2-log reduction in biofilm bacterial viability, as expected based on the NO-release half-lives for the two NO-releasing alginates (~0.5-1.4 h). However, the low NO concentrations released from the alginate at longer durations were insufficient to cause bacterial death, as the concentration of viable P. aeruginosa recovers to ~108 CFU/mL after 4 h. At $MBEC_{24h}$, Alg-SPER/NO and Alg-PAPA/NO (FIG. 2B) elicited a 5-log reduction in bacterial viability after 1 h and 4 h exposures with no observable bacterial growth for up to 12 h. Without being bound by theory, it is believed that increased alginate (i.e., NO) concentrations improve the efficacy of the faster NO-releasing alginates through rapid bacterial death caused by the large initial NO burst.

In contrast to the fast NO-release systems, the alginate scaffolds with slower release kinetics (~4 and 13 h for Alg-DPTA/NO and Alg-DETA/NO, respectively) elicited a more gradual decrease in viability at the same concentration (i.e., 8 mg/mL), eventually achieving a 5-log reduction after 8 h of exposure. Indeed, results indicate that slower, sustained NO-release profiles are preferred for biofilm eradication when using lower alginate concentrations.

Figure 3A:
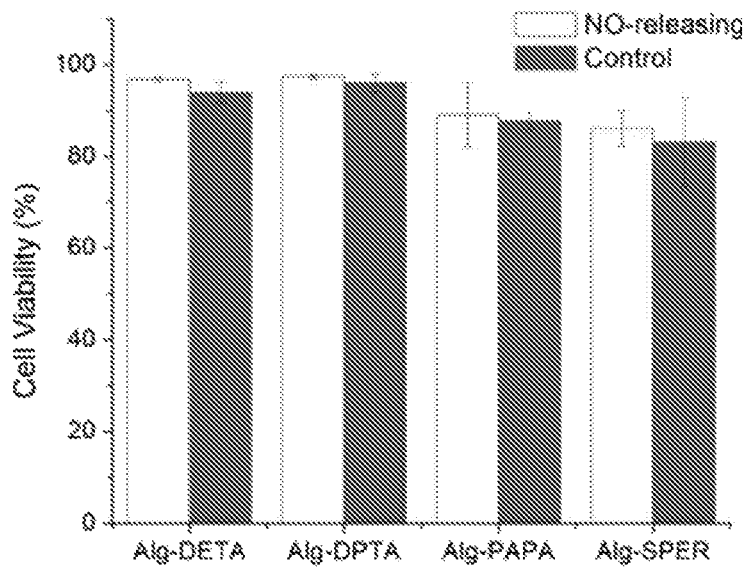
FIGS. 3A and 3B show the viability of A549 cells exposed to control and embodiments of NO-releasing alginates. Specifically, at the MBEC24h against (FIG. 3A) P. aeruginosa and (FIG. 3B) S. aureus. Studies consisted of at least three experiments with error bars representing the standard deviation.
Figure 3B:
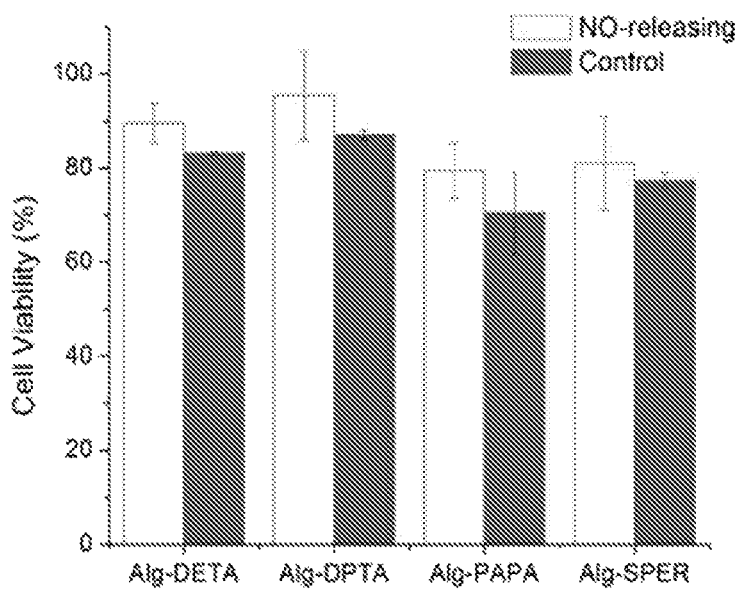
Figure 4A:
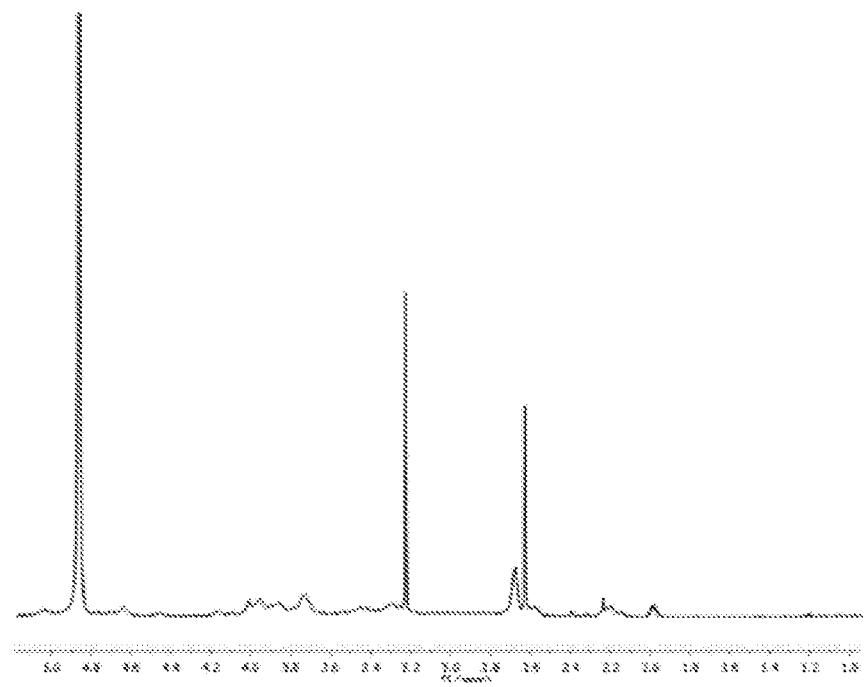
FIGS. 4A-4D show representative 1H NMR spectra of an embodiment of Alg-DETA (FIG. 4A), (FIG. 4B) an embodiment of Alg-DPTA, (FIG. 4C) an embodiment of Alg-PAPA, and (FIG. 4D) an embodiment of Alg-SPER in D2O.
Figure 4B:
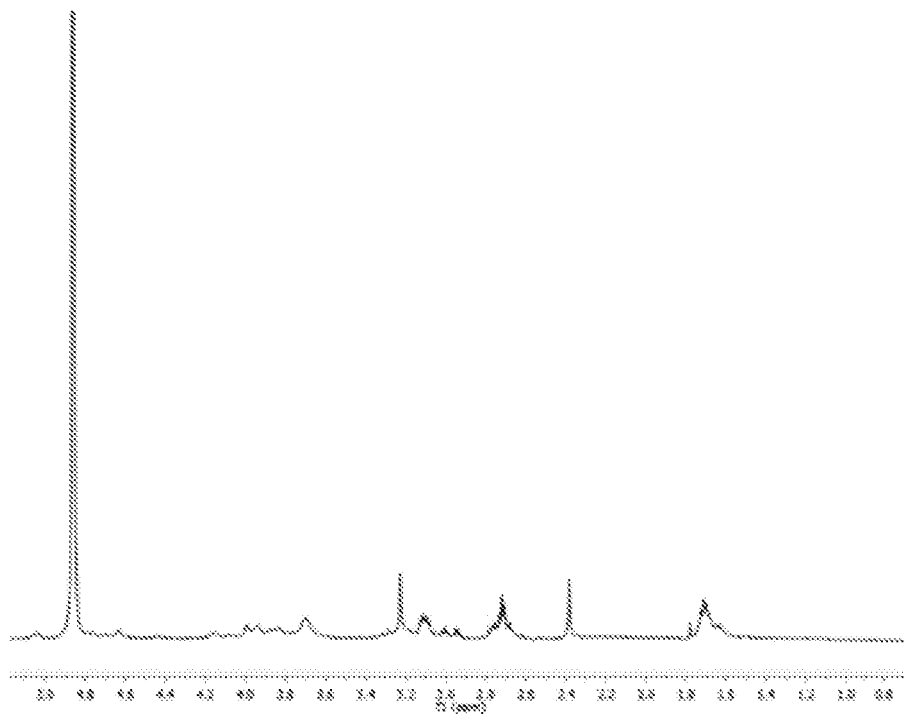
Figure 4C:
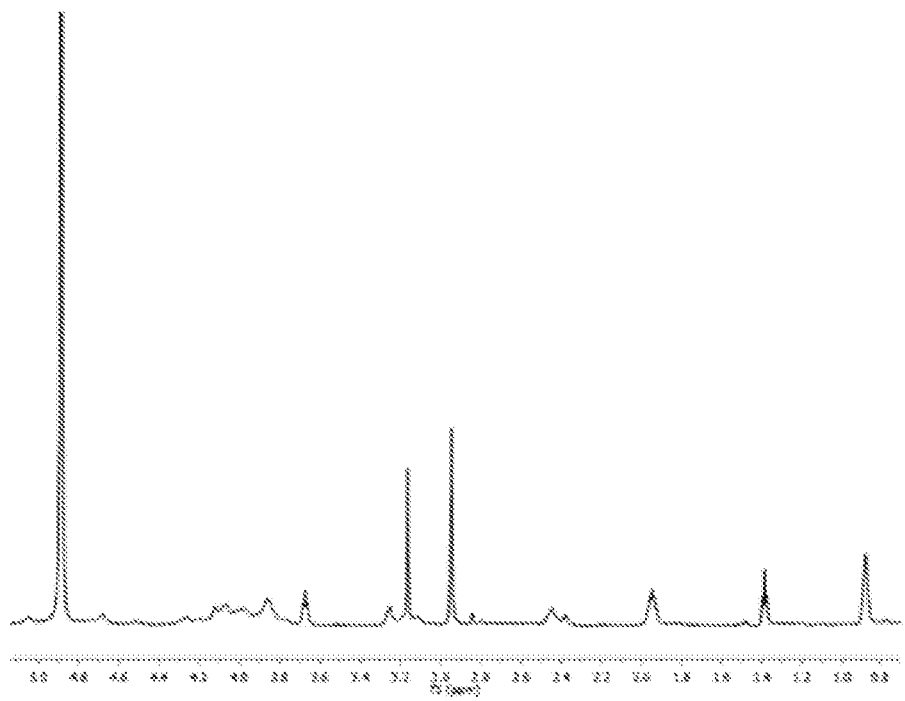
Figure 4D:
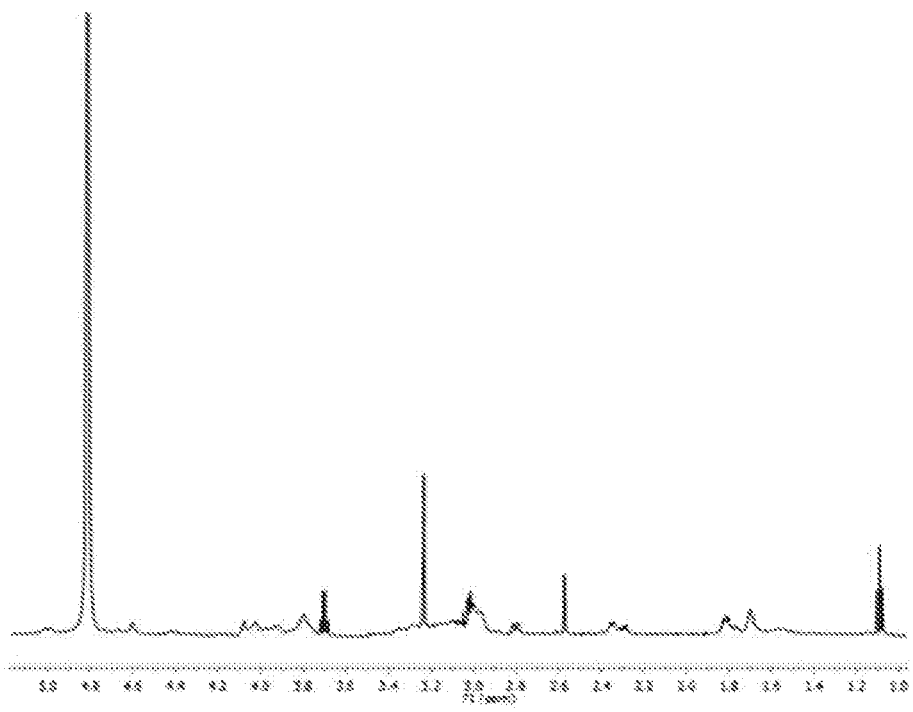
Figure 5A:
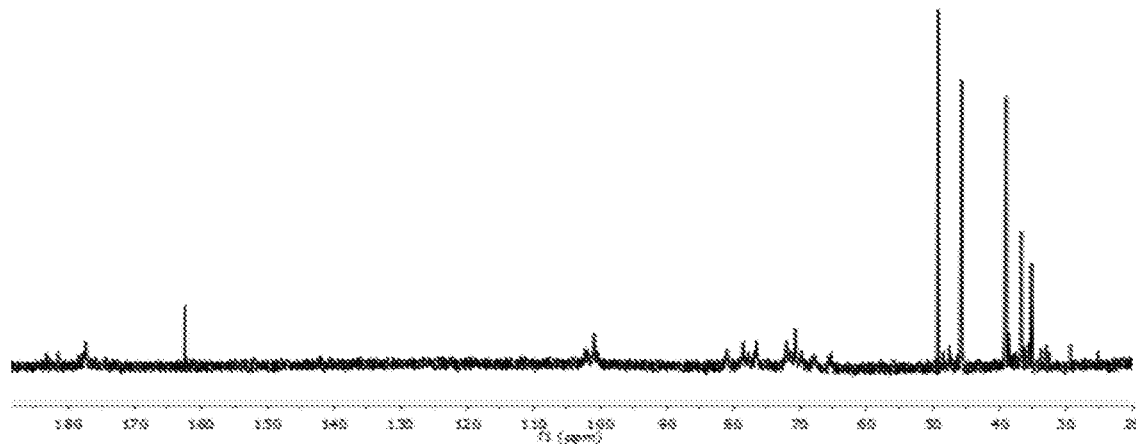
FIGS. 5A-5D show representative 13C NMR spectra of (FIG. 5A) an embodiment of Alg-DETA, (FIG. 5B) an embodiment of Alg-DPTA, (FIG. 5C) an embodiment of Alg-PAPA, and (FIG. 5D) an embodiment of Alg-SPER in D2O.
Figure 5B:
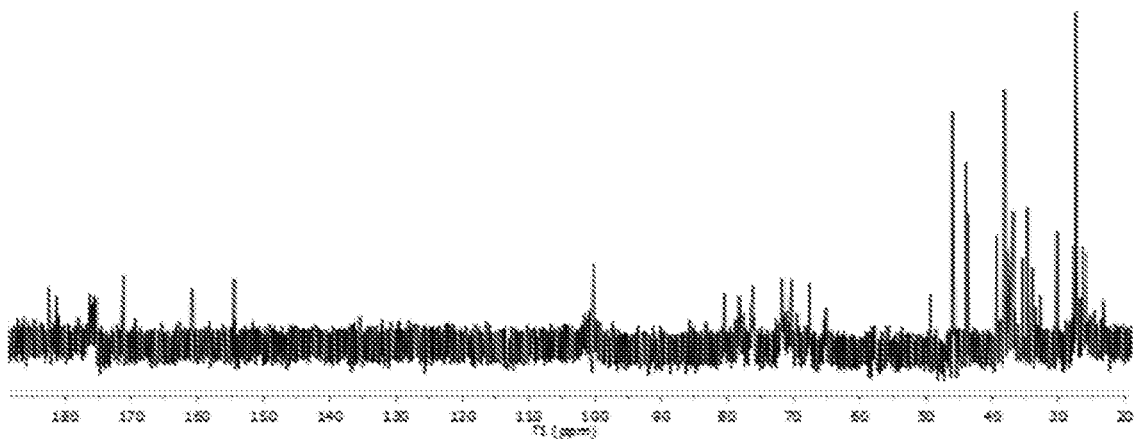
Figure 5C:
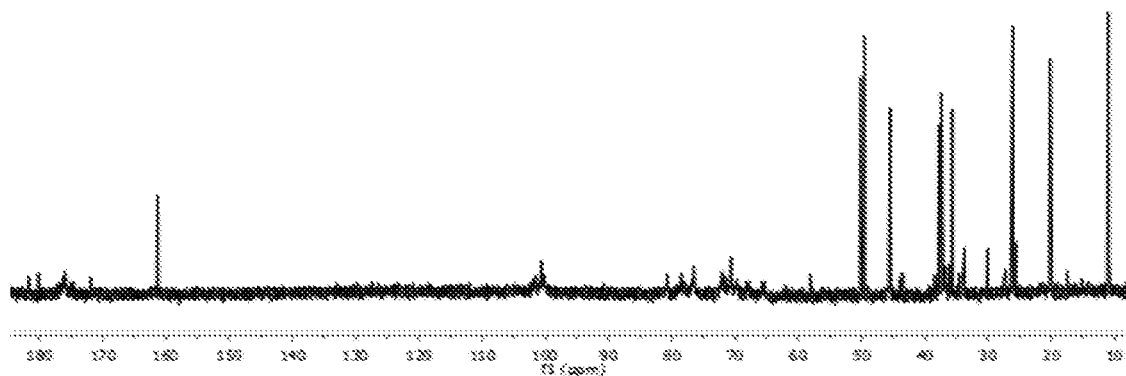
Figure 5D:
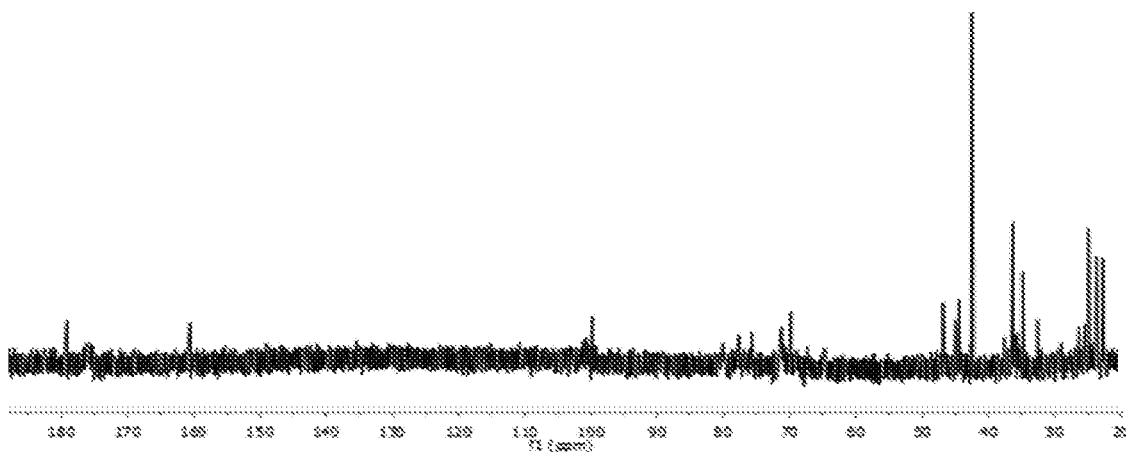
Figure 6A:
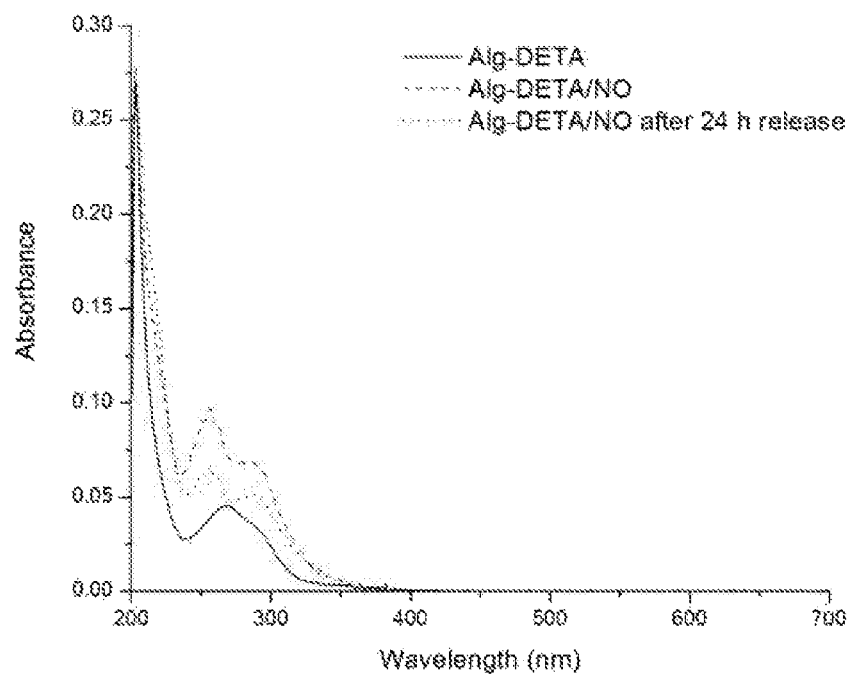
FIGS. 6A-6D show representative UV-vis spectra for an embodiment of secondary-amine and N-diazeniumdiolate alginate of (FIG. 6A) Alg-DETA/NO, (FIG. 6B) an embodiment of Alg-DPTA/NO, (FIG. 6C) an embodiment of Alg-PAPA/NO, and (FIG. 6D) an embodiment of Alg-SPER/NO.
Figure 6B:
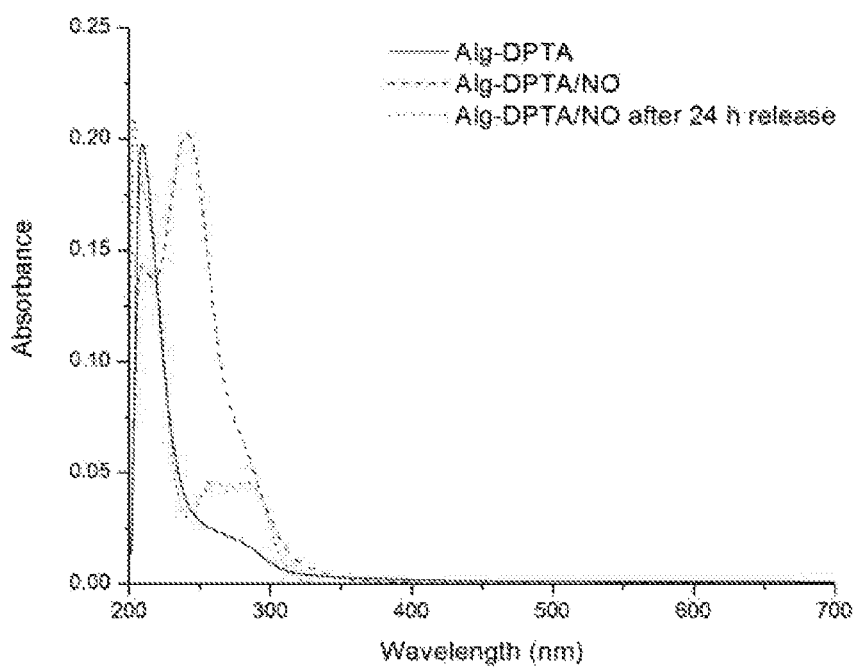
Figure 6C:
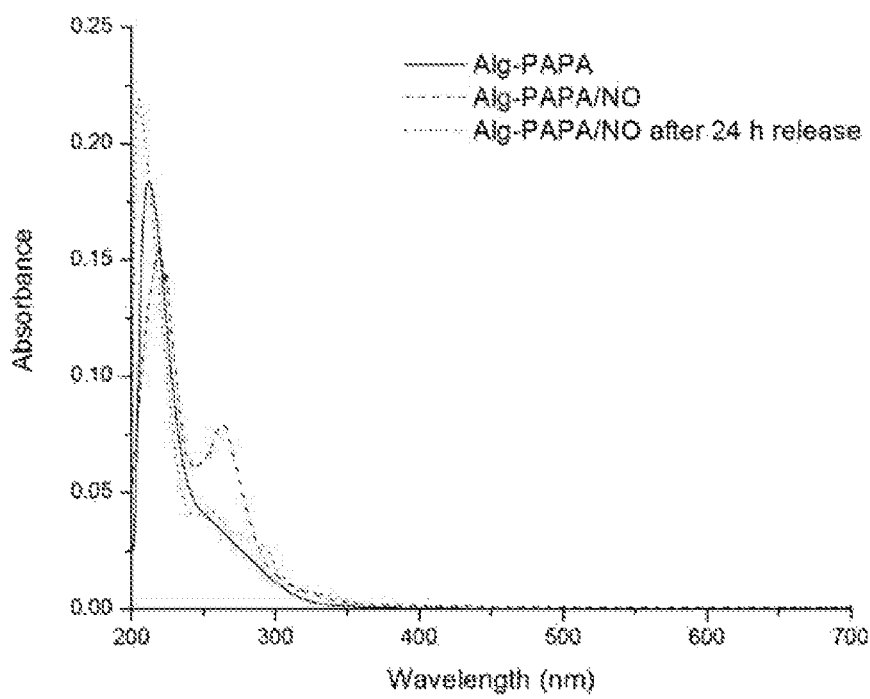
Figure 6D:
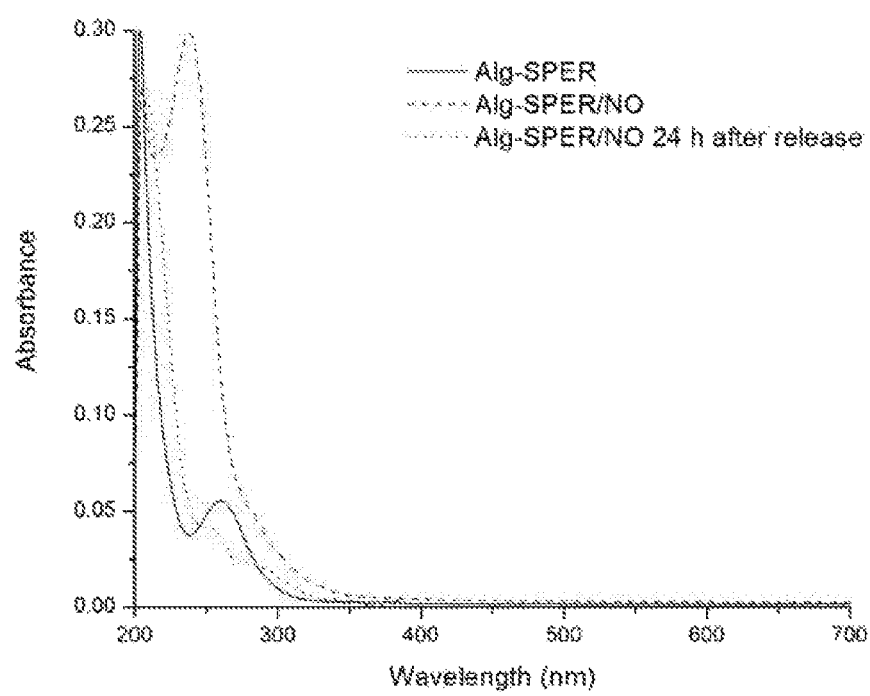

In Vitro Cytotoxicity against A549 cells. One of the properties of alginate for use in biomedical applications is its low toxicity to mammalian cells. However, the effects of modifying the alginate backbone with N-diazeniumdiolate-bearing polyamines are unknown. Thus, the cytotoxicity of control and NO-releasing alginates was compared by exposing human respiratory epithelial (A549) cells. A549 cells are commonly used as a pulmonary epithelial cell model for in vitro cytotoxicity studies. The toxicity of the alginate scaffolds was evaluated over 24 h at their MBECs against both P. aeruginosa and S. aureus. Cell viabilities were determined using the trypan blue dye exclusion assay; dead cells with compromised cell membranes allow for trypan dye inclusion, whereas living cells with intact cell membranes exclude the dye. As shown in FIG. 3, the control and NO-releasing alginate scaffolds did not exhibit significant toxicity against A549 cells at their MBECs, highlighting an advantage of these materials as anti-biofilm agents compared to other, more toxic macromolecular NO-release systems (e.g., silica nanoparticles and dendrimers). The NO-releasing scaffolds also promoted slight increases in cellular viability compared to the alginate controls, corroborating previous reports that certain levels of NO may promote cell proliferation. Collectively, the low toxicity of the NO-releasing alginates at the bactericidal concentrations shows promise for their use as therapeutics for wound healing and cystic fibrosis.

N-diazeniumdiolate-functionalized alginate scaffolds capable of diverse NO-release kinetics (0.5-13 h half-lives) were developed as biodegradable antibacterials. The biocidal efficacy of the NO-releasing alginate materials was demonstrated against both planktonic and biofilm-based forms of P. aeruginosa and S. aureus. Alginate modifications that resulted in slow and sustained NO release (i.e., Alg-DPTA/NO and Alg-DETA/NO) proved more effective against both Gram-negative and Gram-positive biofilms used in this study, resulting in eradication at low alginate/NO concentrations. Such materials exerted little to no toxicity against A549 cells, highlighting a unique benefit associated with the use of NO-releasing alginates. On the basis of this work, the NO-releasing alginate materials may be used as antibacterial agents in chronic infections (e.g., as a treatment for cystic fibrosis).

Example 4: CF Studies

Nitric oxide (NO), an endogenously produced free radical that has bactericidal action and regulates relevant biological processes has potential as a therapeutic agent for the treatment of CF. The broad spectrum antimicrobial activity of NO against both Gram-positive and Gram-negative bacteria is due to nitrosative and oxidative stress, disrupting cellular function through lipid peroxidation and DNA deamination. Nitric oxide functions as a mucolytic and stimulates ciliary clearance, making it a candidate as a CF therapeutic. While initial studies with gaseous NO show a reduction in airway inflammation and improved lung function, therapeutic benefit is limited by toxicity concerns and patient compliance. In some embodiments, macromolecular scaffolds that release NO under physiological conditions are better suited for biomedical due to improved bactericidal efficacy and tunable release kinetics, with the capacity for sustained release. In particular, biopolymers, such as chitosan, alginate, and hyaluronic acid, may represent successful candidates as NO delivery scaffolds due to their biocompatible and biodegradable characteristics.

Cationic chitosan oligosaccharides show some activity as NO-releasing scaffold against both planktonic and biofilm *P. aeruginosa*. However, a comparative study showed hyaluronic acid, an anionic biopolymer, is more mucoadhesive than chitosan. A strong anionic charge on the polymer was shown to be necessary for bioadhesion.

The following experiments show the testing of three distinct polysaccharides, two natural biopolymers, alginate (Alg) and hyaluronic acid (HA), and one synthetic, carboxymethylcellulose (CMC), with respect to mucolytic clearance potential and NO release. In some embodiments, these polymers and other biocompatible polymers, may be used for the treatment of CF. By combining the rheological benefits of a biopolymer with the antimicrobial and mucolytic action of NO, a new CF therapeutic that is capable of penetrating the thick mucus in the airway and eradicating chronic bacterial infection, biofilms, and drug-resistant strains is provided. The impact of the scaffold on mucus rheology and bactericidal and mucolytic action of NO was tested.

Without being bound to a particular mechanism, it is believed that anionic biopolymers of larger molecular weights significantly impact mucus rheology because the anionic charge disrupts electrostatic interactions of mucin chains and higher molecular weights improve bioadhesion, mucin network entanglement and contact time.

TABLE 5

Molecular weight of selected biopolymers to be investigated as determined by light scattering or reported by supplier (*)

| Biopolymer | Molecular Weight (kDa) |
|---|---|
| CSO | 5 ± 1 |
| Alg | 232 ± 77 |
| AlgG | 16 ± 8 |
| AlgM | 21 ± 8 |
| AOD | 5 |
| *HA | 1500-1800 |
| *CMC | 250 |

Degradation and characterization of biopolymers. The elucidation of the biopolymer properties that decrease mucus viscoelasticity provides insight into the usefulness of a NO-release scaffold for CF therapy. As such, a number of biopolymer compositions and molecular weights were evaluated. High molecular weight chitosan is a cationic scaffold with low water solubility. To impart solubility, chitosan was oxidatively degraded to produce a chitosan oligosaccharide (CSO). Anionic scaffolds included alginate (Alg), hyaluronic acid (HA), and carboxymethylcellulose (CMC), though other biocompatible anionic polymers are envisioned employed, depending on the embodiment. High molecular weight alginate was degraded by acid hydrolysis to produce polysaccharides of similar size with different guluronic acid (G) residue content: AlgG-70%, and AlgM-30%. To compare alginate and CSO, Alg was oxidatively degraded to produce alginate oligosacchardies (AOD). For example, oxidative degradation of 300 kDa alginate (Alg300) yielded alginate 5 kDa oligosaccharides (Alg5). Molecular weight of scaffolds was determined by GPC/SEC-MALS. Evaluation of these biopolymers allowed for comparison of the effects of charge, size, and composition on mucus rheology.

Analysis of viscoelasticity using a quartz crystal microbalance with dissipation (QCM-D). The interactions of biopolymers and mucins were studied with QCM-D to evaluate rheological changes in mucins due to biopolymer exposure. Without being bound to a particular theory, the ability to increase mucin layer thickness and decrease viscoelasticity through disrupting mucin network interactions should lead to improved drug diffusion in mucus. Interaction studies were performed using a Q-Sense Analyzer (Biolin Scientific, Stockholm, Sweden) QCM-D, peristaltic pump, and piezoelectric AT-cut quartz crystals with gold electrodes on either side. A solution of HBE mucins was flowed across the crystal until the resonant frequency ($\Delta f$) and dissipation ($\Delta D$) signals established a baseline followed by washing with phosphate buffered saline (PBS). Biopolymer solution was then flowed through the chamber and washed with PBS after signals reached a new baseline.

Figure 14:
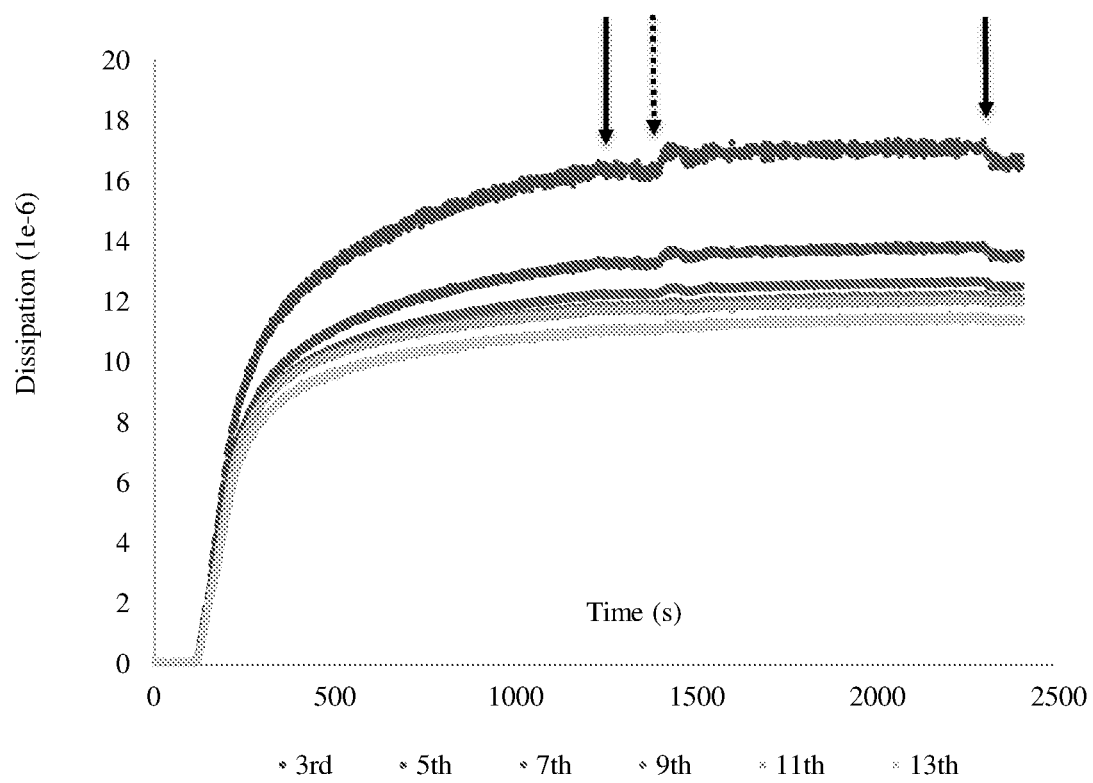
FIG. 14 shows dissipation changes with time for oxidatively degraded to chitosan oligosaccharide (CSO) exposure to HBE mucins. The 3rd, 5th, 7th, 9th, 11th, and 13th overtones are shown. Black arrows indicate PBS rinsing and dashed arrow indicates CSO-1 introduction.

The binding of the mucins proved irreversible as the frequency was unaffected by the rinsing with PBS (FIG. 14). The CSO interacted with the mucins, slightly increased dissipation, and returned close to the baseline after the PBS rinse. While CSO initially appeared to have little effect on the rigidity of the mucin layer, the effects of exposure are evident after Voight modeling (Table 6). As shown in Table 6, CSO significantly decreased mucin layer thickness.

TABLE 6

Information about the adsorbed layer after exposure to biopolymer scaffolds determined by Voight modeling. (*$p < 0.05$, **$p < 0.001$).

| Scaffold | Thickness (nm) | Viscosity (mPa · s) | Elasticity (kPa) |
|---|---|---|---|
| Blank | 26.9 ± 5.4 | 11.89 ± 6.09 | 1.103 ± 0.132 |
| CSO | 19.4 ± 1.8* | 19.02 ± 7.85 | 1.194 ± 0.129 |
| Alg | 28.8 ± 9.4 | 11.47 ± 1.28 | 1.134 ± 0.128 |
| AlgG | 28.6 ± 5.4 | 8.39 ± 2.20 | 0.997 ± 0.126 |
| AlgM | 26.6 ± 9.0 | 3.05 ± 3.40 | 1.077 ± 0.125 |
| AOD | 21.4 ± 1.5 | 13.36 ± 3.04 | 1.019 ± 0.125 |
| HA | 8.7 ± 0.4** | 119.84 ± 20.58* | 1.562 ± 0.124* |
| CMC | 7.5 ± 0.5** | 7.48 ± 1.09* | 1.480 ± 0.124 |

Figure 15:
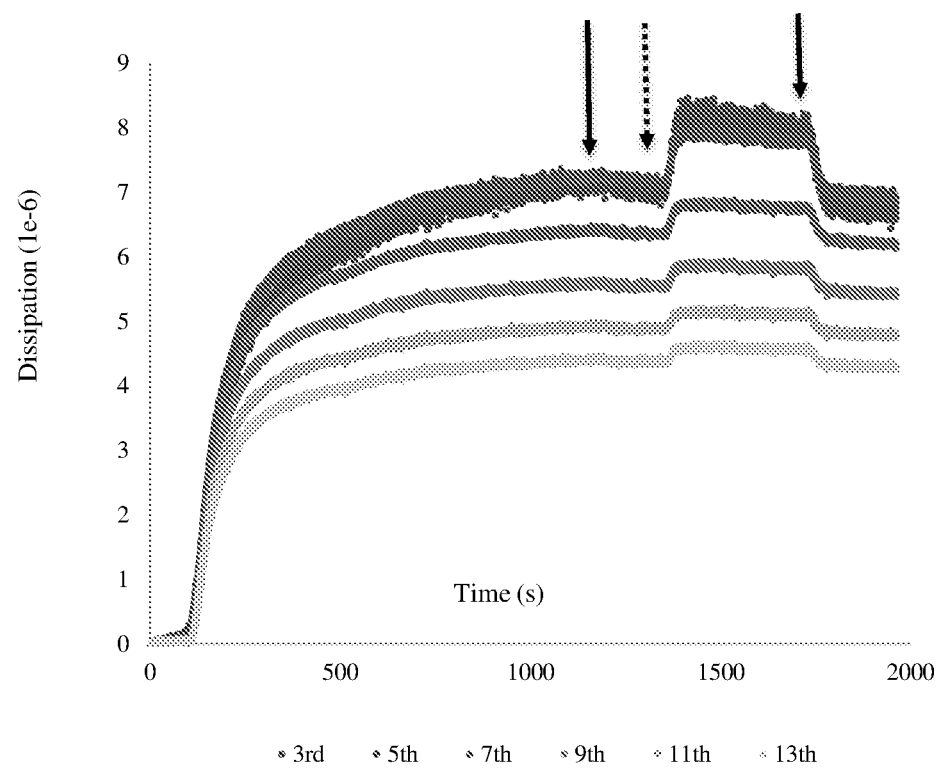
FIG. 15 shows dissipation changes with time for alginate. The 3rd, 5th, 7th, 9th, 11th, and 13th overtones are shown. Black arrows indicate PBS rinsing and dashed arrow indicates Alg introduction.

The electrostatic attraction between the positively charged chitosan scaffold and negatively charged mucins likely caused collapse of the mucin layer and increased crosslinking which subsequently decreased the thickness of the adsorbed layer. FIG. 14 shows dissipation changes with time for CSO-1 exposure to HBE mucins. The 3rd, 5th, 7th, 9th, 11th, and 13th overtones are shown. Black arrows indicate PBS rinsing and dashed arrow indicates CSO-1 introduction. Similar to the changes observed in FIG. 14, slight changes in mass and dissipation were also observed after exposure to Alg, CMC, and HA, with only Alg shown for comparison (FIG. 15). FIG. 15 shows dissipation changes with time for Alg. The 3rd, 5th, 7th, 9th, 11th, and 13th overtones are shown. Black arrows indicate PBS rinsing and dashed arrow indicates Alg introduction. Both Alg and CMC caused a large increase in dissipation upon flow of the polymer solution through the chamber, indicating a soft, viscoelastic layer was coupled to the crystal. Once rinsed with PBS, the dissipation curves returned to baseline, suggesting that the polymer was not strongly bound to the mucin layer, but significantly affected both the viscoelasticity and hydration of the film during exposure. Hyaluronic acid increased dissipation slightly, but established a baseline below the original dissipation value for the mucins, indicating exposure to HA increased layer rigidity. No changes were noted from baseline with the other alginates.

Both HA and CMC significantly decreased layer thickness to a greater degree than CSO (Table 6). High molecular weight HA and cellulose-ethers like CMC increase solution viscosity. The large molecular weights of these polymers, 1.5 MDa and 250 kDa respectively, may contribute to improved bioadhesion and entanglement, thereby increasing the viscosity, which is in agreement with the decrease in layer thickness as mucin layer collapse occurs. The alginate scaffolds did not significantly affect mucins, but AOD showed a trend of decreasing layer thickness. Oligoguluronates modify mucin networks by interrupting mucin-mucin interactions, which could cause the decreased thickness observed. Based on this data, the alginate derivatives appear to be the scaffolds that do not increase mucin layer viscoelasticity and as such may have beneficial effects on bulk mucus rheology.

Effects of biopolymer exposure on mucus characterized by parallel plate rheology. Information obtained from QCM-D experiments on mucins may be used in conjunction with parallel plate rheology experiments on mucus to obtain a clearer understanding of NO-delivery from polymer scaffolds. Parallel plate rheology represents a macrorheology technique that allows for characterization of the bulk rheology of CF mucus (i.e., viscous modulus ($G''$), elastic modulus ($G'$), and complex viscosity ($\eta^*$)). Bulk rheology can be used to determine properties and/or macroscale functions of mucus, including mucociliary clearance. The results from the QCM-D experiments indicate alginate derivatives are promising as therapeutics due to their low impact on the mucin layer. CSO, HA, and CMC demonstrate increased mucin viscoelasticity relative to alginate. The alginate scaffolds were selected to evaluate the effect of molecular weight and G residue content on bulk mucus rheology. HA was chosen for additional testing since it significantly increased mucin viscoelasticity.

Biopolymer scaffolds were inoculated into HBE mucus (3% solids wt/wt) to a final concentration of 10 mg/mL and incubated at 37° C. with rotation for 18 h. The rheological properties of each sample were measured via amplitude sweep and frequency sweep experiments on a Discovery HR-3 rheometer (TA Instruments, New Castle, Del.) with a 20 mm parallel plate set to a gap thickness of 50 µm. Experiments were performed in triplicate at 23° C. to prevent sample dehydration.

Figure 16A:
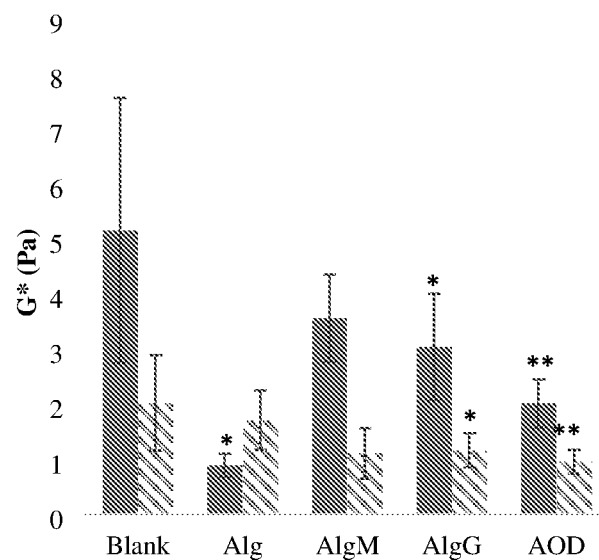
FIG. 16A shows the elastic (solid) and viscous (striped) moduli and FIG. 16B shows complex viscosity at 10 rad/s of HBE mucus following 18 h treatment with alginate biopolymers at 37° C. (*$p<0.05$, **$p<0.01$).
Figure 16B:
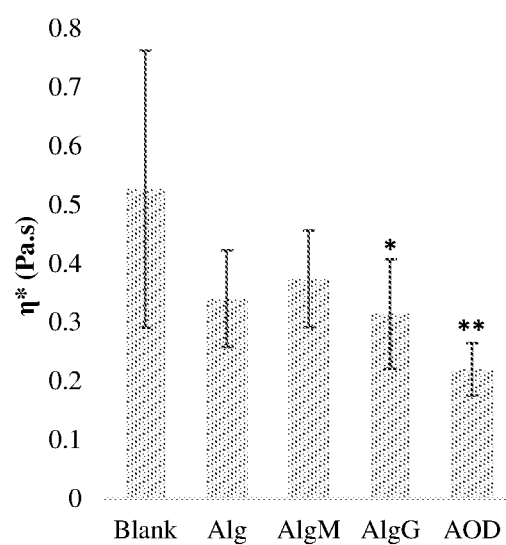

Useful delivery scaffolds can decrease $G'$, $G''$ and/or $\eta^*$ to promote drug diffusion through mucus, and/or a reduction in both viscosity and elasticity is associated with improved ciliary clearance in model studies (e.g., frog studies, etc.). After exposure to AOD, $G'$, $G''$, and $\eta^*$ of mucus were significantly reduced (FIGS. 16A-16B). FIG. 16A shows the elastic (solid) and viscous (striped) moduli and FIG. 16B shows complex viscosity at 10 rad/s of HBE mucus following 18 h treatment with alginate biopolymers at 37° C. ($*p<0.05$, $**p<0.01$). Without being bound to a particular mechanism, this was a result likely caused by the oligoguluronates interrupting mucin-mucin interactions by interacting with amino groups on the mucins and interfering with hydrogen bonding. It is believed that the reduced viscoelasticity caused by AOD should improve both cough and ciliary clearance, which are important for removing pathogens and largely dependent upon mucus viscoelasticity, making AOD a highly promising NO-delivery scaffold.

Figure 17A:
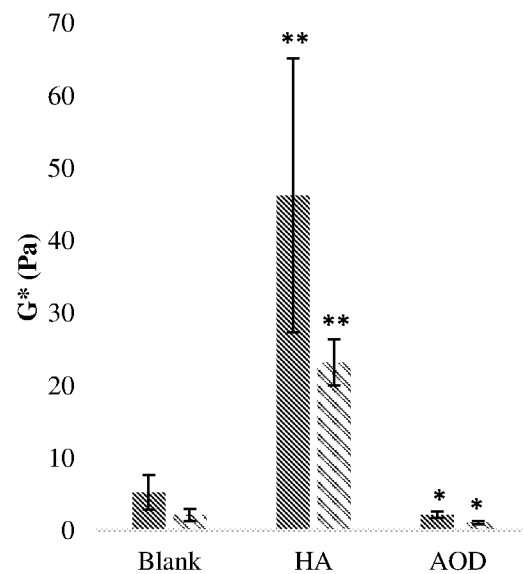
FIG. 17A shows the elastic (solid) and viscous (striped) moduli and FIG. 17B shows complex viscosity at 10 rad/s of HBE mucus following 18 h treatment with AOD and HA biopolymers at 37° C. (*$p<0.01$, **$p<0.001$).
Figure 17B:
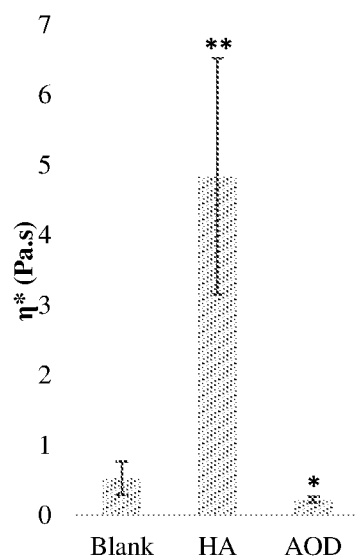

Additionally, Alg and AlgG slightly decreased elasticity of the mucin layer. Without being bound to a particular theory, it is believed that this was caused by hydrogen bonding of the guluronic residues with mucins and disruption of mucin-mucin interactions, decreasing crosslinking. In contrast, AlgM, having fewer G residue content, did not significantly alter mucus rheology. Of note, HA caused a dramatic increase in $G'$, $G''$, and $\eta^*$ (FIGS. 17A-17B). FIG. 17A shows the elastic (solid) and viscous (striped) moduli and FIG. 17B shows complex viscosity at 10 rad/s of HBE mucus following 18 h treatment with AOD and HA biopolymers at 37° C. ($*p<0.01$, $**p<0.001$).

This data corroborates the trends seen in the QCM-D experiments where HA increased viscoelasticity. Without being bound to a particular theory, this was likely due to significant bioadhesion and entanglement. Based on this data, both cough clearance and ciliary beating would be negatively affected by exposure to HA.

Upon considering both the QCM-D and parallel plate rheology results, AOD appeared to be a promising scaffold for promoting mucus clearance. Lower molecular weight, high G residue content, and a negative charge appear to be properties that decrease viscoelasticity of mucus. The oligoguluronates decreased mucin layer thickness and caused a significant decrease in the bulk viscoelasticity of mucus. It is believed that these trends continue in biofilm-containing mucus and in the effect on mucus transport.

Figure 18:
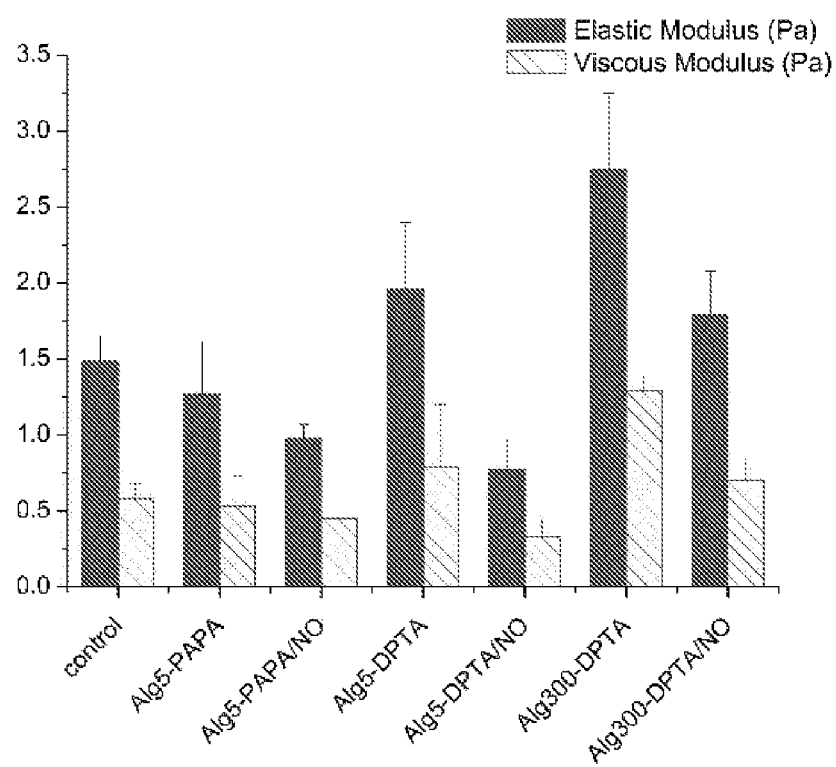
FIG. 18 shows elastic (solid) and viscous (striped) moduli.

Influence of nitric oxide release on viscoelasticity. The positive mucolytic results above are further enhanced with the addition of NO release. As shown in FIG. 18, the addition of NO release ability whether rapid (e.g., PAPA) or more sustained (e.g. DPTA) further decreases both the elastic and viscous moduli. FIG. 18 shows elastic (solid) and viscous (striped) moduli.

Thus, NO-releasing alginates (e.g., low MW, Alg5; or, high MW, Alg300) have both dual antibacterial and mucolytic properties. With favorable biocompatiblity and biodegradability, and the ability to reduce biofilm viscosity as well, make the NO-releasing scaffolds (e.g., alginate scaffolds) a highly attractive CF therapeutic.

TABLE 7

Nitric oxide-release properties of alginates in PBS pH 7.4. Of note, the release kinetics are easily modified by NO donor precursor choice.

| Scaffold | t[NO] (µmol/mg) | [NO]$_{max}$ (ppb/mg) | $t_{1/2}$ (h) | $t_d$ (h) |
|---|---|---|---|---|
| Ag-DETA/NO | 0.40 ± 0.13 | 175 ± 98 | 13.1 ± 5.83 | 40.3 ± 10.2 |
| Alg-DPTA/NO | 0.42 ± 0.04 | 428 ± 123 | 3.37 ± 0.64 | 16.1 ± 2.88 |
| Alg-PAPA/NO | 0.61 ± 0.13 | 2110 ± 908 | 0.46 ± 0.12 | 6.08 ± 0.88 |
| Alg-SPER/NO | 0.64 ± 0.16 | 1236 ± 241 | 1.29 ± 0.41 | 14.6 ± 3.54 |

TABLE 8

Planktonic MBCs for NO-releasing alginates. Bacteria cultures grown in TSB and exposed to alginate in PBS, pH 7.4 with 1% TSB. As expected, larger doses were required for the Gram-positive bacteria.

| | P. aeruginosa | | S. aureus | |
|---|---|---|---|---|
| Scaffold | MBC$_{4h}$ (mg/mL) | NO dose (µmol/mg) | MBC$_{4h}$ (mg/mL) | NO dose (µmol/mg) |
| Alg-DETA/NO | 4 | 0.40 ± 0.04 | 8 | 0.80 ± 0.08 |
| Alg-DPTA/NO | 2 | 0.45 ± 0.01 | 4 | 0.88 ± 0.02 |

TABLE 8-continued

Planktonic MBCs for NO-releasing alginates. Bacteria cultures grown in TSB and exposed to alginate in PBS, pH 7.4 with 1% TSB. As expected, larger doses were required for the Gram-positive bacteria.

| | P. aeruginosa | | S. aureus | |
|---|---|---|---|---|
| Scaffold | $MBC_{4\,h}$ (mg/mL) | NO dose (μmol/mg) | $MBC_{4\,h}$ (mg/mL) | NO dose (μmol/mg) |
| Alg-SPER/NO | 1 | 0.49 ± 0.11 | 4 | 1.96 ± 0.45 |
| Alg-PAPA/NO | 2 | 1.18 ± 0.24 | 8 | 4.75 ± 0.95 |

TABLE 9

Biofilm MBECs for NO-releasing alginates. Biofilms were first grown for 2 d in TSB and then exposed to the alginates in PBS, pH 7.4 for 24 h. Of note, the NO release kinetics played a critical role with biofilm eradication. Consistent and continuous NO release proved better than an initial high NO burst only.

| | P aeruginosa | | S. aureus | |
|---|---|---|---|---|
| Scaffold | $MBEC_{24\,h}$ (mg/mL) | NO dose (μmol/mg) | $MBEC_{24\,h}$ (mg/mL) | NO dose (μmol/mg) |
| Alg-DETA/NO | 8 | 2.6 ± 0.1 | 16 | 5.2 ± 0.2 |
| Alg-DPTA/NO | 8 | 3.4 ± 0.0 | 16 | 6.8 ± 0.1 |
| Ag-SPER/NO | 16 | 10.3 ± 1.8 | 32 | 20.7 ± 3.6 |
| Ag-PAPA/NO | 32 | 19.6 ± 3.8 | 64 | 39.2 ± 7.6 |

Although the foregoing has been described in some detail by way of illustrations and examples for purposes of clarity and understanding, it is contemplated that modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the embodiments of the invention(s).

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a nitric oxide-releasing compound" includes "instructing the administration of a nitric oxide-releasing compound." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like.

The indefinite article "a" or "an" does not exclude a plurality. The term "about" as used herein to, for example, define the values and ranges of molecular weights means that the indicated values and/or range limits can vary within ±20%, e.g., within ±10%. The use of "about" before a number includes the number itself. For example, "about 5" provides express support for "5".

The invention claimed is:

1. A method of:
    (a) reducing microbial load on a surface comprising applying a compound comprising a nitric oxide donor to a surface contaminated with a plurality of microbes;
        wherein the nitric oxide donor generates nitric oxide and induces oxidative or nitrosative damage to microbial DNA and membrane structures, thereby reducing microbial load, and
        wherein said plurality of microbes comprises two or more of the following: gram-positive bacteria, gram-negative bacteria, fungi, yeast, and viruses;
    (b) treating a microbial infection comprising, contacting a surface contaminated with a plurality of microbes with a compound comprising a nitric oxide donor;
        wherein the nitric oxide donor generates nitric oxide and induces damage to the membrane or DNA of the microbes, thereby reducing the number of viable microbes and treating the infection, and
        wherein said plurality of microbes comprises one or more of viruses, gram positive bacteria, gram negative bacteria, drug resistant bacteria, molds, yeasts, fungi, and combinations thereof;
    (c) reducing the viscoelasticity of a mucus layer, comprising contacting a surface comprising a mucus layer with a compound comprising a nitric oxide donor;
        wherein the nitric oxide donor generates nitric oxide and
        wherein the nitric oxide disrupts mucin-mucin interactions in the mucus layer, thereby decreasing mucus viscoelasticity;
    or,
    (d) delivering nitric oxide to a target site at an antimicrobial concentration for a period of at least 1 to 15 hours, comprising contacting a target site contaminated with a microbial load with a compound comprising a nitric oxide donor;
        wherein the nitric oxide donor generates nitric oxide at a concentration sufficient to reduce the number of viable microbes at the target site;

wherein,
the compound in each of (a), (b), (c), and (d) is a functionalized alginate comprising one or more covalently modified monomers of Formula I

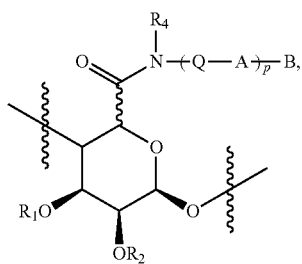

and optionally, one or more monomers of Formula II

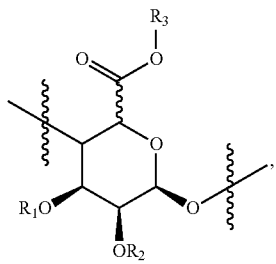

wherein,
$R_1$ and $R_2$ are each independently selected from the group consisting of hydrogen, $C_{1-5}$ alkyl(C=O)—, and $C_{1-5}$ alkyl;
$R_3$ is hydrogen or $C_{1-5}$ alkyl;
$R_4$ is, in each instance, hydrogen or $C_{1-5}$ alkyl;
Q is —$(CR_aR_b)_v$—;
wherein $R_a$ and $R_b$ are independently hydrogen or $C_{1-5}$ alkyl; and v is an integer from 2 to 6;
A is

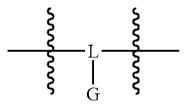

wherein, L is S, O, or N; and
G, in each instance, is hydrogen, is taken together with L to form a nitric oxide donor, or is absent; wherein the nitric oxide donor is selected from the group consisting of a diazeniumdiolate, a nitrosamine, a hydroxyl amine, a hydroxyurea, a nitrosothiol, a hydroxyl nitrosamine, and a combination thereof;
p is an integer from 1 to 10;
B is selected from the group consisting of hydrogen, —Y—Z, and $C_{1-5}$ alkyl, wherein said $C_{1-5}$ alkyl is optionally substituted with amino, hydroxyl, nitrile, $CO_2H$, mono($C_{1-6}$)alkylamino-, di($C_{1-6}$)alkylamino-, —(CO)$NR^cR^d$, or —$NR^c$(CO)$R^d$,
wherein $R^c$ and $R^d$ are each independently selected from the group consisting of hydrogen and $C_{1-6}$ alkyl, wherein Y has a structure of:

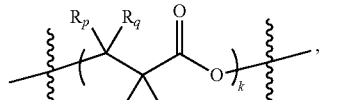

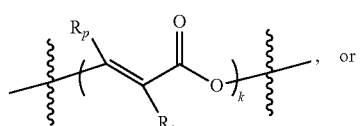

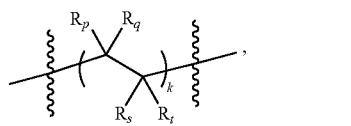

wherein $R_p$, $R_q$, $R_s$ and $R_t$, in each instance, are independently, hydrogen or hydroxyl; and
k is an integer from 1 to 20; and
Z has a structure of:

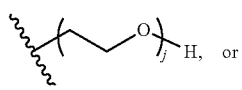

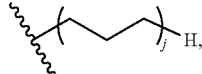

wherein j, in each instance, is an integer from 1 to 100; and
wherein the functionalized alginate comprises at least one monomer of Formula I containing the nitric oxide donor.

2. The method of claim 1, wherein said method is reducing microbial load on a surface comprising applying the compound comprising the nitric oxide donor to a surface contaminated with a plurality of microbes;
wherein the nitric oxide donor generates nitric oxide and induces oxidative or nitrosative damage to microbial DNA and membrane structures, thereby reducing microbial load, and
wherein said plurality of microbes comprises two or more of the following: gram-positive bacteria, gram-negative bacteria, fungi, yeast, and viruses.

3. The method of claim 1, wherein said method is treating a microbial infection comprising, contacting a surface contaminated with a plurality of microbes with the compound comprising the nitric oxide donor;
wherein the nitric oxide donor generates nitric oxide and induces damage to the membrane or DNA of the microbes, thereby reducing the number of viable microbes and treating the infection, and
wherein said plurality of microbes comprises one or more of viruses, gram positive bacteria, gram negative bacteria, drug resistant bacteria, molds, yeasts, fungi, and combinations thereof.

4. The method of claim 1, wherein said method is reducing the viscoelasticity of a mucus layer, comprising contacting a surface comprising a mucus layer with the compound comprising the nitric oxide donor;

wherein the nitric oxide donor generates nitric oxide and wherein the nitric oxide disrupts mucin-mucin interactions in the mucus layer, thereby decreasing mucus viscoelasticity.

5. The method of claim 1, wherein said method is delivering nitric oxide to a target site at an anti-microbial concentration for a period of at least 1 to 15 hours, comprising contacting a target site contaminated with a microbial load with the compound comprising the nitric oxide donor;

wherein the nitric oxide donor generates nitric oxide at a concentration sufficient to reduce the number of viable microbes at the target site.

6. The method of claim 1, wherein the functionalized alginate has a total releasable nitric oxide storage in a range of 0.1-1.0 μmol of nitric oxide per milligram of the functionalized alginate.

7. The method of claim 1, wherein L is N, and wherein the nitric oxide donor is selected from the group consisting of a diazeniumdiolate, a nitrosamine, a hydroxyl amine, a hydroxyurea, and a combination thereof.

8. The method of claim 7, wherein the functionalized alginate has a total releasable nitric oxide storage in a range of 0.1-1.0 μmol of nitric oxide per milligram of the functionalized alginate.

9. The method of claim 7, wherein the nitric oxide donor is a diazeniumdiolate.

10. The method of claim 7, wherein the nitric oxide donor is a nitrosamine.

11. The method of claim 7, wherein the nitric oxide donor is a hydroxyl amine.

12. The method of claim 7, wherein the nitric oxide donor is a hydroxyurea.

13. The method of claim 1, wherein one or more monomers of Formula II are present.

14. The method of claim 7, wherein one or more monomers of Formula II are present.

15. The method of claim 7, wherein $R_1$ and $R_2$ are hydrogen or $C_{1-5}$ alkyl; and $R_3$ is hydrogen.

16. The method of claim 15, wherein $R_1$, $R_2$, $R_3$, and $R_4$ are hydrogen.

17. The method of claim 7, wherein v is 2 or 3; and p is an integer from 1 to 3.

18. The method of claim 17, wherein B is —Y—Z.

19. The method of claim 18, wherein Y has the structure:

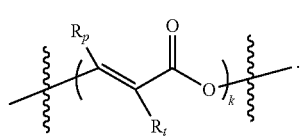

ii

20. The method of claim 18, wherein Z has the structure:

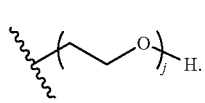

iv

21. The method of claim 17, wherein B is selected from the group consisting of hydrogen and $C_{1-5}$ alkyl, wherein said $C_{1-5}$ alkyl is optionally substituted with amino, hydroxyl, nitrile, $CO_2H$, mono($C_{1-6}$)alkylamino-, di($C_{1-6}$)alkylamino-, —(CO)$NR^cR^d$, or —$NR^c(CO)R^d$, and wherein $R^c$ and $R^d$ are each independently selected from the group consisting of hydrogen and $C_{1-6}$ alkyl.

* * * * *